United States Patent
Dohil et al.

(10) Patent No.: US 12,391,643 B2
(45) Date of Patent: Aug. 19, 2025

(54) SUBSTITUTED AMINO-THIOL AND AMINO-DISULFIDE COMPOUNDS, AND USES THEREOF

(71) Applicant: The Regents of the University of California, Oakland, CA (US)

(72) Inventors: Ranjan Dohil, San Diego, CA (US); Carlo Ballatore, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 956 days.

(21) Appl. No.: 17/429,885

(22) PCT Filed: Mar. 26, 2020

(86) PCT No.: PCT/US2020/025067
§ 371 (c)(1),
(2) Date: Aug. 10, 2021

(87) PCT Pub. No.: WO2020/198529
PCT Pub. Date: Oct. 1, 2020

(65) Prior Publication Data
US 2022/0135524 A1    May 5, 2022

Related U.S. Application Data

(60) Provisional application No. 62/823,892, filed on Mar. 26, 2019.

(51) Int. Cl.
*C07C 323/25* (2006.01)
*A61P 1/16* (2006.01)

(52) U.S. Cl.
CPC .............. *C07C 323/25* (2013.01); *A61P 1/16* (2018.01); *C07B 2200/05* (2013.01)

(58) Field of Classification Search
CPC .......... C07C 323/25; A61P 1/16; A61P 25/28; C07B 2200/05; C07B 59/001
See application file for complete search history.

(56) References Cited

U.S. PATENT DOCUMENTS

| | | | |
|---|---|---|---|
| 5,254,730 A | 10/1993 | Kilgore et al. | |
| 8,530,479 B2 | 9/2013 | Dhanoa et al. | |
| 2007/0197695 A1* | 8/2007 | Potyen | C08K 5/55 524/110 |
| 2014/0073694 A1* | 3/2014 | Cicchetti | A61P 43/00 514/665 |

FOREIGN PATENT DOCUMENTS

| | | |
|---|---|---|
| CN | 103442704 A | 12/2013 |
| CN | 107106875 A | 8/2017 |
| JP | 2011-505375 A | 2/2011 |
| JP | 2014-508758 A | 4/2014 |
| JP | 2017-533967 A | 11/2017 |
| WO | 2012/113079 A1 | 8/2012 |
| WO | 2016/073716 A1 | 5/2016 |
| WO | 2017/161318 A1 | 9/2017 |
| WO | 2021/022012 A1 | 2/2021 |

OTHER PUBLICATIONS

Dehennin, Biomedical Mass Spectrometry, vol. 7, Nos. 11 and 12, 1980 (Year: 1980).*
Stella, J. Pharmaceutical Sciences, 2010, 99(12), pp. 4755-4765). (Year: 2010).*
Pirali, J. Med. Chem., 2019, 62, 5276-5297 (Year: 2019).*
CDN Isotopes Inc., Registry Online, Search Date: Feb. 28, 2024, 4.21 RN:1219805-04 to 5.
Kaur et al., "Deuteration as a Tool for Optimization of Metabolic Stability and Toxicity of Drugs", Global Journal of Pharmacy & Pharmaceutical Science, Mar. 27, 2017, vol. 1, Issue 4, pp. 79-90.
Takahashi, Naoko, Office Action, Japan Patent Office, Application No. 2021-555221, Mar. 4, 2024.
Office Action, China National Intellectual Property Administration, Application No. 202080024298.3, Dec. 7, 2023.
Young, Lee, International Search Report & Written Opinion, United States Patent & Trademark Office, PCT/US2020/025067, Jun. 19, 2020.
Seitner, Irmgard, Extended European Search Report, Application No. 20778142.8, European Patent Office, Dec. 22, 2022.
Foster, Allan, "Deuterium Isotope Effects in Studies of Drug Metabolism," Trends in Pharmacol. Sci., 5:524-527, 1984.

* cited by examiner

*Primary Examiner* — Fereydoun G Sajjadi
*Assistant Examiner* — Luisalberto Gonzalez
(74) *Attorney, Agent, or Firm* — Gavrilovich, Dodd & Lindsey LLP

(57) ABSTRACT

The disclosure provides for new substituted cysteamine and cystamine compounds, pharmaceutical compositions made thereof, and methods thereof including the treatment of any disease or disorder in a subject that can benefit from one or more of the bioprotective effects of the compounds, including but not limited to, binding of cystine, reducing oxidative stress, increasing adiponectin levels and/or increasing brain-derived neurotrophic factors. Examples of such disease and disorders, include but are not limited to, cystinosis, and fatty liver diseases.

34 Claims, 16 Drawing Sheets

C1 H&E

C2

C3

SUBSTITUTED AMINO-THIOL AND AMINO-DISULFIDE COMPOUNDS, AND USES THEREOF

CROSS REFERENCE TO RELATED APPLICATIONS

This application is a U.S. National Stage Application filed under 35 U.S.C. § 371 and claims the benefit of International Application No. PCT/US2020/025067 filed Mar. 26, 2020, which application claims priority of U.S. Provisional Application No. 62/823,892, filed Mar. 26, 2019, the disclosures of each of which are incorporated herein by reference in their entirety.

FIELD OF THE INVENTION

Disclosed herein are substituted amino-thiol and amino-disulfide bioprotective compounds, pharmaceutical compositions made thereof, and methods thereof including the treatment of any disease or disorder in a subject that can benefit from one or more of the bioprotective effects of the compounds, including but not limited to, binding of cystine, reducing oxidative stress, increasing adiponectin levels and/or increasing brain-derived neurotrophic factors. Examples of such disease and disorders, include but are not limited to, cystinosis, and fatty liver diseases including non-alcoholic steatohepatitis (NASH).

BACKGROUND

Cysteamine is an amino thiol with the chemical formula $HSCH_2CH_2NH_2$. Endogenously, cysteamine is derived from coenzyme A degradation, although its plasma concentrations are low. Most experience with cysteamine as a drug originates from the field of the orphan disease cystinosis, in which cysteamine is prescribed to decrease intra lysosomal cystine accumulation. However, over the years, the drug has been used for several other applications both in vitro and in vivo. Cystamine is an organic disulfide that is the oxidized and dimeric form of cysteamine. There are as yet no clinical uses/indications for cystamine.

Cysteamine is available for clinical use only in the bitartrate salt form (MW 217) and is marketed as prolonged-release (Procysbi™) and an immediate release (Cystagon™) form. These formulations cause GI symptoms, halitosis and body odor due to the large amount of systemically circulating free cysteamine which occurs following intestinal absorption. This free circulating cysteamine most likely undergoes metabolism in organs such as the liver to form DMS and other volatile sulfur containing metabolites.

SUMMARY

Cysteamine is an aminothiol agent which has a number of potential therapeutic effects. It is FDA approved for the treatment of the rare metabolic disorder Cystinosis in which lysosomal storage of the amino acid cystine occurs. Although cysteamine (given as bitartrate salt) is effective in cystinosis it is associated with adverse effects such as halitosis, body odor and GI symptoms. These effects contribute to non-compliance to therapy and rapid deterioration of disease state.

In comparison to cysteamine and cystamine the deuterated compounds of the disclosure are isotopically enriched with deuterium. The deuterated compounds of the disclosure have improved properties (e.g., ADME-PK) over the non-deuterated forms of the compounds that arise from the strategic deployment of the deuterium atom(s). These benefits include altered metabolism of the molecule which (1) prolongs the duration of action of the active drug and (2) alters the pathway of metabolism of cysteamine to less active or inactive metabolites (thereby diminishing the production of body odor and halitosis producing noxious and volatile agents such as dimethyl sulfide (DMS) and dimethyl disulfide). The compounds of the disclosure can be used to treat numerous diseases and can be administered orally as immediate-release or enteric-release or sustained-release formulations and also as inhaled/nebulized pulmonary delivery or intranasal delivery or transcutaneous delivery. It is expected that the compounds of the disclosure would have better patient compliance, and improved pharmacokinetics in comparison to currently approved formulations of cysteamine.

In a particular embodiment, the disclosure provides for a compound having the structure of Formula I or Formula II:

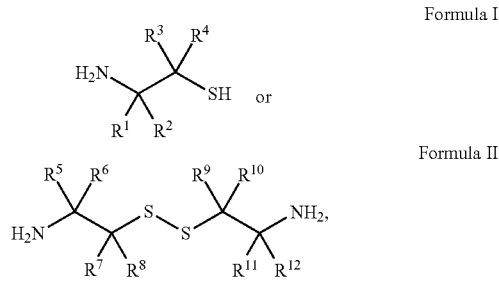

or a pharmaceutically acceptable salt, solvate or prodrug thereof, wherein: $R^1$-$R^{12}$ are independently selected from H or D; wherein at least one of $R^1$-$R^4$ is D, and wherein at least one of $R^5$-$R^{12}$ is D, with the proviso that the compound is not selected from the group consisting of:

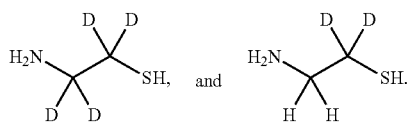

In another embodiment, at least one of $R^1$-$R^{12}$ independently has deuterium enrichment of no less than about 10%. In yet another embodiment, at least one of $R^1$-$R^{12}$ independently has deuterium enrichment of no less than about 50%. In a further embodiment, at least one of $R^1$-$R^{12}$ independently has deuterium enrichment of no less than about 90%. In yet a further embodiment, at least one of $R^1$-$R^{12}$ independently has deuterium enrichment of no less than about 98%. In a particular embodiment, the compound has a structural formula selected from the group consisting of:

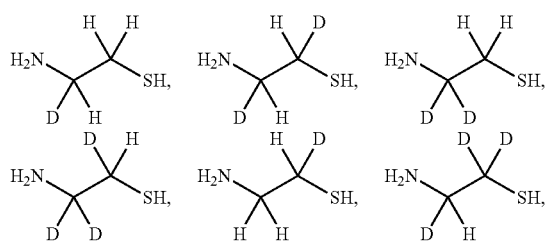

-continued
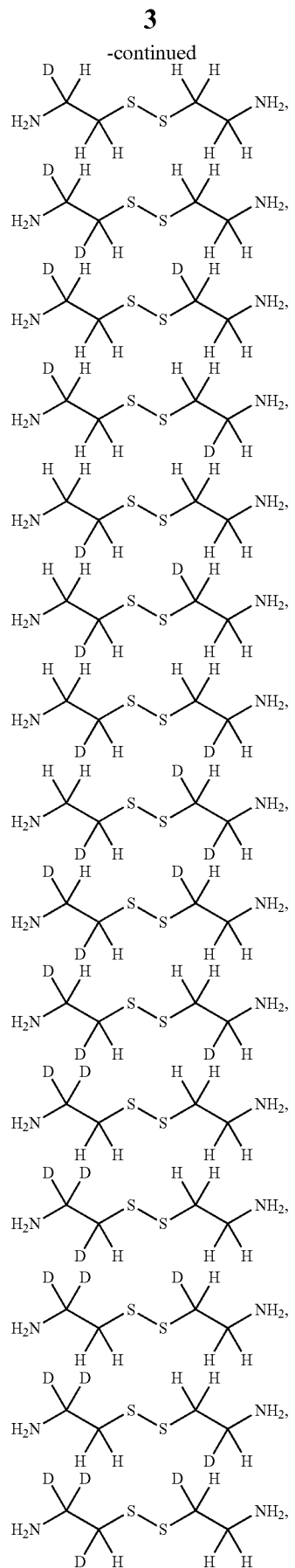
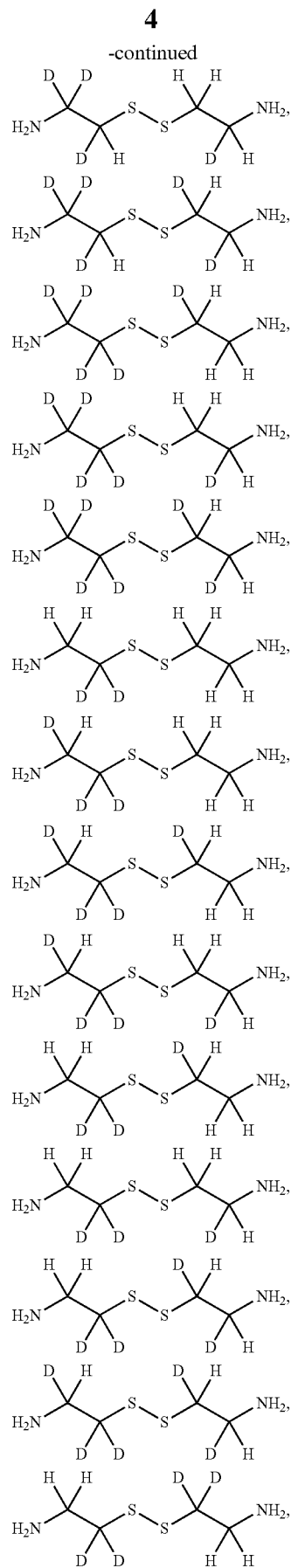

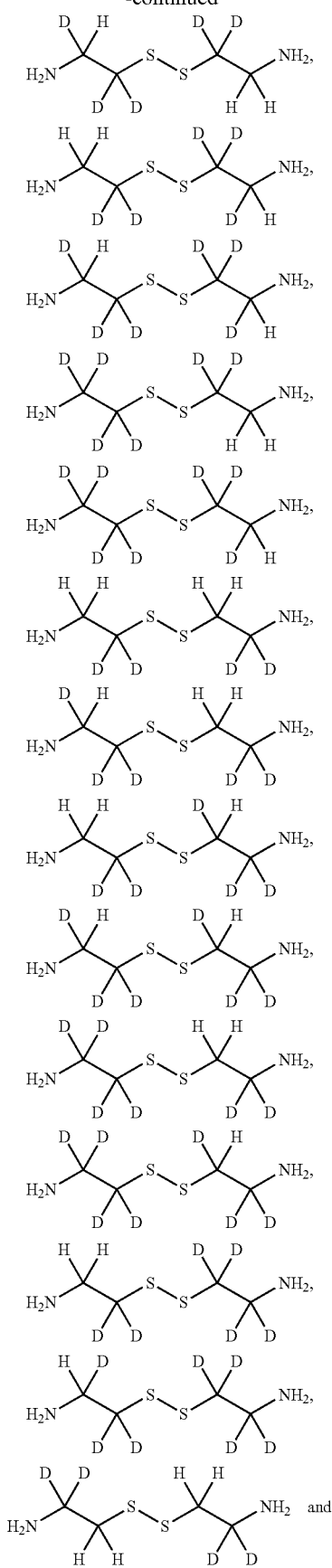

or a pharmaceutically acceptable salt, solvate, or prodrug thereof. In a certain embodiment, the compound has a structure of:

or a pharmaceutically acceptable salt, solvate, or prodrug thereof. In another embodiment, each position represented as D has deuterium enrichment of no less than about 10%. In yet another embodiment, each position represented as D has deuterium enrichment of no less than about 50%. In a further embodiment, each position represented as D has deuterium enrichment of no less than about 90%. In yet a further embodiment, each position represented as D has deuterium enrichment of no less than about 98%. In a certain embodiment, the compound is a pharmaceutically acceptable bitartrate salt form of the compound. In another embodiment, the compound in comparison to cysteamine or cystamine, exhibits at least one effect selected from the group consisting of: (a) decreased inter-individual variation in plasma levels of said compound or a metabolite thereof as compared to cysteamine or cystamine; (b) increased average plasma levels of said compound per dosage unit thereof as compared to cysteamine or cystamine; (c) decreased average plasma levels of at least one metabolite of said compound per dosage unit thereof as compared to cysteamine or cystamine; (d) increased average plasma levels of at least one metabolite of said compound per dosage unit thereof as compared to cysteamine or cystamine; and (e) an improved clinical effect during the treatment in the subject per dosage unit thereof as compared to cysteamine or cystamine. In yet another embodiment, the compound in comparison to cysteamine or cystamine exhibits at least two effects selected from the group consisting of: (a) decreased inter-individual variation in plasma levels of said compound or a metabolite thereof as compared to cysteamine or cystamine; (b) increased average plasma levels of said compound per dosage unit thereof as compared to cysteamine or cystamine; (c) decreased average plasma levels of at least one metabolite of said compound per dosage unit thereof as compared to cysteamine or cystamine; (d) increased average plasma levels of at least one metabolite of said compound per dosage unit thereof as compared to cysteamine or cystamine; and (e) an improved clinical effect during the treatment in the subject per dosage unit thereof as compared to cysteamine or cystamine. In yet another embodiment, the compound affects a decreased metabolism of the compound per dosage unit thereof by at least one polymorphically-expressed cytochrome $P_{450}$ isoform in a subject, as compared to cysteamine or cystamine. In a further embodiment, the cytochrome $P_{450}$ isoform is selected from the group consisting of CYP2C8, CYP2C9, CYP2C19, and CYP2D6. In another embodiment, the compound is characterized by decreased inhibition of at least one cytochrome $P_{450}$ isoform or monoamine oxidase isoform in the subject per dosage unit thereof as compared to cysteamine or cystamine. In yet another embodiment, the cytochrome $P_{450}$ isoform or monoamine oxidase isoform is selected from the group consisting of CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, CYP51, $MAO_A$ and $MAO_B$. In a certain embodiment, the compound reduces a deleterious change in a diagnostic hepatobiliary function endpoint as compared to cysteamine or cystamine. In a further embodiment, the diagnostic hepatobiliary function endpoint is selected from the group consisting of alanine aminotransferase ("ALT), serum glutamic-pyruvic transaminase ("SGPT"), aspartate aminotransferase ("AST," "SGOT"), ALT/AST ratios, serum aldolase, alkaline phosphatase (ALP), ammonia levels, bilirubin, gamma-glutamyl transpeptidase ("GGTP "Y-GTP "GGT), leucine aminopeptidase ("LAP), liver biopsy, liver ultrasonography, liver nuclear Scan, 5'-nucleotidase, and blood protein.

In a particular embodiment, the disclosure also provides for a pharmaceutical composition comprising a compound disclosed herein and a pharmaceutically acceptable carrier, diluent, and/or binder. In another embodiment, the pharmaceutical composition is formulated for oral delivery. In another embodiment, the pharmaceutical composition is in the form of granules, tablet, capsule, or caplet. In yet another embodiment, the pharmaceutical composition is formulated for delayed release. In a further embodiment, the pharmaceutical composition comprises an enteric coating. In yet a further embodiment, the pharmaceutical composition comprises colloidal silicon dioxide, croscarmellose sodium, D&C yellow no. 10 aluminum lake, FD&C blue no. 1 aluminum lake, FD&C blue no. 2 aluminum lake, FD&C red no. 40 aluminum lake, gelatin, magnesium stearate, microcrystalline cellulose, pharmaceutical glaze, pregelatinized starch, silicon dioxide, sodium lauryl sulfate, synthetic black iron oxide and/or titanium dioxide. In an alternate embodiment, the pharmaceutical composition comprises microcrystalline cellulose, Eudragit® L 30 D-55, Hypromellose, talc, triethyl citrate, sodium lauryl sulfate, purified water, gelatin, titanium dioxide, blue ink and/or white ink. In yet another embodiment, the pharmaceutical composition comprises: (i) a core particle comprising a mixture of the compound of claim 12 and a binder, and (ii) an enteric membrane surrounding the core particle; wherein the particles have a distribution of particle sizes in a range of about 0.7 mm to about 2.8 mm; wherein the enteric membrane begins to dissolve within a pH range of about 4.5 to about 6.5; wherein the enteric membrane is present in an amount in a range of about 25% to about 35% by weight, based on the weight of the core particles. In an alternate embodiment, the pharmaceutical composition comprises: (i) a core tablet comprising a mixture of the compound of claim 12 and a binder, and (ii) an enteric membrane surrounding the tablet, wherein the thickness of the enteric coating increases from 60 μm to 130 μm relative to the compound's base dose from 50 mg to 300 mg, and/or wherein the enteric coating is present in an amount in a range of about 9 to about 15% by weight of the core tablet.

In a particular embodiment, the disclosure provides a method of treating a subject suffering from a disease or disorder in need of treatment thereof, comprising administering to the subject a therapeutically effective amount of a compound having the structure of Formula I or Formula II:

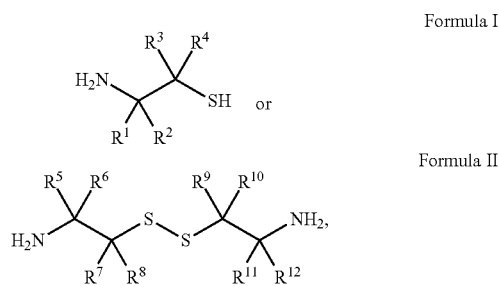

or a pharmaceutically acceptable salt, solvate or prodrug thereof, wherein: $R^1$-$R^{12}$ are independently selected from H or D; wherein at least one of $R^1$-$R^4$ is D, and wherein at least one of $R^5$-$R^{12}$ is D. In another embodiment, at least one of $R^1$-$R^{12}$ of the compound independently has deuterium enrichment of no less than about 10%. In yet another embodiment, at least one of $R^1$-$R^{12}$ of the compound independently has deuterium enrichment of no less than about 50%. In a further embodiment, at least one of $R^1$-$R^{12}$ of the compound independently has deuterium enrichment of no less than about 90%. In yet another embodiment, at least one of $R^1$-$R^{12}$ of the compound independently has deuterium enrichment of no less than about 98%. In a further embodiment, the compound has a structural formula selected from the group consisting of:

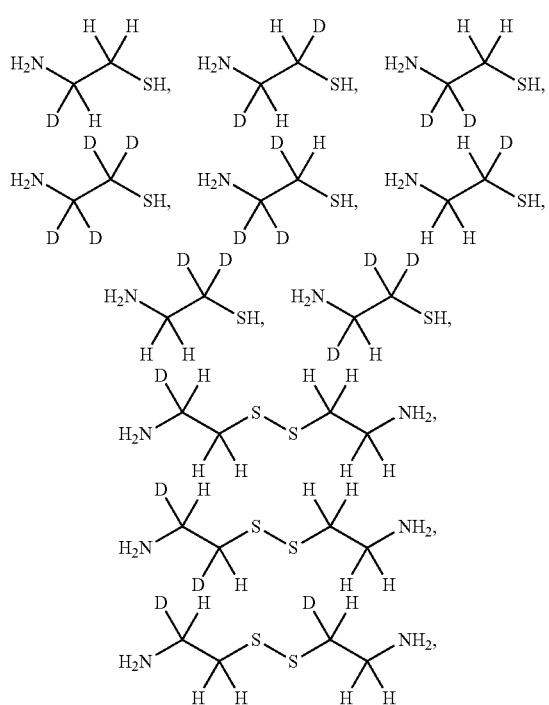

-continued
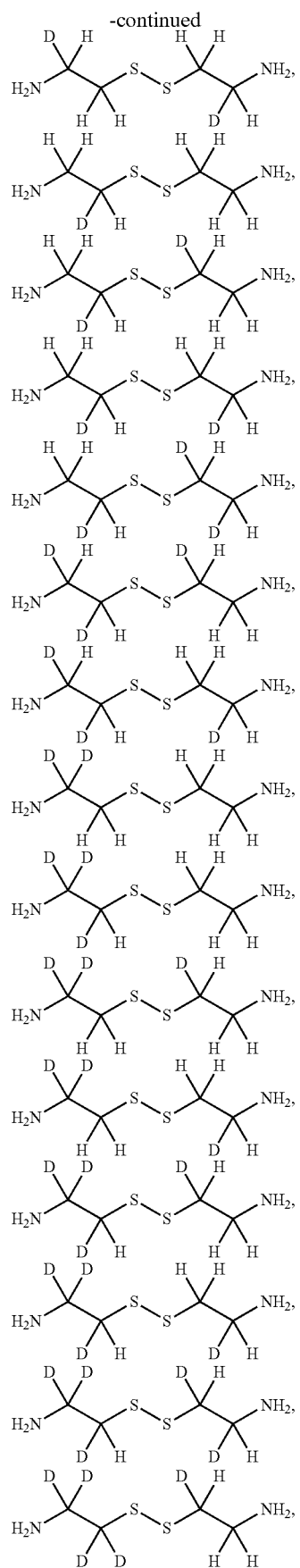
-continued
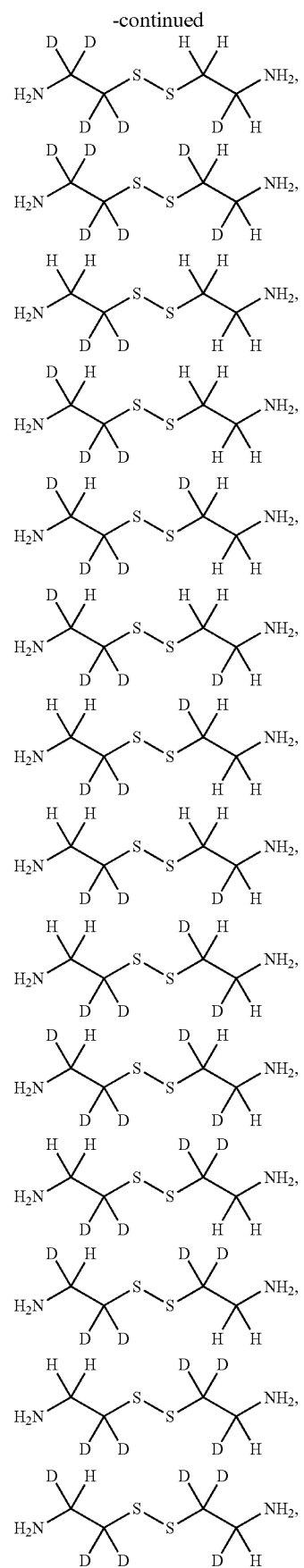

-continued

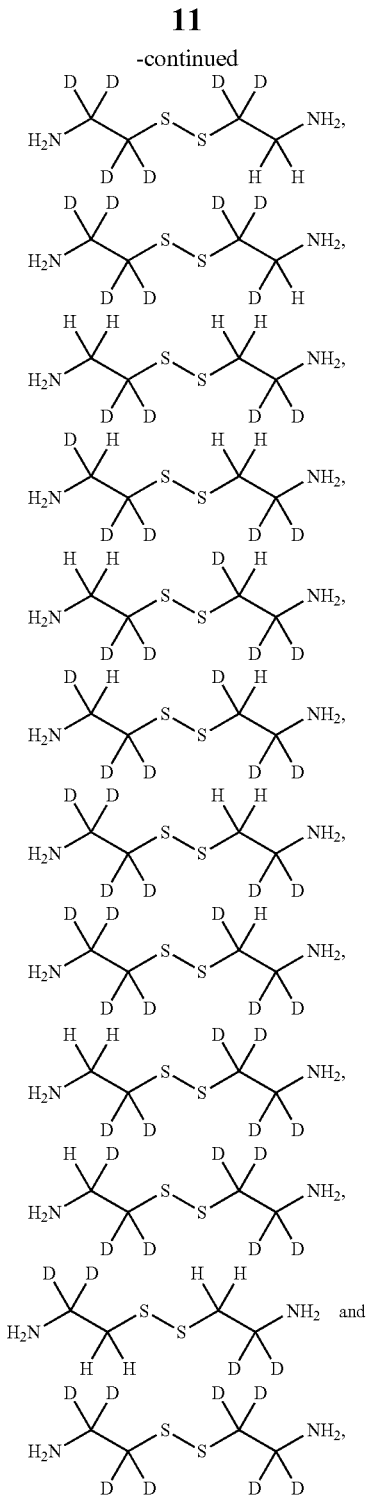

or a pharmaceutically acceptable salt, solvate, or prodrug thereof. In a further embodiment, the compound has a structure selected from:

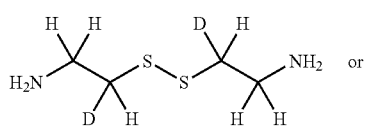

-continued

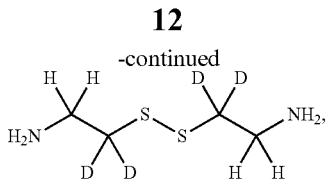

or a pharmaceutically acceptable salt, solvate, or prodrug thereof. In another embodiment, each position represented as D has deuterium enrichment of no less than about 10%. In yet another embodiment, each position represented as D has deuterium enrichment of no less than about 50%. In a further embodiment, each position represented as D has deuterium enrichment of no less than about 90%. In yet a further embodiment, each position represented as D has deuterium enrichment of no less than about 98%. In a certain embodiment, the compound is a pharmaceutically acceptable bitartrate salt form of the compound. In another embodiment, the subject suffers from cystinosis. In an alternate embodiment, the disease or disorder is a fatty liver disease. In a further embodiment, the fatty liver disease is selected from the group consisting of non-alcoholic fatty liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy. In a particular embodiment, the fatty liver disease is NASH. In a further embodiment, a method of the disclosure further comprises measuring one or more markers of liver function selected from the group consisting of alanine aminotransferase (ALT), alkaline phosphatase (ALP), aspartate aminotransferase (AST), gamma-glutamyl transpeptidase (GGT) and triglycerides. In yet a further embodiment, an ALT level of about 60-150 units/liter is indicative of fatty liver disease. In another embodiment, an ALP level of about 150-250 units/liter is indicative of fatty liver disease. In yet another embodiment, an AST level of about 40-100 units/liter is indicative of fatty liver disease. In a further embodiment, a GGT level of 50-100 units/liter is indicative of fatty liver disease. In yet a further embodiment, a triglyceride level above 150 mg/dL and/or high LDL level is indicative of fatty liver disease. The disclosure also provides a method of reducing fibrosis or fat content or fat accumulation in a liver of a subject associated with non-alcoholic fatty liver disease (NAFLD) comprising administering a compound of the disclosure or a pharmaceutical composition thereof to the subject in need thereof.

DETAILED DESCRIPTION

Figure 1:
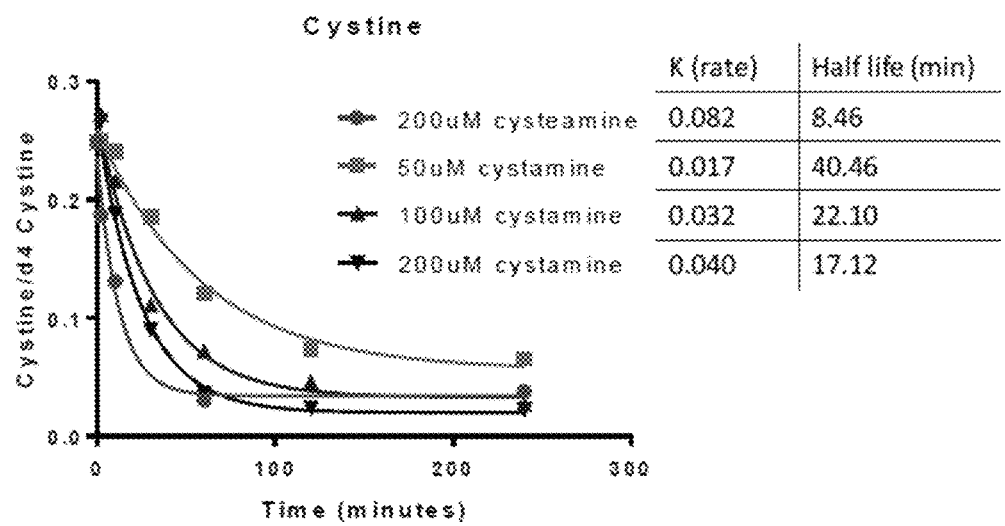
FIG. 1 demonstrates that 50 µM, 100 µM, and 200 µM cystamine is effective in reducing intracellular cystine levels in a dose-response fashion. Cysteamine 200 µM is effective and more rapid in its response time than 50 uM cystamine and 100 uM cystamine in particular.
Figure 2A:
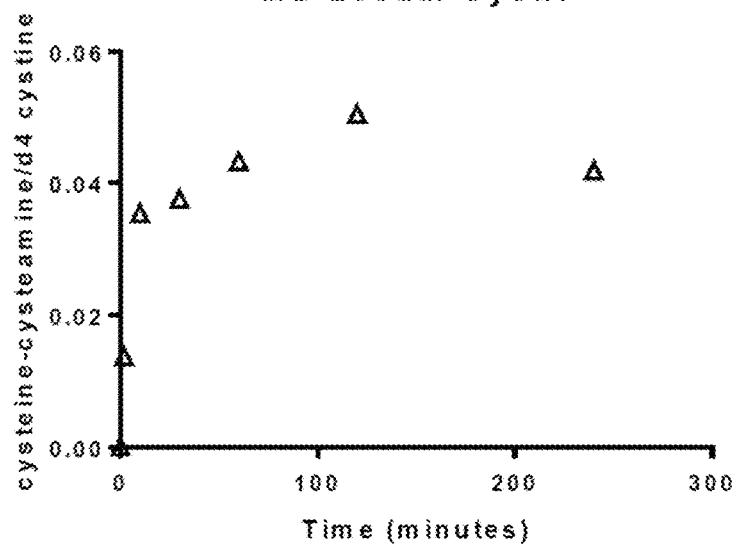
FIG. 2A-B shows that the conversion of intracellular cystine to mixed disulfide (MD) of cysteine-cysteamine is delayed when cystinotic fibroblasts are cultured in the presence of (A) cystamine (50, 100, and 200 µM) compared with (B) cysteamine (200 µM). This is most likely due to the delay in intracellular reduction of cystamine and hence the availability of cysteamine (active form).
Figure 2B:
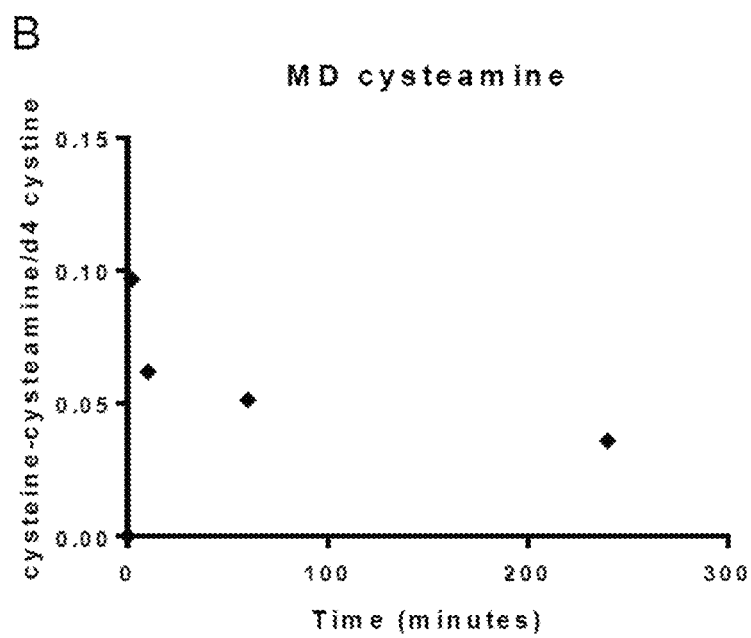
Figure 3:
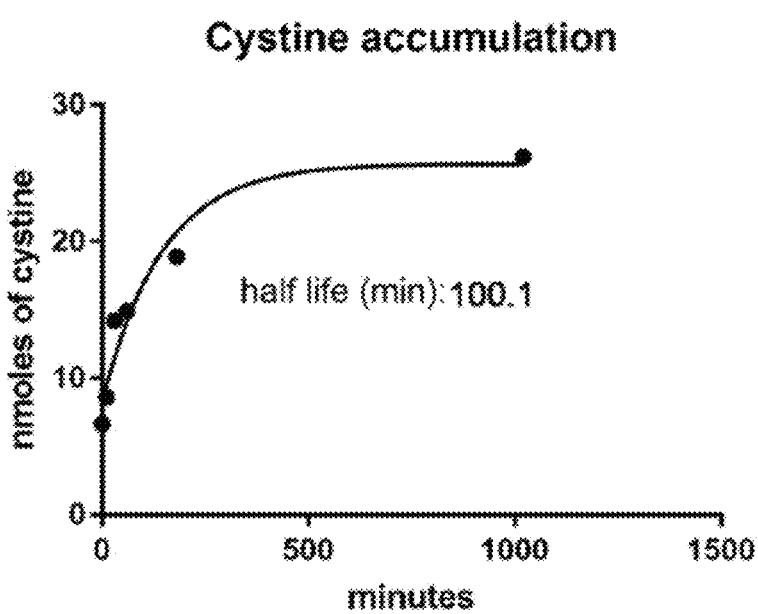
FIG. 3 shows intracellular re-accumulation of cystine over time. The figure shows the rise of intracellular cystine levels after the cystinotic fibroblast cell plates were washed following a 3 h incubation with 100 μM cystamine. The washed cells were then incubated in cystamine-free media for 10, 30, 60, 180 mins and 17 h. Cystine levels were extracted from 2 cystinotic fibroblast plates that were not exposed to cystamine and their cystine levels were identical to the 17 h cystine measurement. It is unclear exactly when the plateau was first achieved.
Figure 4A:
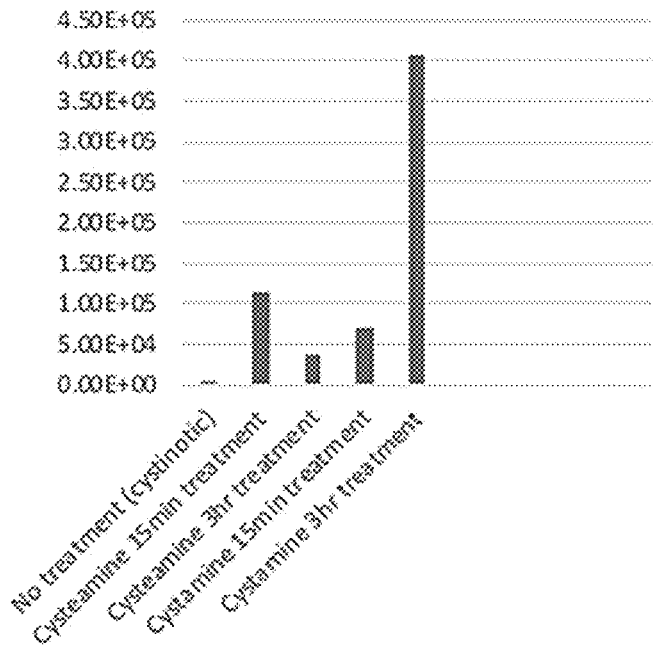
FIG. 4A-D shows intracellular levels of (A) cysteamine, (B) cystamine, (C) cystine, and (D) cysteine in cystinotic fibroblasts in media continuously exposed to cysteamine 100 μM. NEM cysteamine was measured to prevent the oxidation of cysteamine to cystamine resulting in incorrect readings. The 3 h cystamine incubation shows a very large amount of cysteamine (shown as NEM bound). Accordingly, cystamine is being reduced well, but slowly, as the 15 min point shows much less cysteamine comparatively. It is expected that the low amount of cysteamine at 15 min to be bound to cysteine through a mixed disulfide though, since cystine still looks high at this timepoint. The cystine levels remained low in both cases.
Figure 4B:
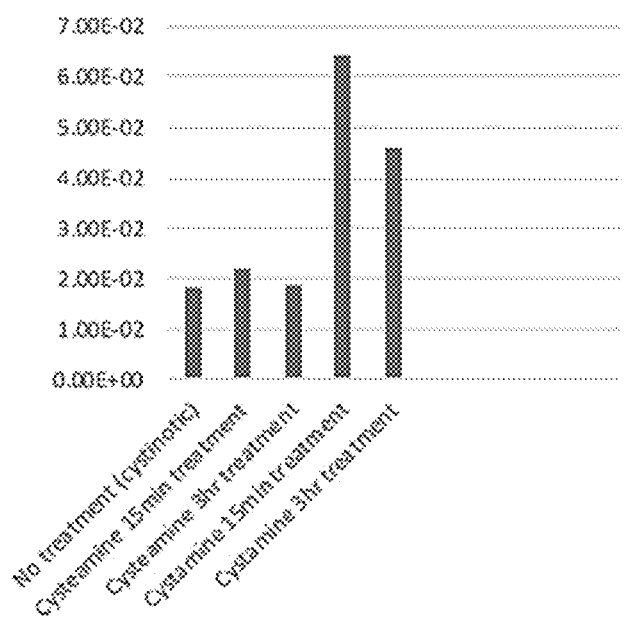
Figure 4C:
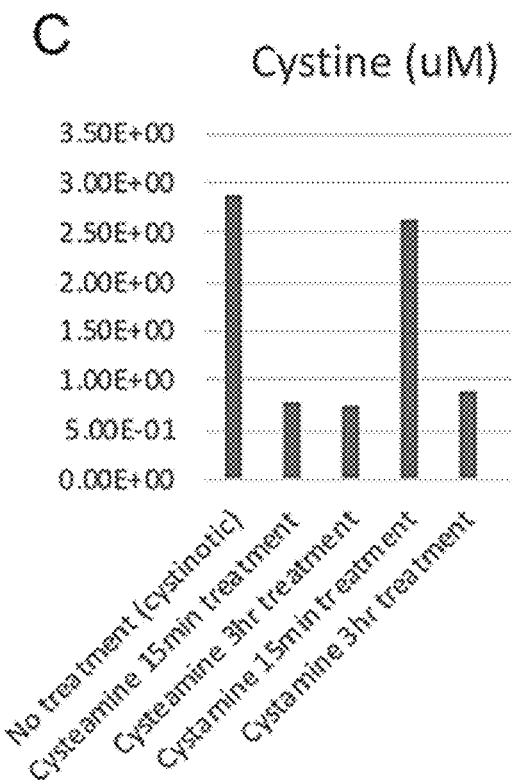
Figure 4D:
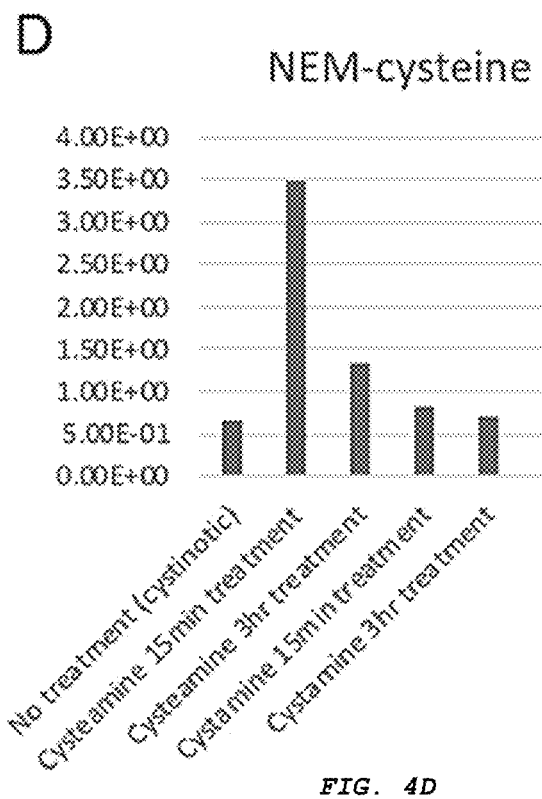
Figure 5A:
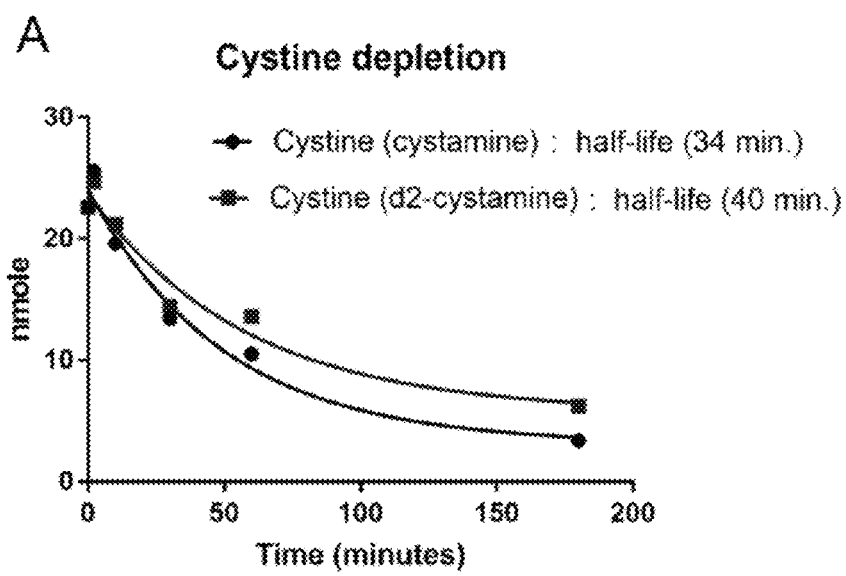
FIG. 5A-C compares cystine depletion (measuring cysteamine in the form of NEM-cysteamine, and also cystamine) in a time course of drug exposure in cystinotic fibroblasts, using either a 100 uM cystamine or 100 uM $d_2$-cystamine exposure. (A-C) The rate of intracellular cystine depletion was slower for 100 uM $d_2$-cystamine compared with 100 uM cystamine. This most likely correlates with the rate/degree of reduction of cystamine to NEM-cysteamine which seems faster/higher with cystamine versus $d_2$-cystamine especially in the first 10-15 minutes. This erratic and high level of cysteamine may correlate with greater production of noxious and volatile metabolites.
Figure 5B:
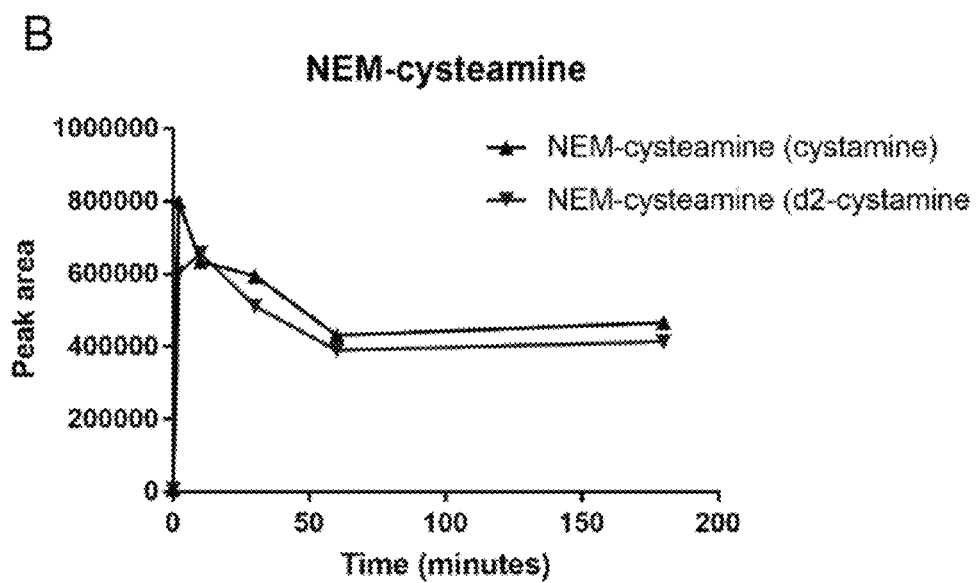
Figure 5C:
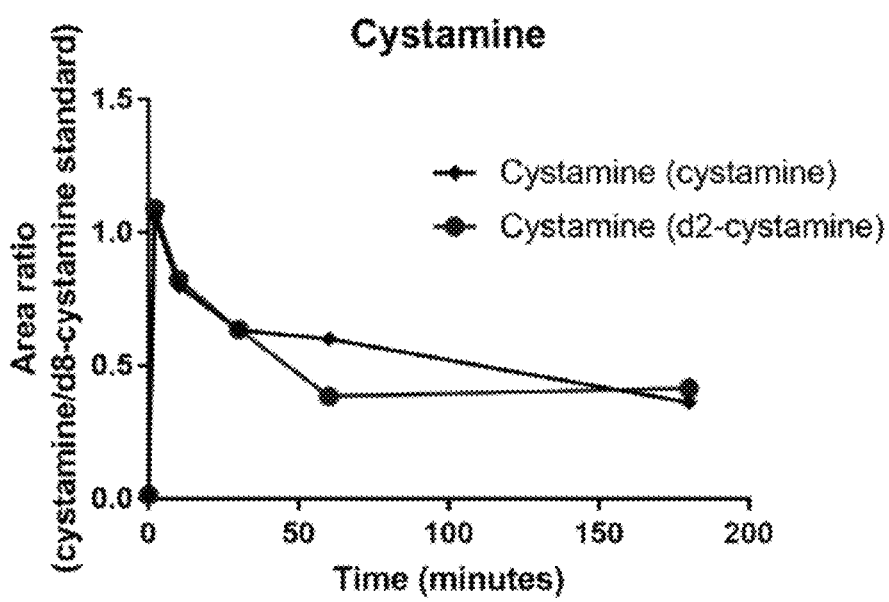

As used herein and in the appended claims, the singular forms "a," "an" and "the" include plural referents unless the context clearly dictates otherwise. Thus, for example, reference to "a derivative" includes a plurality of such derivatives and reference to "a subject" includes reference to one or more subjects and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Examination of the use of cysteamine in patients with cystinosis indicated that control of the disease (reduction of WBC cystine levels) correlated well with AUC and Cmax of the drug cysteamine. This was shown by Dohil et al. (J Pediatr 2006: 148:764-9). The present disclosure shows that deuterated-cysteamine and/or cystamine is/are more robust/stable and is likely to deliver more drug to the site of target cell action. The data presented here show that deuterated compounds of the disclosure have an effect on the CDAHFD induced mouse model for NASH by significantly reducing ALT, hepatic fibrosis, hepatic inflammation and also pericentric hepatic steatosis just after 2 weeks of treatment. For example, the deuterated compounds disclosed herein maintain the beneficial aspects of the corresponding non-isotopically enriched molecules while substantially increasing the maximum tolerated dose, decreasing toxicity, increasing the half-life, lowering the maximum plasma concentration (Cmax) of the minimum efficacious dose (MED), lowering the efficacious dose and thus decreasing the non-mechanism-related toxicity, and/or lowering the probability of drug-drug interactions. The deuterated compounds of the disclosure shows improved AUC. For example, the AUC measurements for cystamine D4-derived D2-cysteamine were much higher than cystamine derived cysteamine and also D2-cystamine-derived D1-cysteamine. The hepatocyte elimination studies, described below, show that D4-cystamine is the most stable of the dimeric compounds. The data further show that D4-cystamine results in a higher AUC and Cmax (for its D2-cysteamine monomer form) compared with D2-cystamine and cystamine and also has a reduced rate of elimination in the hepatocyte elimination studies. Moreover, the data show that the deuterated compounds of the disclosure reduce macrophage and microglial cells in liver tissue having a fatty liver phenotype. For example, the data below show there was a statistically significant reduction ($p<0.0001$) in the number of CD11b positive cells in liver tissue in mice treated with D2 and D4-cystamine compared with the control group.

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

The terms "active ingredient", "active compound", and "active Substance" refer to a compound, which is administered, alone or in combination with one or more pharmaceutically acceptable excipients or carriers, to a subject for treating, preventing, or ameliorating one or more symptoms of a disorder.

In representing a range of positions on a structure, the notation "from $R^x$ to $R^{xx}$" or "$R^x$—$R^{xx}$" may be used, wherein X and XX represent numbers. Then unless otherwise specified, this notation is intended to include not only the numbers represented by X and XX themselves, but all the numbered positions that are bounded by X and XX. For example, "from $R^1$ to $R^4$" or "$R^1$-$R^4$" would, unless otherwise specified, be equivalent to $R^1$, $R^2$, $R^3$, and $R^4$.

The term "combination therapy' means the administration of two or more therapeutic agents to treat a therapeutic disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the disorders described herein.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials are about 0.0156%. The deuterium enrichment can be determined using conventional analytical methods known to one of ordinary skill in the art, including mass spectrometry and nuclear magnetic resonance spectroscopy.

The term "is/are deuterium", when used to describe a given position in a molecule such as R—R or the symbol "D." when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "disorder" as used herein is intended to be generally synonymous, and is used interchangeably with, the terms "disease", "syndrome", and "condition" (as in medical condition), in that all reflect an abnormal condition of the human or animal body or of one of its parts that impairs normal functioning, is typically manifested by distinguishing signs and Symptoms.

The terms "drug" and "therapeutic agent" refer to a compound, or a pharmaceutical composition thereof, which is administered to a subject for treating, preventing, or ameliorating one or more symptoms of a disease or disorder.

The term "non-deuterated" when used to describe a compound refers to a compound that has not been manufactured to increase the level of deuteration beyond what may naturally occur without the process of active deuteration. In some instances a non-deuterated molecule lacks any deuterated atoms.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

The term "non-release controlling excipient" refers to an excipient whose primary function does not include modifying the duration or place of release of the active substance from a dosage form as compared with a conventional immediate release dosage form.

The term "pharmaceutically acceptable carrier, "pharmaceutically acceptable excipient", "physiologically acceptable carrier", or "physiologically acceptable excipient" refers to a pharmaceutically-acceptable material, composition, or vehicle, such as a liquid or Solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. See, Remington. The Science and Practice of Pharmacy, 21st Edition; Lippincott Williams & Wilkins: Philadelphia, Pa., 2005, Handbook of Pharmaceutical Excipients, 5th Edition; Rowe et al., Eds. The Pharmaceutical Press and the American Pharmaceutical Association:2005; and Handbook of Pharmaceutical Additives, 3rd Edition; Ash and Ash Eds. Gower Publishing Company: 2007; Pharmaceutical Preformulation and Formulation, Gibson Ed., CRC Press LLC: Boca Raton, Fla., 2004).

The compounds disclosed herein can and do exist as therapeutically acceptable salts. The term "pharmaceutically acceptable salt", as used herein, represents salts or Zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts. For a more complete discussion of the preparation and selection of salts, refer to "Handbook of Pharmaceutical Salts, Properties, and Use." Stah and Wermuth, Ed. (Wiley-VCH and VHCA, Zurich, 2002) and Berge et al., *J. Pharm. Sci.* 1977, 66, 1-19.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-Sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, C—OXO-glutaric acid, glycolic acid, hippuric acid, hydrobromic acid, hydrochloric acid, hydroiodic acid, (+)-L-lactic acid, (t)-DL-lactic acid, lactobionic acid, lauric acid, maleic acid, (−)-L-malic acid, malonic acid, (+)-DL mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The terms "prevent", "preventing", and "prevention" refer to a method of delaying or precluding the onset of a disorder, and/or its attendant symptoms, barring a subject from acquiring a disorder or reducing a subject's risk of acquiring a disorder.

The term "prodrug" refers to a compound functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, Progress in Drug Research 1962, 4, 221-294; Morozowich et al. in "Design of Biopharmaceutical Properties through Prodrugs and Analogs. Roche Ed., APHA Acad. Pharm. Sci. 1977: "Bioreversible Carriers in Drug in Drug Design, Theory and Application." Roche Ed., APHA Acad. Pharm. Sci. 1987: "Design of Prodrugs." Bundgaard, Elsevier, 1985; Wang et al., *Curr. Pharm. Design* 1999, 5, 265-287: Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems." Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209: Browne, *Clin. Neuropharmacol.* 1997, 20, 1-12; Bundgaard, *Arch. Pharm. Chem.* 1979, 86, 1-39: Bundgaard, *Controlled Drug Delivery* 1987, 17, 179-96: Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877: Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45,866-94: Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

The term "release controlling excipient" refers to an excipient whose primary function is to modify the duration or place of release of the active substance from a dosage form as compared with a conventional immediate release dosage form.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, Swine (e.g., pig, miniature pig), equine, canine, feline, and the like. The terms "subject' and "patient" are used interchangeably herein in reference, for example, to a mammalian subject, such as a human patient.

The term "substantially" as used herein refers to a majority of, or mostly, as in at least about 51%, 60%, 70%, 80%, 90%, 95%, 96%, 97%, 98%, 99%, 99.5%, 99.9%, 99.99%, or at least about 99.999% or more.

The term "therapeutically acceptable" refers to those compounds (or salts, prodrugs, tautomers, Zwitterionic forms, etc.) which are suitable for use in contact with the tissues of patients without excessive toxicity, irritation, allergic response, immunogenicity, are commensurate with a reasonable benefit/risk ratio, and are effective for their intended use.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, Veterinarian, medical doctor, or clinician.

The terms "treat", "treating", and "treatment" are meant to include alleviating or abrogating a disorder or one or more of the symptoms associated with a disorder; or alleviating or eradicating the cause(s) of the disorder itself. As used herein, reference to "treatment of a disorder" is intended to include prevention.

Cysteamine is a small aminothiol molecule that is easily transported across cellular membranes. Cysteamine markedly reduces intralysosomal cysteine accumulation and is currently approved as a treatment for cystinosis. Cysteamine can increase the cellular thiol and free thiol tripeptide glutathione pool, and thus modulate reactive oxygen species (ROS) scavenging, and decreased lipoperoxidation and glutathione peroxidase activity. Furthermore, cysteamine also increases adiponectin levels.

Cysteamine is an attractive candidate for the treatment of fatty liver disease including NASH, as it reacts with cystine to produce cysteine, which can further be metabolized into glutathione, a potent endogenous antioxidant. Cysteamine is a precursor to the protein glutathione (GSH) precursor, and is currently FDA approved for use in the treatment of cystinosis, an intra-lysosomal cystine storage disorder. In cystinosis, cysteamine acts by converting cystine to cysteine and cysteine-cysteamine mixed disulfide which are then both able to leave the lysosome through the cysteine and lysine transporters respectively (Gahl et al., N Engl J Med 2002; 347(2):111-21). Within the cytosol the mixed disulfide can be reduced by its reaction with glutathione and the cysteine released can be used for further GSH syntheses. The synthesis of GSH from cysteine is catalyzed by two enzymes, gamma-glutamylcysteine synthetase and GSH synthetase. This pathway occurs in almost all cell types, with the liver being the major producer and exporter of GSH. The reduced cysteine-cysteamine mixed disulfide will also release cysteamine, which, in theory is then able to re-enter the lysosome, bind more cystine and repeat the process (Dohil et al., J Pediatr 2006; 148(6):764-9). In a recent study in children with cystinosis, enteral administration of cysteamine resulted in increased cysteamine absorption, which subsequently caused prolonged efficacy in the lowering of leukocyte cystine levels (Dohil et al., J Pediatr 2006; 148(6):764-9). This may have been due to "re-cycling" of cysteamine when adequate amounts of drug reached the lysosome. If cysteamine acts in this fashion, then GSH production may also be significantly enhanced.

Cysteamine is a potent gastric acid-secretagogue that has been used in laboratory animals to induce duodenal ulceration. Studies in humans and animals have shown that cysteamine-induced gastric acid hypersecretion is most likely mediated through hypergastrinemia. In previous studies performed in children with cystinosis who suffered regular upper gastrointestinal symptoms, a single oral dose of cysteamine (11-23 mg/kg) was shown to cause hypergastrinemia and a 2 to 3-fold rise in gastric acid-hypersecretion, and a 50% rise in serum gastrin levels. Symptoms suffered by these individuals included abdominal pain, heartburn, nausea, vomiting, and anorexia. U.S. patent application Ser. No. 11/990,869 and published International Publication No. WO 2007/089670, both claiming priority to U.S. Provisional Patent application No. 60/762,715, filed Jan. 26, 2006, (all of which are incorporated by reference herein in their entirety) showed that cysteamine induced hypergastrinemia arises, in part, as a local effect on the gastric antral-predominant G-cells in susceptible individuals. The data also suggest that this is also a systemic effect of gastrin release by cysteamine. Depending on the route of administration, plasma gastrin levels usually peak after intragastric delivery within 30 minutes whereas the plasma cysteamine levels peak later.

In addition, sulfhydryl (SH) compounds such as cysteamine, cystamine, and glutathione are among the most important and active intracellular antioxidants. Cysteamine protects animals against bone marrow and gastrointestinal radiation syndromes. The rationale for the importance of SH compounds is further supported by observations in mitotic cells. These are the most sensitive to radiation injury in terms of cell reproductive death and are noted to have the lowest level of SH compounds. Conversely, S-phase cells, which are the most resistant to radiation injury using the same criteria, have demonstrated the highest levels of inherent SH compounds. In addition, when mitotic cells were treated with cysteamine, they became very resistant to radiation. It has also been noted that cysteamine may directly protect cells against induced mutations. The protection is thought to result from scavenging of free radicals, either directly or via release of protein-bound GSH. An enzyme that liberates cysteamine from coenzyme A has been reported in avian liver and hog kidney. Recently, studies have appeared demonstrating a protective effect of cysteamine against the hepatotoxic agents acetaminophen, bromobenzene, and phalloidine.

Cystamine, in addition, to its role as a radioprotectant, has been found to alleviate tremors and prolong life in mice with the gene mutation for Huntington's disease (HD). The drug may work by increasing the activity of proteins that protect nerve cells, or neurons, from degeneration. Cystamine appears to inactivate an enzyme called transglutaminase and thus results in a reduction of huntingtin protein (Nature Medicine 8, 143-149, 2002). In addition, cystamine was found to increase the levels of certain neuroprotective proteins. However, due to the current methods and formulation of delivery of cystamine, degradation and poor uptake require excessive dosing.

At present, cysteamine is FDA approved only for the treatment of cystinosis. Patients with cystinosis are normally required to take cysteamine every 6 hours or use an enteric form of cysteamine (PROCYSBI®) every 12 hours. Subjects with cystinosis are required to ingest oral cysteamine (CYSTAGON®) every 6 hours day and night or use an enteric form of cysteamine (PROCYSBI®) every 12 hours. When taken regularly, cysteamine can deplete intracellular cystine by up to 90% (as measured in circulating white blood cells), and reduces the rate of progression to kidney failure/transplantation and also to obviate the need for thyroid replacement therapy. Because of the difficulty in taking CYSTAGON®, reducing the required dosing improves the adherence to therapeutic regimen. International Publication No. WO 2007/089670 demonstrates that delivery of cysteamine to the small intestine reduces gastric distress and ulceration, increases $C_{max}$ and increases AUC. Delivery of cysteamine into the small intestine is useful due to improved absorption rates from the small intestine, and/or less cysteamine undergoing hepatic first pass elimination when absorbed through the small intestine. A decrease in leukocyte cystine was observed within an hour of treatment.

A pilot trial by Dohil et al. in 11 children with biopsy-confirmed non-alcoholic fatty liver disease (NAFLD) received enteric-coated (EC) cysteamine bitartrate orally for 24 weeks. This therapy resulted in statistically significant reductions in mean serum levels of alanine aminotransferase (ALT), aspartate aminotransferase (AST), total adiponectin, leptin, and cytokeratin-18 fragments, but without a concomitant reduction in body mass index. Seven out of 11 subjects reached the primary endpoints (of at least 50% reduction in ALT). The reduction in mean ALT and AST levels persisted 16 weeks after treatment ended.

In order to eliminate foreign substances such as therapeutic agents, the animal body expresses various enzymes, such as the cytochrome P450 enzymes (CYPs), esterases, proteases, reductases, dehydrogenases, and monoamine oxidases, to react with and convert these foreign substances to more polar intermediates or metabolites for renal excretion. Such metabolic reactions frequently involve the oxidation of a carbon-hydrogen (C—H) bond to either a carbon-oxygen (C—O) or a carbon-carbon (C—C) JU-bond. The resultant metabolites may be stable or unstable under physiological conditions, and can have substantially different pharmacokinetic, pharmacodynamic, and acute and long-term toxicity profiles relative to the parent compounds. For most drugs, such oxidations are generally rapid and ultimately lead to administration of multiple or high daily doses.

The relationship between the activation energy and the rate of reaction may be quantified by the Arrhenius equation, $k=Ae-E_a/RT$. The Arrhenius equation states that, at a given temperature, the rate of a chemical reaction depends exponentially on the activation energy ($E_a$).

The transition state in a reaction is a short-lived state along the reaction pathway during which the original bonds have stretched to their limit. By definition, the activation energy $E_a$ for a reaction is the energy required to reach the transition state of that reaction. Once the transition state is reached, the molecules can either revert to the original reactants, or form new bonds giving rise to reaction products. A catalyst facilitates a reaction process by lowering the activation energy leading to a transition state. Enzymes are examples of biological catalysts.

Carbon-hydrogen bond strength is directly proportional to the absolute value of the ground-state vibrational energy of the bond. This vibrational energy depends on the mass of the atoms that form the bond, and increases as the mass of one or both of the atoms making the bond increases. Since deuterium (D) has twice the mass of protium (H), a C-D bond is stronger than the corresponding C—H bond. If a C—H bond is broken during a rate-determining step in a chemical reaction (i.e., the step with the highest transition state energy), then substituting a deuterium for that protium will cause a decrease in the reaction rate. This phenomenon is known as the Deuterium Kinetic Isotope Effect (DKIE). The magnitude of the DKIE can be expressed as the ratio between the rates of a given reaction in which a C H bond is broken, and the same reaction where deuterium is substituted for protium. The DKIE can range from about 1 (no isotope effect) to very large numbers, such as 50 or more. Substitution of tritium for hydrogen results in yet a stronger bond than deuterium and gives numerically larger isotope effects.

Deuterium (D) is a stable and non-radioactive isotope of hydrogen which has approximately twice the mass of protium (H), the most common isotope of hydrogen. Deuterium oxide (DO) or deuterium dioxide ($D_2O$) or "heavy water" looks and tastes like $H_2O$, but has different physical properties. When pure $D_2O$ is given to rodents, it is readily absorbed. The quantity of deuterium required to induce toxicity is extremely high. When about 0-15% of the body water has been replaced by heavy water, animals are healthy but are unable to gain weight as fast as the control (untreated) group. When about 15-20% of the body water has been replaced with heavy water the animals become excitable. When about 20-25% of the body water has been replaced with heavy water, the animals become so excitable that they go into frequent convulsions when stimulated. Skin lesions, ulcers on the paws and muzzles, and necrosis of the tails appear. The animals also become very aggressive. When about 30% of the body water has been replaced with heavy water, the animals refuse to eat and become comatose. Their body weight drops sharply and their metabolic rates drop far below normal, with death occurring at about 30 to about 35% replacement with heavy water. The effects are reversible unless more than thirty percent of the previous body weight has been lost due to heavy water. Studies have also shown that the use of heavy water can delay the growth of cancer cells and enhance the cytotoxicity of certain antineoplastic agents.

Deuteration of pharmaceuticals to improve pharmacokinetics (PK), pharmacodynamics (PD), and toxicity profiles has been demonstrated previously with some classes of drugs. For example, the DKIE was used to decrease the hepatotoxicity of halothane, presumably by limiting the production of reactive species such as trifluoroacetylchloride. However, this method may not be applicable to all drug classes. For example, deuterium incorporation can lead to Metabolic Switching. Metabolic Switching occurs when xenogens, sequestered by Phase I enzymes, bind transiently and re-bind in a variety of conformations prior to the chemical reaction (e.g., oxidation). Metabolic switching is enabled by the relatively vast size of binding pockets in many Phase I enzymes and the promiscuous nature of many metabolic reactions. Metabolic switching can lead to different proportions of known metabolites as well as altogether new metabolites. This new metabolic profile may impart more or less toxicity. Such pitfalls are non-obvious and are not predictable a priori for any drug class.

Cysteamine is a small aminothiol molecule that is easily transported across cellular membranes. Cystamine is a small disulfide molecule that can be reduced into 2× cysteamine molecules. The carbon-hydrogen bonds of cysteamine and cystamine contain a naturally occurring distribution of hydrogen isotopes, namely H or protium (about 99.984.4%), H or deuterium (about 0.0156%), and H or tritium (in the range between about 0.5 and 67 tritium atoms per 10' protium atoms). Increased levels of deuterium incorporation may produce a detectable Kinetic Isotope Effect (KIE) that could affect the pharmacokinetic, pharmacologic and/or toxicologic profiles of tyrosine and/or tyramine in a Subject in comparison with tyrosine and/or tyramine having naturally occurring levels of deuterium.

Cysteamine is metabolized in vivo by first being converted to hypotaurine by the action of the cysteamine dioxygenase. Hypotaurine is then oxidized to taurine by the action of hypotaurine dehydrogenase. Cystamine is reduced in vivo into cysteamine and RS-cysteamine mixed disulphide by thiol-disulphide exchange. Cysteamine is then metabolized as above. The deuterated cysteamine and cystamine composition described and tested herein, were hypothesized to prevent or retard metabolism at these sites or other sites with other catabolic activities, such as retarding the conversion of cysteamine to hypotaurine. Other sites on the molecule may also undergo transformations leading to metabolites with as-yet unknown pharmacology/toxicology. Limiting the production of such metabolites has the potential to decrease the danger of the administration of such drugs and may even allow increased dosage and concomitant increased efficacy. All of these transformations, among other potential transformations, can occur through polymorphically-expressed enzymes, leading to interpatient variability. Further, it is quite typical for disorders ameliorated by the compositions and methods of the disclosure, such as NAFLD, NASH or cystinosis, to produce symptoms that are best medicated around the clock for extended periods of time.

For all of the foregoing reasons, a medicine with a longer half-life may result in greater efficacy and cost savings. Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. The deuteration approach has the potential to slow the metabolism and/or selectively shunt the metabolism of cysteamine and/or cystamine to more favorable enzymatic pathways. For example, it is expected that the deuteration approach presented herein could potentially prevent or reduce the production of odiferous cysteamine metabolites that can lead to patient noncompliance.

The disclosure provides bioprotective amino-thiol and amino-disulfide compounds and pharmaceutical compositions have been discovered, together with methods of synthesizing and using the compounds, including methods for the treatment of liver diseases and disorders in a patient by administering a compound of the disclosure.

In a particular embodiment, the disclosure provides for a compound having the structure of Formula I:

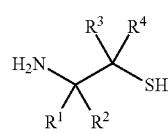

Formula I or a pharmaceutically acceptable salt, solvate, or prodrug thereof, wherein:

$R^1$-$R^4$ are independently selected from H or D; wherein at least one of $R^1$-$R^4$ is D. The disclosure demonstrates that deuterated forms of Formula I have characteristics that are different compared to non-deuterated forms of a compound of formula I (i.e., wherein R1-R4 do not contain any deuterated atoms). In one embodiment, the deuterated form of Formula I has a half-life that is longer than the half-life of a non-deuterated form. This is useful in the treatment of various disease and disorder to reduce dosing frequency and/or doses.

In another embodiment, the disclosure provides that the compound having the structure of Formula I does not have a structure selected from:

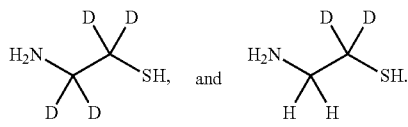 [SMILES: [2H]C([2H])(N)C([2H])([2H])S ; [2H]C([2H])(S)CN]

In a particular embodiment, the disclosure provides for a compound having the structure of Formula II:

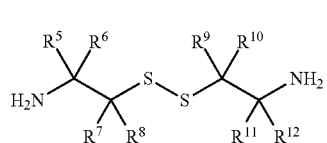

Formula II or a pharmaceutically acceptable salt, solvate, or prodrug thereof, wherein: $R^5$-$R^{12}$ are independently selected from H or D; wherein at least one of $R^5$-$R^{12}$ is D. As with formula I above, deuterated forms of Formula II also show longer half-life compared are to non-deuterated forms. As mentioned above, such increase half-lives can have effects on dosing and dosing frequencies.

In other embodiments, at least one of $R^1$-$R^{12}$ has deuterium enrichment of no less than about 10%, 50%, 90%, or 98%.

In a further embodiment, a compound disclosed herein is substantially a single enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, Substantially an individual diastereomer, or a mixture of about 90% or more by weight of an individual diastereomer and about 10% or less by weight of any other diastereomer.

In a certain embodiment, the compound of disclosure is selected from:
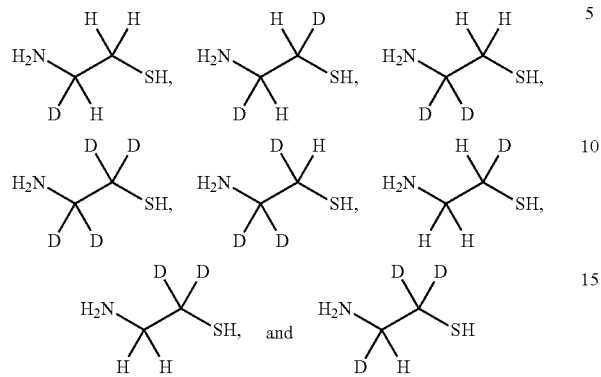
or a pharmaceutically acceptable salt, solvate, or prodrug thereof.
In another embodiment, the compound of disclosure is selected from:
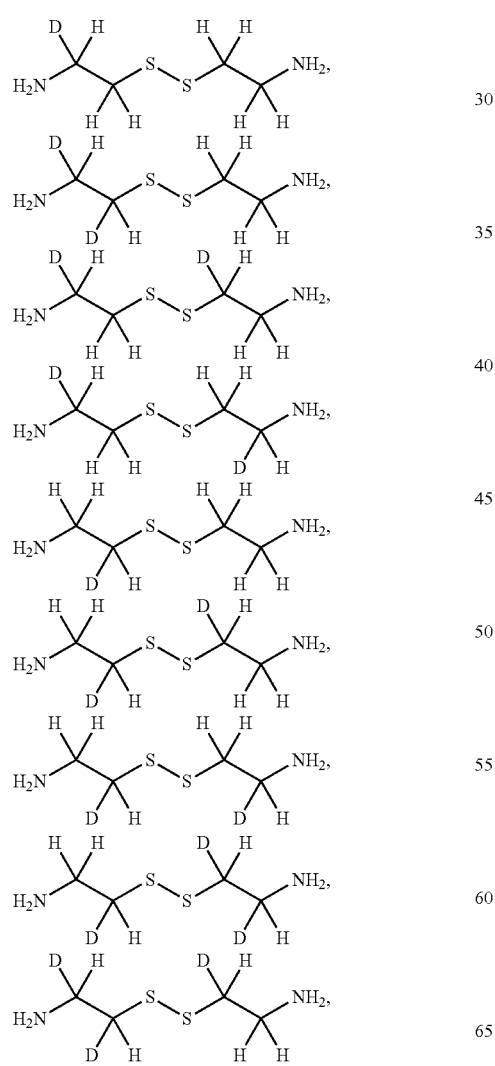
-continued
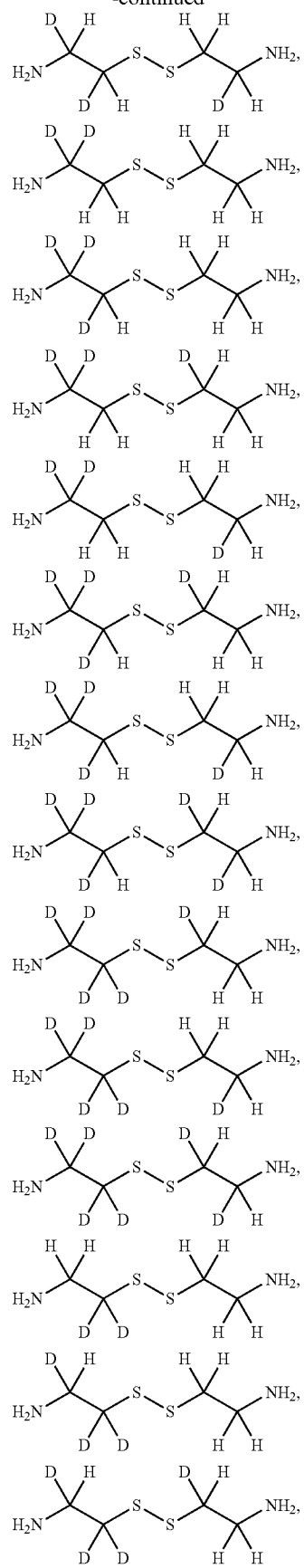

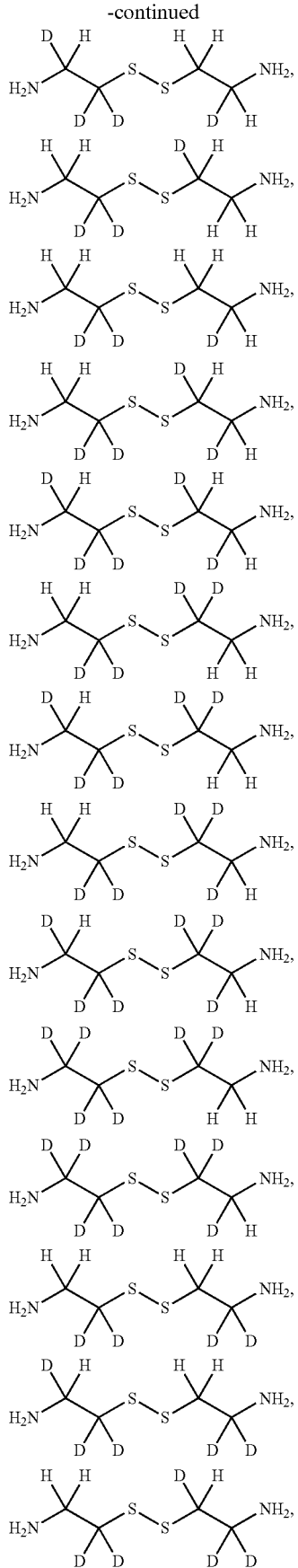

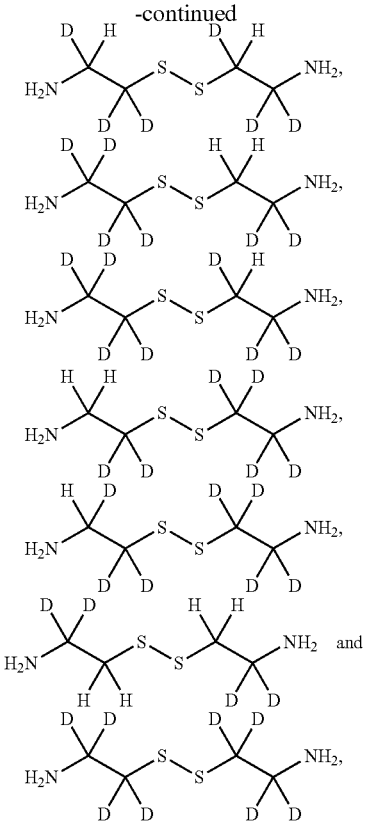

or a pharmaceutically acceptable salt, solvate, or prodrug thereof.

The disclosure is not limited with respect to a specific salt form of Formula I and/or II (e.g., the disclosure is not limited to any deuterated cysteamine or cystamine pharmaceutically acceptable salt). Further, the pharmaceutical compositions of the disclosure can contain a deuterated cysteamine or deuterated cystamine individually, or combination of cysteamine and cystamine, wherein either or both are deuterated. The active agents in the composition, i.e., deuterated cysteamine or deuterated cystamine, may be administered in the form of a pharmacologically acceptable salt, ester, amide, prodrug or analog or as a combination thereof. Salts, esters, amides, prodrugs and analogs of the active agents may be prepared using standard procedures known to those skilled in the art of synthetic organic chemistry and described, for example, by J. March, "Advanced Organic Chemistry: Reactions, Mechanisms and Structure," 4th Ed. (New York: Wiley-Interscience, 1992). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula R—COOH where R is alkyl, and typically is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature.

The compounds as disclosed herein may also contain less prevalent isotopes for other elements, including, but not limited to, $^{13}$C or $^{14}$C for carbon, $^{33}$S, $^{34}$S, or $^{36}$S for sulfur, $^{15}$N for nitrogen, and $^{17}$O or $^{18}$O for oxygen.

In certain embodiments, the compound disclosed herein may expose a patient to a maximum of about 0.000005% DO or about 0.00001% DHO, assuming that all of the C-D bonds in the compound as disclosed herein are metabolized and released as DO or DHO. In certain embodiments, the levels of DO shown to cause toxicity in animals is much greater than even the maximum limit of exposure caused by administration of the deuterium enriched compound as disclosed herein. Thus, in certain embodiments, the deuterium-enriched compound disclosed herein should not cause any additional toxicity due to the formation of DO or DHO upon drug metabolism.

In certain embodiments, the deuterated compounds disclosed herein maintain the beneficial aspects of the corresponding non-isotopically enriched molecules while substantially increasing the maximum tolerated dose, decreasing toxicity, increasing the half-life (T), lowering the maximum plasma concentration (Cmax) of the minimum efficacious dose (MED), lowering the efficacious dose and thus decreasing the non-mechanism-related toxicity, and/or lowering the probability of drug-drug interactions. The deuterated compounds of the disclosure shows improved AUC. For example, the AUC measurements for cystamine D4-derived cysteamine D2 were much higher than cystamine derived cysteamine and also cysteamine D2-derived cysteamine D1. The hepatocyte elimination studies, described below, show that D4-cystamine is the most stable of the dimeric compounds. Without wanting to be bound to any particular theories, this is thought to be why D4 results in a higher AUC and Cmax (for its monomer form) compared with D2 and cystamine and also reduced rate of elimination in the hepatocyte elimination studies. Moreover, the data show that the deuterated compounds of the disclosure reduce macrophage and microglial cells in liver tissue having a fatty liver phenotype. For example, the data below show there was a statistically significant reduction (p<0.0001) in the number of CD11b positive cells in liver tissue in mice treated with D2 and D4-cystamine compared with the control group.

In a further embodiment, the compounds of the disclosure exhibit a reduced rate of metabolism by at least one polymorphically-expressed cytochrome P450 isoform in a subject per dosage unit thereof in comparison to non-isotopically enriched cysteamine and cystamine. Examples of polymorphically-expressed cytochrome P450 isoforms include, but are not limited to, CYP2C8, CYP2C9, CYP2C19, and CYP2D6. In another embodiment, the compounds of the disclosure exhibit a reduced rate of metabolism by at least one cytochrome P450 isoform or monoamine oxidase isoform in a subject per dosage unit thereof in comparison to non-isotopically enriched cysteamine and cystamine. Examples of cytochrome P450 isoforms and monoamine oxidase isoforms, include but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, CYP51, MAOA, and MAOB.

In certain embodiments, the compounds of the disclosure exhibit an improvement in a diagnostic hepatobiliary function end point, as compared to the corresponding non-isotopically enriched cysteamine and cystamine. Examples of diagnostic hepatobiliary function endpoints include, but are not limited to, alanine aminotransferase (ALT), serum glutamic pyruvic transaminase ("SGPT"), aspartate aminotransferase ("AST", "SGOT"), ALT/AST ratios, serum aldolase, alkaline phosphatase (ALP), ammonia levels, bilirubin, gamma glutamyltranspeptidase ("GGTP", "γ-GTP", "GGT"), leucine aminopeptidase ("LAP"), liver biopsy, liver ultrasonography, liver nuclear scan, 5'-nucleotidase, and blood protein.

For example, the data below demonstrate that deuterated compounds of the disclosure (e.g., D2 and D4-cystamine) can reverse steatohepatitis as suggested by reduced ALT, reduced fibrosis, reduced Collagen 1 and TIMP expression, reduced steatosis (pericentral) and reduced inflammatory infiltrate (CD11b). Accordingly, a deuterated compound of the disclosure can reduce ALT, reduce fibrosis, reduce Collagen 1 and TIMP expression, reduce steatosis (pericentral) and reduce inflammatory infiltrate (CD11b) of the liver. Moreover, the disclosure provides method of treating a subject to reduce ALT, reduce fibrosis, reduce Collagen 1 and TIMP expression, reduce steatosis (pericentral) and/or reduce inflammatory infiltrate (CD11b) comprising administering a deuterated compound of the disclosure.

In another embodiment, processes for preparing a compound as disclosed herein or other pharmaceutically acceptable derivative thereof such as a salt, solvate, or prodrug, as an antioxidant, and a treatment for cystinosis and fatty liver disorders, such as NAFLD and NASH.

While it may be possible for the compounds of the disclosure to be administered as the raw chemical, it is also possible to present them as a pharmaceutical composition. Accordingly, provided herein are pharmaceutical compositions which comprise one or more of certain deuterated compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, Remington. The Science and Practice of Pharmacy, supra; Modified-Release Drug Delivery Technology, Rathbone et al., Eds. Drugs and the Pharmaceutical Science, Marcel Dekker, Inc.: New York, N.Y., 2002; Vol. 126). For example, in one embodiment, a deuterated cysteamine and/or cystamine can be enterically coated (e.g., enterically coated beads or capsules). As mentioned above and elsewhere herein non-deuterated enteric formulations of cysteamine bitartrate have been shown to provide improved drug compliance, reduce frequency of administration and prolonged reduction of cystine levels in cystinosis patients. Because the deuterated forms of the compounds of the disclosure also include a longer half-life, an enterically coated formulation comprising a deuterated compound of formula I and/or II can have improved administration and longer biological activity. In some embodiments, an enterically coated formulation of compound of formula I and/or II can be administered at lower doses than a non-deuterated enteric formulation and/or may be administered less frequently.

The compositions include those suitable for oral, parenteral (including Subcutaneous, intradermal, intramuscular, intravenous, intraarticular, and intramedullary), intraperitoneal, transmucosal, transdermal, rectal and topical (including dermal, buccal, Sublingual and intraocular) administration. The most suitable route for administration depends on a variety of factors, including interpatient variation or disorder type, and therefore the disclosure is not limited to just one form of administration. The compositions may conveniently be presented in unit dosage form and may be prepared by any of the methods well known in the art of pharmacy. Typically, these methods include the step of bringing into association a compound of the disclosure or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules (including enterically coated granules); as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Moulded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer Solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose.

For administration by inhalation, compounds may be delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator. Typical unit dosage formulations are those containing an effective dose, as herein below recited, or an appropriate fraction thereof, of the active ingredient.

Tablets or other forms of presentation provided in discrete units may conveniently contain an amount of one or more compounds which is effective at such dosage or as a multiple of the same, for instance, units containing 1 mg to 1000 mg of the compounds disclosed herein, usually around 100 mg to 500 mg of the compound.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

The disclosure contemplates that typical delivery will be by oral routes. Formulations for such delivery include enterically coated formulations as well as non-enterically formulated formulation comprising at least one deuterated form of cystamine and/or cysteamine. As presented below, the deuterated forms comprise pharmacokinetic and pharmacodynamic changes related to non-deuterated forms. Moreover, prior formulations comprising enterically coated cysteamine and/or cystamine have also showed improved pharmacokinetic and pharmacodynamic data relative to non-enterically formulated formulations. Accordingly, the combination of enterically coated and deuterated forms of cystamine and/or cysteamine are expected to further modulate the pharmacokinetics and pharmacodynamics of cysteamine and/or cysteamine delivery including, for example, both the delayed and extended release of the active ingredient as reflected by modulation of the AUC and Cmax and/or Tmax.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously or temporarily suspended for a certain length of time (i.e., a "drug holiday"). Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

This disclosure identifies patient populations that can benefit from the compounds disclosed herein, particularly juvenile patients. The disclosure provides composition of the compounds disclosed herein that can be used in the treatment of various diseases including cystinosis, Huntington's disease, and NAFLD (including NASH).

Cystinosis is a rare disease that is typically diagnosed prior to age 2. Cystinosis is a genetic metabolic disease that causes an amino acid, cystine, to accumulate in various organs of the body. Cystine crystals accumulate in the kidneys, eyes, liver, muscles, pancreas, brain, and white blood cells. Without specific treatment, children with cystinosis develop end stage kidney failure at approximately age nine. Cystinosis also causes complications in other organs of the body. The complications include muscle wasting, difficulty swallowing, diabetes, and hypothyroidism. It is estimated that at least 2,000 individuals worldwide have cystinosis, though exact numbers are difficult to obtain because the disease is often undiagnosed and/or misdiagnosed. There are three forms of Cystinosis. Infantile Nephropathic Cystinosis is the most severe form of the disease. Children with Cystinosis appear normal at birth, but by 10 months of age, they are clearly shorter than others their age. They urinate frequently, have excessive thirst, and often seem fussy. At 12 months, they haven't walked and bear weight only gingerly. One of the major complications of Cystinosis is renal tubular Fanconi Syndrome, or a failure of the kidneys to reabsorb nutrients and minerals. The minerals are lost in the urine. The urinary losses must be replaced. Generally, they are picky eaters, crave salt, and grow very slowly. If left untreated, this form of the disease may lead to kidney failure by 10 years of age. In people with Intermediate Cystinosis or Juvenile (adolescent) Cystinosis, kidney and eye symptoms typically become apparent during the teenage years or early adulthood. In Benign or Adult Cystinosis, cystine accumulates primarily in the cornea of the eyes. Cystinosis is treated symptomatically. Renal tubular dysfunction requires a high intake of fluids and electrolytes to prevent excessive loss of water from the body (dehydration). Sodium bicarbonate, sodium citrate, and potassium citrate may be administered to maintain the normal electrolyte balance. Phosphates and vitamin D are also required to correct the impaired uptake of phosphate into the kidneys and to prevent rickets. Carnitine may help to replace muscular carnitine deficiency.

Cysteamine (Cystagon®) has been approved by the Food and Drug Administration (FDA) for standard treatment of Cystinosis. Cysteamine is a cystine-depleting agent that lowers cystine levels within the cells. Cysteamine has proven effective in delaying or preventing renal failure. Cysteamine also improves growth of children with Cystinosis. In view of the harmful effects of chronic cystine accumulation, and the indications of the effectiveness of Cysteamine therapy in various tissues and organ systems, oral Cysteamine should be used by post-transplant Cystinosis patients. Procysbi® (cysteamine bitartrate delayed release capsules) was approved by the FDA in May 2013. Cystaran (cysteamine ophthalmic solution) 0.44% is an ophthalmic solution approved by the FDA for the treatment of corneal cystine crystal accumulation in patients with cystinosis.

The disclosure provides compositions comprising deuterated cysteamine and/or cystamine having a pharmacokinetic and/or pharmacodynamic profile compared to non-deuterated forms is improved. For example, the disclosure provides compositions comprising deuterated cysteamine and/or cystamine wherein the amount of deuterated cysteamine and/or cystamine remaining after 30 minutes in a hepatocyte elimination studies is greater than 20%, 21%, 22%, 23%, 24% or 25% compared to non-deuterated cystamine or cysteamine (see, Table 1). As can be seen from Table 1, D4 cystamine is eliminated at a slower rate than D2 or non-deuterated cystamine (i.e., D4 is slower than D2 which is slower than non-deuterated cystamine). This correlates with the higher AUC for D2-cysteamine (when D-4 cystamine is administered to rats. Table 1 also shows that D-cysteamine and D2-cysteamine are eliminated at a slower rate than cysteamine bitartrate.

ment, the dose is up to about 10-40 mg/kg. In another embodiment, the dose is administered 2-4 times per day at about 300 mg to 1 gram per dose. In a further embodiment, the compound of the disclosure is administered in multiple doses that do not exceed 2.0 g/m$^2$/day or 95 mg/kg/day. Typically, the dose is changed over time to reach the highest tolerable dose for the subject, typically between about 30-50 µmol plasma of a compound disclosed herein. For example, an initial dose may provide a circulating level of about 10 µmol of the compound of the disclosure, which will be adjusted up to the highest tolerable dose, typically about 40 µmol. Similarly, an initial dose may result in a circulating level of 80 µmol, which will be adjusted down to about 40 µmol. When the compound is well tolerated, the goal of therapy is to keep leukocyte cystine levels below 1 nmol/½ cystine/mg protein five to six hours following administration of the compound of the disclosure. Patients with poorer tolerability still receive significant benefit if white cell cystine levels are below 2 nmol/½ cystine/mg protein. The dose of the compound disclosed herein can be increased to a maximum of 2.0 grams/m$^2$/day to achieve this level. The recommended maintenance dose of 1.30 grams/m$^2$/day can be approximated by administering the compound according to the following table, which takes surface area as well as weight into consideration.

TABLE 1

Hepatocyte elimination.
"D" = 1 deuterated position, "D2" = 2 deuterated position, "D4" = 4 deuterated positions.
"Cystamine" and "Cysteamine Bitartrate" are non-deuterated.

| TIME (min) | D-Cysteamine | D2-Cysteamine | D2-Cystamine | D4-Cystamine | Cysteamine Bitartrate | Cystamine |
|---|---|---|---|---|---|---|
| | % | | | | | |
| 0 | 100% | 100 | 100 | 100 | 100 | 100 |
| 15 | 34.4 | 231.2 | 22.6 | 131.4 | 15.4 | 18.5 |
| 30 | 41.5 | 84.4 | 24.3 | 35.9 | 2.7 | 6.5 |
| 60 | 42.9 | 7.4 | 0 | 14.5 | 1.2 | |
| 120 | 6.7 | | | | | |

Moreover, the data shows that the deuterated compounds of the disclosure have higher Cmax and AUC compared to non-deuterated compounds. For example, a study of rats receiving non-deuterated cytamine and D4-cystamine shows that the Cmax of the deuterated compound was ~2× that of the non-deuterated compounds and that the AUC was at least 1.6× greater than non-deuterated cystamine (Table 2).

TABLE 2

Average Pharmacokinetic data from rats receiving cystamine and D4-cystamine. The monomer (cysteamine or D2-cysteamine) was measured.

| | Cmax (uM) | AUC to last measured concentration (uM*min) | AUC to infinity (uM*min) |
|---|---|---|---|
| Cystamine group average | 24.85481563 | 2707.887943 | 2855.616734 |
| D4-Cystamine group average | 51.665377 | 4519.806454 | 4651.635913 |

In one embodiment, a subject having cystinosis is administered a compound of the disclosure or pharmaceutically acceptable salt thereof in an amount to obtain about 10-100 µmol (e.g., 10, 20, 30, 40, 50, 60, 70, 80 or any value there between) of the compound in the plasma. In one embodi-

| Weight in Pounds | mg of compound (Free Base) Every 6 Hours |
|---|---|
| 0-10 | 100 |
| 11-20 | 150 |
| 21-30 | 200 |
| 31-40 | 250 |
| 41-50 | 300 |
| 51-70 | 350 |
| 71-90 | 400 |
| >110 | 500 |

Patients over age 12 and over 110 pounds should receive 2.0 grams/day given in four divided doses as a starting maintenance dose. This dose should be reached after 4 to 6 weeks of incremental dosage increases as stated above. The dose should be raised if the leukocyte cystine level remains>2 nmol/½ cystine/mg/protein.

Leukocyte cystine measurements, taken 5 to 6 hours after dose administration, are recommended for new patients after the maintenance dose is achieved. Patients being transferred from solutions comprising the compound to capsules should have their white cell cystine levels measured in 2 weeks, and thereafter every 3 months to assess optimal dosage as described above.

If the compound of the disclosure is poorly tolerated initially due to gastrointestinal tract symptoms or transient skin rashes, therapy should be temporarily stopped, then re-instituted at a lower dose and gradually increased to the proper dose.

The compositions and methods of the disclosure can also be used to treat NAFLD and NASH as well as liver fibrotic diseases. Non-alcoholic fatty liver disease (NAFLD) represents a spectrum of disease occurring in the absence of alcohol abuse. It is characterized by the presence of steatosis (fat in the liver) and may represent a hepatic manifestation of the metabolic syndrome (including obesity, diabetes and hypertriglyceridemia). NAFLD is linked to insulin resistance, it causes liver disease in adults and children and may ultimately lead to cirrhosis (Skelly et al., J Hepatol 2001; 35: 195-9; Chitturi et al., Hepatology 2002; 35(2):373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., J Gastroenterol Hepatol 2002; 17 Suppl:S186-90). NASH is characterized by the histologic presence of steatosis, cytological ballooning, scattered inflammation and pericellular fibrosis (Contos et al., Adv Anat Pathol 2002; 9:37-51). Hepatic fibrosis resulting from NASH may progress to cirrhosis of the liver or liver failure, and in some instances may lead to hepatocellular carcinoma.

The degree of insulin resistance (and hyperinsulinemia) correlates with the severity of NAFLD, being more pronounced in patients with NASH than with simple fatty liver (Sanyal et al., Gastroenterology 2001; 120(5):1183-92). As a result, insulin-mediated suppression of lipolysis occurs and levels of circulating fatty acids increase. Two factors associated with NASH include insulin resistance and increased delivery of free fatty acids to the liver. Insulin blocks mitochondrial fatty acid oxidation. The increased generation of free fatty acids for hepatic re-esterification and oxidation results in accumulation of intrahepatic fat and increases the liver's vulnerability to secondary insults.

Glutathione (gammaglutamyl-cysteinyl-glycine; GSH) is a major endogenous antioxidant and its depletion is implicated in the development of hepatocellular injury (Wu et al., J Nutr 2004; 134(3):489-92). One such injury is acetaminophen poisoning, where reduced GSH levels become depleted in an attempt to conjugate and inactivate the hepatotoxic metabolite of the drug. After a toxic dose of acetaminophen, excess metabolite (N-acetyl-benzoquinoneimine) covalently binds to hepatic proteins and enzymes resulting in liver damage (Wu et al., J Nutr 2004; 134(3):489-92; Prescott et al., Annu Rev Pharmacol Toxicol 1983; 23:87-101). Increased glutathione levels appears therefore to have some protective effects through the reduction of ROS. Glutathione itself is does not enter easily into cells, even when given in large amounts. However, glutathione precursors do enter into cells and some GSH precursors such as N-acetylcysteine have been shown to be effective in the treatment of conditions such as acetaminophen toxicity by slowing or preventing GSH depletion (Prescott et al., Annu Rev Pharmacol Toxicol 1983; 23:87-101). Examples of GSH precursors include cysteine, N-acetylcysteine, methionine and other sulphur-containing compounds such as cysteamine (Prescott et al., J Int Med Res 1976; 4(4 Suppl):112-7).

Cysteine is a major limiting factor for GSH synthesis and that factors (e.g., insulin and growth factors) that stimulate cysteine uptake by cells generally result in increased intracellular GSH levels (Lyons et al., Proc Natl Acad Sci USA 2000; 97(10):5071-6; Lu S C. Curr Top Cell Regul 2000; 36:95-11).

N-acetylcysteine has been administered to patients with NASH. In reports from Turkey, obese individuals with NASH treated with N-acetylcysteine for 4-12 weeks exhibited an improvement in aminotransferase levels and gamma-GT even though there was no reported change in subject body mass index (Pamuk et al., J Gastroenterol Hepatol 2003; 18(10):1220-1).

Studies in mice and humans showed cysteamine to be effective in preventing acetaminophen-induced hepatocellular injury (Prescott et al., Lancet 1972; 2(7778):652; Prescott et al., Br Med J 1978; 1(6116):856-7; Mitchell et al., Clin Pharmacol Ther 1974; 16(4):676-84). Cystamine and cysteine have been reported to reduce liver cell necrosis induced by several hepatotoxins. (Toxicol Appl Pharmacol. 1979 April; 48(2):221-8). Cystamine has been shown to ameliorate liver fibrosis induced by carbon tetrachloride via inhibition of tissue transglutaminase (Qiu et al., World J Gastroenterol. 13:4328-32, 2007).

The prevalence of NAFLD in children is unknown because of the requirement of histologic analysis of liver in order to confirm the diagnosis (Schwimmer et al., Pediatrics 2006; 118(4):1388-93). However, estimates of prevalence can be inferred from pediatric obesity data using hepatic ultra-sonongraphy nd elevated serum transaminase levels and the knowledge that 85% of children with NAFLD are obese. Data from the National Health and Nutrition Examination Survey has revealed a threefold rise in the prevalence of childhood and adolescent obesity over the past 35 years; data from 2000 suggests that 14-16% children between 6-19 yrs age are obese with a BMI>95% (Fishbein et al., J Pediatr Gastroenterol Nutr 2003; 36(1):54-61), and also that fact that 85% of children with NAFLD are obese.

The exact mechanism by which NAFLD develops into NASH remains unclear. Because insulin resistance is associated with both NAFLD and NASH, it is postulated that other additional factors are also required for NASH to arise. This is referred to as the "two-hit" hypothesis (Day C P. Best Pract Res Clin Gastroenterol 2002; 16(5):663-78) and involves, firstly, an accumulation of fat within the liver and, secondly, the presence of large amounts of free radicals with increased oxidative stress. Macrovesicular steatosis represents hepatic accumulation of triglycerides, and this in turn is due to an imbalance between the delivery and utilization of free fatty acids to the liver. During periods of increased calorie intake, triglyceride will accumulate and act as a reserve energy source. When dietary calories are insufficient, stored triglycerides (in adipose) undergo lipolysis and fatty acids are released into the circulation and are taken up by the liver. Oxidation of fatty acids will yield energy for utilization. Treatment of NASH currently revolves around the reduction of the two main pathogenetic factors, namely, fat accumulation within the liver and excessive accumulation of free radicals causing oxidative stress. Fat accumulation is diminished by reducing fat intake as well as increasing caloric expenditure. One therapeutic approach is sustained and steady weight loss. Although not definitively proven, a >10% loss in body weight has been shown in some cases to reduce hepatic fat accumulation, normalize liver transaminases and improve hepatic inflammation and fibrosis (Ueno et al., J Hepatol 1997, 27(1):103-7; Vajro et al., J Pediatr 1994; 125(2):239-41; Franzese et al., Dig Dis Sci 1997, 42(7):1428-32).

Reduction of oxidative stress through treatment with antioxidants has also been shown to be effective in some studies. For example, obese children who had steatosis were treated with vitamin E (400-1000 IU/day) for 4-10 months (Lavine, J Pediatr 2000, 136(6):734-8). Despite any significant change in BMI, the mean ALT levels decreased from 175±106 IU/L to 40±26 IU/L (P<0.01) and mean AST levels decreased from 104±61 IU/L to 33±11 IU/L (P<0.002). Hepatic transaminases increased in those patients who elected to discontinue vitamin E therapy. An adult study using vitamin E for one year demonstrated similar reduction of hepatic transaminases as well as the fibrosis marker TGFβ levels (Hasegawa et al., *Aliment Pharmacol Ther* 2001, 15(10):1667-72).

Steatosis also may develop into steatohepatitis through oxidative stress due to reactive oxygen species (ROS) and decreased anti-oxidant defense (Sanyal et al., *Gastroenterology* 2001, 120(5):1183-92). ROS can be generated in the liver through several pathways including mitochondria, peroxisomes, cytochrome P450, NADPH oxidase and lipooxygenase (Sanyal et al., *Nat Clin Pract Gastroenterol Hepatol*, 2005; 2(1):46-53). Insulin resistance and hyperinsulinism has been shown to increase hepatic oxidative stress and lipid peroxidation through increased hepatic CYP2EI activity (Robertson et al., *Am J Physiol Gastrointest Liver Physiol*, 2001 281(5):G1135-9; Leclercq et al., *J Clin Invest* 2000, 105(8):1067-75).

Currently, much of what is understood of the pathogenesis of NAFLD has arisen from animal studies. A number of mouse models which exhibit steatosis/steatohepatitis exist and include genetically altered leptin-deficient (ob/ob) or leptin resistant (db/db) and the dietary methionine/choline deficient (MCD) model. Studies comparing male and female rats of varying strains (Wistar, Sprague-Dawley, Long-Evans) with a mouse strain (C57BL/6) as models for NASH have been undertaken. These animals were fed for 4 weeks with an MCD diet; although ALT elevation and steatosis were more noticeable in the Wistar rat, the overall histologic changes in the liver of the mice were more constant with changes due to NASH. More recently the use of supranutritional diets in animals has resulted in a NAFLD model that physiologically more resembles the human phenotype. The medical conditions most commonly associated with NAFLD are obesity, Type II diabetes and dyslipidemia. These conditions can be induced by feeding mice and rats with high fat or sucrose diets. Rats fed with a >70% fat-rich diet for 3 weeks developed pan-lobular steatosis, patchy inflammation, enhanced oxidative stress, and increased plasma insulin concentrations suggesting insulin resistance. NASH mice have been induced through intragastric overfeeding. Mice were fed up to 85% in excess of their standard intake for 9 weeks. The mice became obese with 71% increase in final body weight; they demonstrated increase white adipose tissue, hyperglycemia, hyperinsulinemia, hyperleptinemia, glucose intolerance and insulin resistance. Of these mice 46% developed increased ALT (121=/−27 vs 13+/−1 U/L) as well as histologic features suggestive of NASH. The livers of the overfed mice were about twice as large expected, beige in color with microscopic evidence of lipid droplets, cytoplasmic vacuoles and clusters of inflammation.

Mouse models of NASH can be used to study various therapies. Mouse models are created through specific diets (methionine choline deficient, MCD) or intragastric overfeeding. These mice develop serologic and histologic features of NASH. NASH mice are useful in screening and measuring the effects cysteamine on NASH related disease and disorders. For example, the effect of treatment can be measured by separating the NASH mice into a control group where animals will continue to receive MCD diet only and three other treatment groups where mice will receive MCD diet as well as anti-oxidant therapy. The three therapy groups for example, can receive cysteamine 50 mg/kg/day, 100 mg/kg/day and sAME.

As mentioned above, NASH is a disease subset falling under the umbrella of NAFLD and is characterized by various biomarkers and histological examination. NASH has been characterized as including two types: Type 1 and Type 2, having some distinct biomarker and histological characteristics, while certain others that overlap between the two types. These two types, Type 1 and Type 2 NASH are typically identified in juvenile patients.

Type 1 NASH is characterized by steatosis, lobular inflammation, ballooning degeneration and perisinusoidal fibrosis. Type 2 NASH is characterized by steatosis, portal inflammation, and portal fibrosis. Schwimmer et al. (*Hepatology*, 42(3):641-649, 2005; incorporated herein by reference) described various criteria and biomarkers used to differentiate NASH Type 1 from NASH Type 2. In particular, Schwimmer et al. discloses that subjects with NASH Type 1 had higher AST, ALT and triglyceride levels compared to patients with NASH Type 2. However, the strongest factor demonstrating a difference in the two types of NASH are best found upon histological examination. As stated above, Type 1 NASH demonstrates a prevalent lobular inflammation in the liver in contrast with a prevalent portal inflammation in Type 2 NASH. Thus, the disclosure contemplates that one of the key differentiating factors that can be used in the methods disclosed herein is identifying, by histological examination, the presence of Type 1 vs. Type 2 NASH.

The diagnosis of steatosis is typically made when lipid deposition is visible in more than 5% of hepatocytes. NASH is diagnosed when, in addition to hepatic steatosis, both inflammatory infiltrates as well as ballooning and liver cell injury are present. The NAFLD Activity Score (NAS) was developed to provide a numerical score for patients who most likely have NASH. Accordingly, the NAS is the sum of the separate scores for steatosis (0-3), hepatocellular ballooning (0-2) and lobular inflammation (0-3), with the majority of patients with NASH having a NAS score of ≥5 (Kleiner D E, Brunt E M, Van Natta M et al. Design and validation of a histological scoring system for nonalcoholic fatty liver disease. *Hepatology* 41(6), 1313-1321 (2005)).

In addition, various studies have shown that cytokeratin 18 is a useful indicator of inflammation in NASH, due to cytokeratin 18's release from hepatocytes undergoing apoptosis. Normal cytokeratin 18 levels are typically characterized as being less than 200 units per liter. In contrast, subjects with liver disease, including NALFD and NASH have a statistically significant elevation in cytokeratin 18 (e.g., above 200 U/L; 200-300 U/L). Moreover, cytokeratin 18 levels can be used as a marker to determine whether a treatment is being effective. For example, a reduction in cytokeratin 18 levels of greater than 10% (e.g., 20-30%, 30-40%, 40-50%, 50-60%, 60-70%, 70-80% or 90-100%) is indicative that the therapy is having a beneficial effect. Other markers include commonly used liver function tests including measuring one or more of, for example, serum alanine aminotransferase (ALT), alkaline phosphatase (ALP), aspartate aminotransferase (AST) and gamma-glutamyl transpeptidase (GGT).

The effectiveness of a method or composition of the disclosure can be assessed by measuring fatty acid content and metabolism in the liver. Dosage adjustment and therapy can be made by a medical specialist depending upon, for example, the severity of NAFL.

In patients with histologically proven NAFLD, serum hepatic aminotransferases, specifically alanine aminotransferase (ALT), levels are elevated from the upper limit of normal to 10 times this level (Schwimmer et al., *J Pediatr* 2003, 143(4):500-5; Rashid et al., *J Pediatr Gastroenterol Nutr* 2000, 30(1):48-53). The ratio of ALT/AST (aspartate aminotransferase) is >1 (range 1.5-1.7) which differs from alcoholic steatohepatitis where the ratio is generally <1. Other abnormal serologic tests that may be abnormally elevated in NASH include gamma-glutamyltransferase (gamma-GT) and fasting levels of plasma insulin, cholesterol and triglyceride.

ALT levels have been shown to be indicative of liver function. For example, normal ALT levels are about 7 to 55 units (e.g., 10-40 units) per liter has been shown to correlate with normal liver function. This value is somewhat varied in children and adolescents. Thus, in some instances ALT levels less than 25 units per liter are "normal" in children and adolescents. Increased levels of ALT have been shown to correlate with liver disease and disorders. For example, NAFLD and NASH subjects typically show ALT levels of between 60 to 150 (e.g., 60-145, 70-140, 80-135, 90-130, 105-125, 110-120, or any number between any two values thereof). In some embodiment, particularly with children and adolescents, ALT levels above 25 units per liter can be indicative of NASH or NAFLD. In determining if a subject has NAFLD or NASH or is susceptible to treatment using a compound of the disclosure, ALT may be measured alone, but preferably, the determination should be made in combination with one or more other markers of liver function or dysfunction. For example, a subject having ALT levels above about 80 is indicative of liver disease or dysfunction.

AST levels have been shown to be indicative of liver function. For example, AST levels between about 8 to 48 units (e.g., 10-40 units) per liter has been shown to correlate with normal liver function. Increased levels of AST have been shown to correlate with liver disease and disorders. For example, NAFLD and NASH subjects typically show AST levels of between 40 to 100 (e.g., 45-95, 55-90, 65-85, 70-80, or any number between any two values thereof). In determining if a subject has NAFLD or NASH or is susceptible to treatment using a deuterated cysteamine or cystamine composition, AST may be measured alone, but preferably the determination should be made in combination with one or more other markers of liver function or dysfunction. For example, a subject having AST levels above about 50 is indicative of liver disease or dysfunction.

ALP levels have been shown to be indicative of liver function. For example, ALP levels between about 45 to 115 units (e.g., 50-110 units) per liter has been shown to correlate with normal liver function. Increased levels of ALP have been shown to correlate with liver disease and disorders. For example, NAFLD and NASH subjects typically show ALP levels of between 150 to 250 (e.g., 155-245, 160-240, 165-235, 170-230, 175-225, 180-220, 185-215, 190-210, 195-200, or any number between any two values thereof). In determining if a subject has NAFLD or NASH or is susceptible to treatment using a deuterated cysteamine or cystamine composition, ALP may be measured alone, but preferably the determination should be made in combination with one or more other markers of liver function or dysfunction. For example, a subject having ALP levels above about 150 is indicative of liver disease or dysfunction.

GGT levels have been shown to be indicative of liver function. For example, GGT levels between about 9 to 48 units (e.g., 10-40 units) per liter has been shown to correlate with normal liver function. Increased levels of GGT have been shown to correlate with liver disease and disorders. For example, NAFLD and NASH subjects typically show GGT levels of between 50 to 100 (e.g., 55-95, 60-90, 65-85, 70-80, or any number between any two values thereof). In determining if a subject has NAFLD or NASH or is susceptible to treatment using a deuterated cysteamine or cystamine composition, GGT may be measured alone, but preferably the determination should be made in combination with one or more other markers of liver function or dysfunction. For example, a subject having GGT levels above about 50 is indicative of liver disease or dysfunction.

Triglycerides levels have been shown to be indicative of liver function. For example, triglyceride levels less than about 150 mg/dL (e.g., 100-150 mg/dL) has been shown to correlate with normal liver function. Increased levels of triglycerides have been shown to correlate with liver disease and disorders. For example, NAFLD and NASH subjects typically show triglyceride levels of between 150 to 200 (e.g., 155-195, 160-190, 165-185, 170-180, or any number between any two values thereof). In determining if a subject has NAFLD or NASH or is susceptible to treatment using a deuterated cysteamine or cystamine composition, triglycerides may be measured alone, but preferably the determination should be made in combination with one or more other markers of liver function or dysfunction. For example, a subject having triglyceride levels above about 150 mg/dl is indicative of liver disease or dysfunction.

High triglyceride levels are known to be a leading cause of various forms of inflammation. Triglycerides are the form in which fat moves through the bloodstream. Triglycerides can be metabolized by various organs, including the liver, to form phospholipids (LDLs and HDLs), cholesterol and oxidized forms thereof. Oxidized phospholipids (OxPL) including OxLDL are known inflammatory mediators and strongly correlated with cardiovascular diseases. For example, Bieghs et al. (*Hepatology*, 65(3):894-903, 2012) describe that the use of antibodies to oxLDL led to a reduction in hepatic inflammation.

Increased amounts of adipose tissue are associated with decreased production of adiponectin. Data from studies in mice and humans increasingly implicate insufficient adiponectin as a major factor in the development of fatty liver and steatohepatitis. Adiponectin circulates as trimer (low molecular weight adiponectin), hexamer (medium molecular weight adiponectin) and higher order multimer (high molecular weight adiponectin) in serum and isoform-specific effects have been demonstrated. Epidemiological studies revealed that low adiponectin levels are associated with NASH. Moreover, adiponectin is believed to have a hepatoprotective effect due to protective effects against oxidative damage. Normal levels of adiponectin vary by age and sex. For example, females have a higher baseline adiponectin level compared to males. A normal weight female typically has an adiponectin level of between about 8.5 and 11 μg/ml and males typically have an adiponectin level of between about 6 and 8 μg/ml. In contrast, subject with fatty liver disease, NASH and/or obesity have adiponectin levels that are about 50-90% of normal levels (e.g., decreased by 10-50% from normal, or any value there between) (see, e.g., Merl et al. *Int. J. Obes* (Lond), 29(8), 998-1001, 2005).

In contrast, the resistin protein is increased in NASH subjects compared to normal subjects. Human resistin is a cysteine-rich, 108-amino-acid peptide hormone with a molecular weight of 12.5 kDa. In adult humans, resistin is expressed in bone marrow. Moreover, in adipocytes of subjects having a low or healthy BMI, resistin mRNA is almost undetectable. Consistent with this, body mass index (BMI) is appears to correlate with resistin concentrations in serum, and women may have higher resistin concentrations than men. Resistin mRNA expression in human peripheral mononuclear cells is increased by proinflammatory cytokines. Serum resistin is significantly elevated in both NASH and simple steatotic subjects. Hepatic resistin is significantly increased in NASH patients in both mRNA and protein levels than those in simple steatosis and normal control subjects. Because of the cysteine-rich structure of resistin changes in sulfur availability (mainly due to cysteine and glutathione) can have an effect on the protein's structure and function. As mentioned above, cysteamine and cystamine can modulated cysteine and/or glutathione levels in subjects taking cysteamine or cystamine.

Subjects afflicted with NAFLD or NASH tend to be in a higher percentile of weight for their age group (e.g., above the $97^{th}$ percentile for BMI for their age group). Treating pediatric patients at an early stage may have lifelong benefits in the management of liver function and obesity.

The compositions and methods of the disclosure demonstrate that deuterated compositions of the disclosure reduced liver fibrosis as well as improve liver function markers in animal models of NAFLD. For example, the data demonstrated that animal models treated with a high-fat NASH diet resulted in non-alcoholic steatohepatitis with fibrosis in the liver and that when administered a deuterated compound during the process to induce fatty liver, the deuterated compounds reduced the risk of developing NASH and markers thereof. In a further study, the disclosure demonstrates that following treatment to induce fatty liver disease administration of deuterated compounds of the disclosure resulted in an improvement in both ALT markers of liver function as well as a reduction in inflammatory infiltrate, liver fibrosis and markers of fibrosis such as collagen 1 and TIMP. Accordingly, the disclosure demonstrates that deuterated cystamine and/or cysteamine can be used to prevent and/or treat NAFLD, NASH and liver fibrosis resulting from these diseases.

The disclosure provides populations of subject with NASH that that have high probability of responding to treatment with a deuterated cysteamine or cystamine composition. The disclosure provides a method of treating a subject suffering from fatty liver disease, such as NASH, comprising administering a therapeutically effective amount of a compound of the disclosure. In one embodiment, the fatty liver disease is selected from the group consisting of non-alcoholic fatty acid liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy.

In certain embodiments, pediatric and juvenile patients are treated with a deuterated compound of the disclosure. In one embodiment, a subject having NASH is administered a formulation comprising a deuterated compound of the disclosure for oral administration in an amount to obtain about 10-80 µmol (e.g., 10, 20, 30, 40, 50, 60, 70, 80 or any value there between) of a deuterated compound disclosed herein in the plasma. In a further embodiment, the formulation is a delayed release oral formulation. In one embodiment, the dose is about 10-40 mg/kg. In another embodiment, the dose is administered 2-4 times per day at about 300 mg to 1 gram per dose. Typically, the dose is changed over time to reach the highest tolerable dose for the subject, typically between about 30-50 µmol of the compound in plasma. For example, an initial dose may provide a circulating level of about 10 µmol of the compound, which will be adjusted up to the highest tolerable dose, typically about 40 µmol. Similarly, an initial dose may result in a circulating level of 80 µmol, which will be adjusted down to about 40 µmol. In certain embodiments of any of the foregoing, subjects less than 15 years of age (e.g., less than 14, 13, 12, 11, 10, 9, 8, 7, 6, 5, 4, 3, 2 or 1 years of age) and having a body mass index (BMI) above the $97^{th}$ percentile for their age are treated with a deuterated compound of the disclosure. In some embodiments, the subject has a BMI above $97^{th}$ percentile for the age and weighs less than 65 kg. In some embodiment, these same subjects have high triglyceride levels, low LDH, and low or low normal adiponectin levels. In still another embodiment, the subjects have high or high normal resistin levels. In various embodiments of any of the foregoing, the patient weighs less than 65 kg. In various embodiments, the patient weighs from about 35-65 kg, or from about 40-60 kg, or from about 45-55 kg, or about 35, 40, 45, 50, 55, 60 or 65 kg. In various embodiments, the patient weighing less than 65 kg receives 600 to 1200 mg/day of a deuterated compound of the disclosure or an amount to obtain circulating plasma levels of the compound of about 10-80 µmol (typically about 30-50 and more commonly about 40 µmol). In any of the foregoing embodiments, the subject has Type I NASH or NASH with Type 1 histological pattern. In still another embodiment of the foregoing the subject has lobular inflammation of the liver. In still another of further embodiment of any of the foregoing, the subject has low adiponectin and high triglycerides characteristic of NASH. In still another embodiment of any of the foregoing, the subject has a marker (e.g., AST, ALT, GGT or other liver marker) having a level consistent with NASH as described herein.

In various embodiments, the patient weighs 65-80 kg, and may receive 750 to about 1500 mg/day of a compound of the disclosure or an amount to obtain circulating plasma levels of the compound of about 10-80 µmol (typically about 30-50 and more commonly about 40 µmol). In any of the foregoing embodiments, the subject has Type I NASH. In still another embodiment of the foregoing the subject has lobular inflammation of the liver. In still another of further embodiment of any of the foregoing, the subject has low adiponectin and high triglycerides characteristic of NASH.

In various embodiments, the patient weighs more than 65 kg and receives 900 to about 2000 mg/day of a deuterated compound of the disclosure or an amount to obtain circulating plasma levels of the deuterated compound of about 10-80 µmol (typically about 30-50 and more commonly about 40 µmol). In any of the foregoing embodiments, the subject has Type I NASH. In still another embodiment of the foregoing the subject has lobular inflammation of the liver. In still another of further embodiment of any of the foregoing, the subject has low adiponectin and high triglycerides characteristic of NASH.

The subject can be an adult, adolescent or child. In various embodiments, the patient is from 2 to 7 years old, from 8 to 11 years old, from 9 to 12 years old, or from 13 to 18 years old. In various embodiments, an adolescent is from 10 to 19 years old as described in the National Institutes of Health standards.

In various embodiments, the administration results in a decrease in NAFLD Activity Score of two or more points, no worsening or an improvement of fibrosis, reduction in serum aminotransferases and gammaglutamyl transpeptidase (GGT); reduction in MRI-determined hepatic fat fraction; changes to markers of oxidation and anti-oxidant status;

changes in fasting insulin and glucose; an increase in circulating adiponectin levels; a decrease in circulating resistin levels; a decrease in triglyceride levels; a decrease in oxidized phospholipids; changes in weight, height, body mass index (BMI) and waist circumference; changes in the Pediatric Quality of Life score; changes to any symptoms that patient may have experienced; proportion with a change from a histological diagnosis of definite NASH or indeterminate for NASH to not NASH at end of treatment; individual histological characteristics at end of treatment compared to baseline such as steatosis (fatty liver), lobular inflammation, portal chronic inflammation, ballooning, fibrosis score and stage 1a versus 1b fibrosis; and, change in mean NAS.

In various embodiments of the disclosure, a deuterated compound of the disclosure is administered at a daily dose ranging from about 10 mg/kg to about 2.5 g/kg, or from about 100 mg/kg to about 250 mg/kg, or from about 60 mg/kg to about 100 mg/kg or from about 50 mg/kg to about 90 mg/kg, or from about 30 mg/kg to about 80 mg/kg, or from about 20 mg/kg to about 60 mg/kg, or from about 10 mg/kg to about 50 mg/kg. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg or 1000 mg/kg, or may range between any two of the foregoing values. In some embodiments, the deuterated compound of the disclosure is administered at a total daily dose of from approximately 0.25 g/m$^2$ to 4.0 g/m$^2$ body surface area, about 0.5-2.0 g/m$^2$ body surface area, or 1-1.5 g/m$^2$ body surface area, or 1-1.95 g/m$^2$ body surface area, or 0.5-1 g/m$^2$ body surface area, or about 0.7-0.8 g/m$^2$ body surface area, or about 1.35 g/m$^2$ body surface area, or about 1.3 to about 1.95 grams/m$^2$/day, or about 0.5 to about 1.5 grams/m$^2$/day, or about 0.5 to about 1.0 grams/m$^2$/day, e.g., at least about 0.3, 0.4, 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, 3.25, 3.5 or 3.75 g/m$^2$ or may range between any two of the foregoing values.

In some embodiments, the delayed and extended release formulation comprises an enteric coating that releases a deuterated compound disclosed herein when the formulation reaches the small intestine or a region of the gastrointestinal tract of a subject in which the pH is greater than about pH 4.5. In various embodiments, the formulation releases at a pH of about 4.5 to 6.5, 4.5 to 5.5, 5.5 to 6.5 or about pH 4.5, 5.0, 5.5, 6.0 or 6.5.

In a particular embodiment, the deuterated compound of the disclosure or a pharmaceutically acceptable salt, prodrug or solvate thereof is formulated for oral administration (e.g., as a capsule, table, caplet, solution, etc.). In a further embodiment, the disclosure provides for capsules, tablets, or caplets, comprising 50 mg to 200 mg of a compound of disclosure or a pharmaceutically acceptable salt (e.g., a bitartrate salt), prodrug or solvate thereof. In yet a further embodiment, the capsules, tablets, or caplets further comprise inactive ingredients, such as colloidal silicon dioxide, croscarmellose sodium, D&C yellow no. 10 aluminum lake, FD&C blue no. 1 aluminum lake, FD&C blue no. 2 aluminum lake, FD&C red no. 40 aluminum lake, gelatin, magnesium stearate, microcrystalline cellulose, pharmaceutical glaze, pregelatinized starch, silicon dioxide, sodium lauryl sulfate, synthetic black iron oxide and/or titanium dioxide.

In yet another embodiment, a compound disclose herein is administered at a frequency of 4 or less times per day (e.g., one, two or three times per day). In various embodiments, the composition is a delayed or controlled release dosage form that provides increased delivery of a compound disclosed herein to the small intestine.

In an embodiment, the deuterated compound of the disclosure or a pharmaceutically acceptable salt, prodrug or solvate thereof is formulated for oral administration (e.g., as a capsule, table, caplet, solution, etc.) that provides for delayed release. In a further embodiment, the disclosure provides for delayed release capsules, tablets, or caplets, comprising 25 mg to 75 mg of a deuterated compound of disclosure or a pharmaceutically acceptable salt (e.g., a bitartrate salt), prodrug or solvate thereof. In yet a further embodiment, the delayed release capsules, tablets, or caplets further comprise inactive ingredients, such as microcrystalline cellulose, Eudragit® L 30 D-55, Hypromellose, talc, triethyl citrate, sodium lauryl sulfate, purified water, gelatin, titanium dioxide, blue ink and/or white ink.

The delay or controlled release form can provide a $C_{max}$ of a compound disclosed herein, or a biologically active metabolite thereof, that is at least about 35%, 50%, 75% or higher than the $C_{max}$ provided by an immediate release dosage form containing the same amount of the compound. In another embodiment, the delay and extended release formulation provides an improved AUC compared to immediately release forms of the compound. For example, the AUC is increased compared to an immediate release formulation. In yet another embodiment, the delayed or controlled release dosage form comprises an enteric coating that releases a deuterated compound disclosed herein when the composition reaches the small intestine or a region of the gastrointestinal tract of a subject in which the pH is greater than about pH 4.5. In various embodiments, the pH is between 4.5 and 6.5. In one embodiment, the pH is about 5.5 to 6.5. In one embodiment the compound of the disclosure is delivered throughout the small intestine providing an extended release in the small intestine.

The delay or controlled release form can provide a $C_{max}$ of a deuterated compound disclosed herein, or a biologically active metabolite thereof, that is at least about 10%, 20%, 30% or higher than the $C_{max}$ provided by an enterically coated non-deuterated cystamine and/or cysteamine (e.g., Procysbi®) dosage form containing the same amount of the cysteamine and/or cystamine base. In another embodiment, the delay and extended release formulation comprising a deuterated cysteamine and/or cystamine provides an improved AUC compared to non-deuterated delayed and/or extended release forms of the compound. For example, the AUC is increased compared to non-deuterated delayed and/or extended release formulation. In yet another embodiment, the delayed or controlled release dosage form comprising deuterated cystamine and/or cysteamine comprises an enteric coating that releases a compound disclosed herein when the composition reaches the small intestine or a region of the gastrointestinal tract of a subject in which the pH is greater than about pH 4.5. In various embodiments, the pH is between 4.5 and 6.5. In one embodiment, the pH is about 5.5 to 6.5. In one embodiment the compound of the disclosure is delivered throughout the small intestine providing an extended release in the small intestine.

In various embodiments, the enterically coated formulation comprising a deuterated compound of the disclosure is granulated and the granulation is compressed into a tablet or filled into a capsule. In certain embodiments, the granules are enterically coated prior to compressing into a tablet or capsule. Capsule materials may be either hard or soft, and are typically sealed, such as with gelatin bands or the like. Tablets and capsules for oral use will generally include one or more commonly used excipients as discussed herein.

A suitable pH-sensitive polymer is one which will dissolve in intestinal environment at a higher pH level (pH greater than 4.5), such as within the small intestine and therefore permit release of the pharmacologically active substance in the regions of the small intestine and not in the upper portion of the GI tract, such as the stomach.

In various embodiments, exemplary formulations comprising a deuterated compound of the disclosure that are contemplated for use in the present methods include those described in International Patent Applications PCT/US2007/002325, PCT/US2014/042607 and PCT/US2014/042616 (the disclosure of which are incorporated herein by reference).

For administration of the dosage form, i.e., the tablet or capsule comprising the enterically coated deuterated compound of the disclosure, a total weight in the range of approximately 50 mg to 1000 mg is used. In various embodiments, the tablet or capsule comprises 25, 50, 75, 100, 125, 150, 175, 200, 225, 250, 275, 300, 400 or 500 mg deuterated active ingredient, and multiple tablets or capsules are administered to reach the desired dosage. The dosage form is orally administered to a subject in need thereof.

In one embodiment, a tablet core comprises about 50 mg of a deuterated compound of the disclosure that is encapsulated in an enteric coating material having a thickness of about 60-100 μm (e.g., about 71, 73, 75, 77, or 79 μm or any value there between) and/or about 10-13% (e.g., about 10.5, 11.0, 11.2, 11.4, 11.6, 11.8, 12.0, 12.2, 12.4, 12.6, 12.8% of any value there between) by weight of the tablet. In another embodiment, a tablet core comprises about 150 mg of a deuterated compound of the disclosure about that is encapsulated in an enteric coating material having a thickness of about 90-130 μm (e.g., about 97, 99, 101, 103, 105, 107, 109, 111, 113 μm or any value there between) and/or about 9-14% (e.g., about 9.5, 9.7, 9.9, 10.1, 10.3 10.5, 11.0, 11.2, 11.4, 11.6, 11.8, 12.0, 12.2, 12.4, 12.6, 12.8, 13.0, 13.2, 13.4, 13.6, 13.8% or any value there between) by weight of the tablet by weight of the tablet.

In any of the foregoing embodiments, the enteric coating material can be selected from the group comprising polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethyl cellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters.

The composition can be administered orally or parenterally. In another embodiment, the method results in improvement in liver fibrosis compared to levels before administration of the deuterated compound of the disclosure. In yet another embodiment, the method results in a reduction in fat content of liver, a reduction in the incidence of or progression of cirrhosis, or a reduction in the incidence of hepatocellular carcinoma. In one embodiment, the method results in a decrease in hepatic aminotransferase levels compared to levels before administration of the deuterated compound of the disclosure. In a further embodiment, the administering results in a reduction in hepatic transaminase of between approximately 10% to 70%, e.g. 10, 20, 30, 40, 50, 60 or 70% or any value between these numbers, compared to levels before treatment. In yet another embodiment, the administering results in a reduction in alanine or aspartate aminotransferase levels in a treated patient to approximately 50%, 40%, 30%, 20% or 10% above normal ALT levels, or at normal ALT levels. In yet other embodiment, the administering results in a reduction in serum ferritin levels compared to levels before treatment with a compound of the disclosure. In various embodiments, the administration results in a lowering of NAS score.

In addition, various prodrugs can be "activated" by use of the enterically coated deuterated compound of the disclosure. Prodrugs are pharmacologically inert, they themselves do not work in the body, but once they have been absorbed, the prodrug decomposes. The prodrug approach has been used successfully in a number of therapeutic areas including antibiotics, antihistamines and ulcer treatments. The advantage of using prodrugs is that the active agent is chemically camouflaged and no active agent is released until the drug has passed out of the gut and into the cells of the body. For example, a number of prodrugs use S—S bonds. Weak reducing agents, such as cysteamine, reduce these bonds and release the drug. Accordingly, the deuterated compositions of the disclosure are useful in combination with pro-drugs for timed release of the drug. In this aspect, a pro-drug can be administered followed by administration of an enterically coated deuterated compound of the disclosure (at a desired time) to activate the pro-drug.

Prodrugs of cysteamine have been described previously. See, e.g., Andersen et al., In vitro Evaluation of Novel Cysteamine Prodrugs Targeted to g-Glutamyl Transpeptidase (poster presentation), which describes S-pivaloyl cysteamine derivatives, S-benzoyl cysteamine derivatives, S-acetyl cysteamine derivatives and S-benzoyl cysteamine) glutamate-ethyl ester). Omran et al., Bioorg Med Chem Lett., 21(8):2502-4, 2011, describes a folate pro-drug of cystamine as a treatment for nephropathic cystinosis.

In any of foregoing embodiments, formulations for use in the methods described herein can comprise a pharmaceutically acceptable salt of the deuterated compound of the disclosure, such a bitartrate salt, instead of free base compound.

The methods and composition of the disclosure can also include administering a second agent in combination with a deuterated compound of the disclosure to treat a disease or disorder. Thus, in another embodiment of any of the foregoing methods or composition, the subject can be treated with a combination of active agents for treating cystinosis or fatty liver disorders, such as NAFLD and NASH. The combination includes a deuterated compound of the disclosure and one or more of metformin, statins, anti-oxidants, and/or antibodies against oxidized phospholipids. Such a combination can have unexpected synergy due to a multifaceted approach to modulating inflammation and inflammatory mediators. Such a combination would increase the anti-oxidant effects of adiponectin by increasing adiponectin levels, reduce triglyceride levels thereby reducing circulating phospholipids, reduce insulin resistance, and block the proinflammatory effects of oxidized phospholipids.

It is to be understood that while the disclosure has been described in conjunction with specific embodiments thereof, that the foregoing description as well as the examples which follow are intended to illustrate and not limit the scope of the disclosure. Other aspects, advantages and modifications within the scope of the disclosure will be apparent to those skilled in the art to which the disclosure.

Examples

Chemical Synthesis of Isotopically Enriched $d_1$-Cysteamine and $d_2$-Cystamine:

tert-butyl (2-oxoethyl)carbamate 4

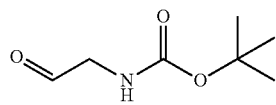

The title compound was prepared as described in Kathman et al. (*J. Am. Chem. Soc.*, 137(39):12442-12445 (2015)). Sodium periodate (9.40 g, 43.9 mmol, 1.20 equiv) was added to a suspension of tert-butyl (2,3-dihydroxypropyl) carbamate (7.00 g, 36.6 mmol, 1.00 equiv) in water (61.0 mL). The reaction was stirred in the dark at ambient temperature for 1 h. The reaction was filtered and the filtrate was extracted with chloroform (×4). The combined organic layers were dried over MgSO$_4$, filtered and concentrated to afford the title compound 4 as a yellow oil in 88% yield (5.12 g). The compound was used directly in the next step without further purification. $^1$H NMR (600 MHz, CDCl$_3$) δ 9.66 (s, 1H), 5.18 (s, 1H), 4.08 (d, J=4.9 Hz, 2H), 1.45 (s, 9H) ppm.

tert-butyl (2-hydroxyethyl-2-d)carbamate 5

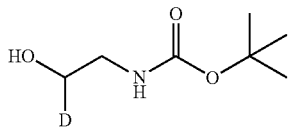

At 0° C., sodium borodeuteride (1.62 g, 38.60 mmol, 1.20 equiv.) was added portionwise to a solution of 4 (5.12 g, 32.16 mmol, 1.00 equiv.) in methanol (41 mL). The reaction was stirred for 15 minutes at 0° C. and then 1 h at ambient temperature. Water was added and the resulting mixture was extracted with dichloromethane (3×). The combined organic layers were dried over Na$_2$SO$_4$, filtered and concentrated to afford compound 5 as colorless oil in 92% yield (4.78 g). The compound was used in the next step without further purification. $^1$H NMR (600 MHz, CDCl$_3$) δ 5.17 (s, 1H), 3.62 (s, 1H), 3.29-3.20 (m, 3H), 1.41 (s, 11H) ppm. $^{13}$C NMR (151 MHz, CDCl$_3$) δ 156.95, 79.87, 62.03 (t, J=21.1 Hz), 43.07, 28.46 ppm. HRMS (ES$^+$) calculated for C$_7$H$_{14}$DNO$_3$Na [M+Na]$^+$ 185.1012, found 185.1009 IR (neat) υ 3346, 2978, 1683, 1516, 1366, 1249, 1165, 1098, 1056 cm$^{-1}$ 2-((tert-butoxycarbonyl)amino)ethyl-1-d 4-methylbenzenesulfonate 6

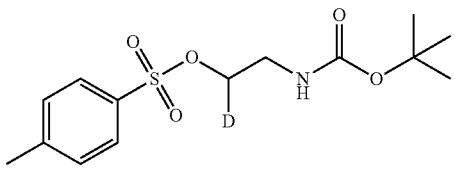 [SMILES: [2H]C(CNC(=O)OC(C)(C)C)OS(=O)(=O)c1ccc(C)cc1]

The title compound was prepared as described in Devine et al., (*ACS Infect. Dis.* 3 (3):225-236 (2017)). At 0° C., p-toluene sulfonyl chloride (2.57 g, 13.50 mmol, 1.46 equiv.) and triethylamine (2.53 mL, 18.11 mmol, 1.96 equiv.) were added to a solution of 5 (1.50 g, 9.24 mmol, 1.00 equiv.) in anhydrous dichloromethane (30 mL). The reaction was stirred at 0° C. for 10 minutes, then warmed and maintained at ambient temperature under stirring for 2 h. The reaction was concentrated and purified by silica gel column chromatography (0-20% ethyl acetate in hexanes) to give the desired compound 6 as colorless oil in 90% yield (2.62 g). $^1$H NMR (600 MHz, CDCl$_3$) δ 7.77 (d, J=8.2 Hz, 2H), 7.34 (d, J=8.1 Hz, 2H), 4.88 (s, 1H), 4.03 (d, J=4.4 Hz, 1H), 3.36 (t, J=5.2 Hz, 2H), 2.43 (s, 3H), 1.39 (s, 9H) ppm. $^{13}$C NMR (151 MHz, CDCl$_3$) δ 155.72, 145.23, 132.66, 130.07, 128.03, 79.87, 69.27 (t, J=22.7 Hz), 39.72, 28.38, 21.76 ppm. HRMS (ES$^+$) calculated for C$_{14}$H$_{20}$DNO$_5$SNa [M+Na]$^+$ 339.1101, found 339.1099 IR (neat) υ 2976, 1695, 1513, 1363, 1248, 1173, 945, 814, 661, 552 cm$^{-1}$.

S-(2-((tert-butoxycarbonyl)amino)ethyl-1-d) ethanethioate 7

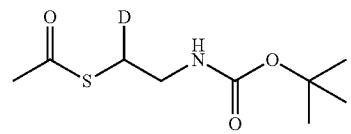

To a solution of potassium thioacetate (1.04 mg, 9.17 mmol, 2.00 equiv) in anhydrous dimethyl formamide (21.8 mL) at 0° C. was slowly added a solution of 6 (1.45 g, 4.58 mmol, 1.00 equiv) in anhydrous dimethyl formamide (7.3 mL). The reaction was stirred at 0° C. for 10 minutes, then heated to 50° C. for 90 minutes. The reaction was cooled to ambient temperature and water was added. The mixture was extracted with ethyl acetate (×3). The combined organic layers were washed with water (×2), brine, dried over Na$_2$SO$_4$, filtered and concentrated. The crude product was purified by silica gel column chromatography (0-20% of ethyl acetate in hexanes) to afford the title compound 7 as a brown oil in 56% yield (561 mg). $^1$H NMR (600 MHz, CDCl$_3$) δ 4.87 (s, 1H), 3.32-3.21 (m, 2H), 2.96 (s, 1H), 2.32 (s, 3H), 1.40 (s, 9H) ppm. $^{13}$C NMR (151 MHz, CDCl$_3$) δ 195.90, 155.88, 79.56, 40.23, 30.74, 29.16 (t, J=21.1 Hz), 28.44 ppm. HRMS (ES$^+$) calculated for C$_9$H$_{16}$DNO$_3$SNa [M+Na]$^+$ 243.0890, found 243.0887. IR (neat) υ 3356, 2977, 2932, 1685, 1512, 1365, 1246, 1164, 1129, 954, 621 cm$^{-1}$.

tert-butyl (2-mercaptoethyl-2-d)carbamate 8

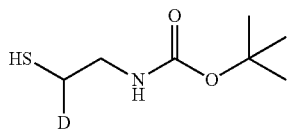

di-tert-butyl(disulfanediylbis(ethane-2,1-diyl-2d))
dicarbamate 9

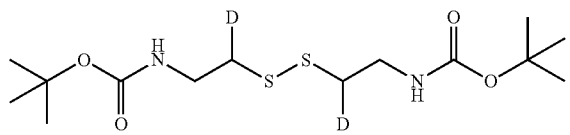 [SMILES: [2H]C(CNC(=O)OC(C)(C)C)SSC([2H])CNC(=O)OC(C)(C)C]

An aqueous solution of sodium hydroxide (10% wt, 4.30 mL) was added to a solution of 7 (340 mg, 1.54 mmol, 1.00 equiv) in methanol (8.60 mL). The reaction was stirred at ambient temperature for 40 minutes. Water was added and the mixture was extracted with ethyl acetate (×3). The combined organic layers were dried over $Na_2SO_4$, filtered and concentrated. The crude reaction was purified by silica gel column chromatography (0-20% of ethyl acetate in hexanes) to give both the tert-butyl (2-mercaptoethyl-2-d) carbamate (8) as a colorless oil in 61% yield (167 mg) and the di-tert-butyl(disulfanediylbis(ethane-2,1-diyl-2-d))dicarbamate (9) as an orange solid in 19% yield (53 mg).

tert-butyl (2-mercaptoethyl-2-d)carbamate (8): $^1$H NMR (600 MHz, $CDCl_3$) δ 4.98 (s, 1H), 3.32-3.22 (m, 2H), 2.60 (d, J=6.3 Hz, 1H), 1.42 (s, 9H), 1.32 (d, J=8.4 Hz, 1H) ppm. $^{13}$C NMR (151 MHz, $CDCl_3$) δ 155.85, 79.60, 43.59, 28.46, 24.87 (t, J=21.1 Hz) ppm. HRMS (ES$^+$) calculated for $C_{14}H_{26}D_2N_2O_4S_2Na$ [M+Na]$^+$ 377.1514, found 377.1511 (detected as dimer) IR (neat) υ 3355, 2977, 2932, 1687, 1509, 1365, 1247, 1162 cm$^{-1}$.

di-tert-butyl(disulfanediylbis(ethane-2,1-diyl-2-d))dicarbamate 9: $^1$H NMR (600 MHz, $CDCl_3$) δ 5.11 (s, 2H), 3.41 (t, J=5.9 Hz, 4H), 2.75 (s, 2H), 1.41 (s, 18H) ppm. $^{13}$C NMR (151 MHz, $CDCl_3$) δ 155.96, 79.58, 39.27, 38.16 (t, J=21.1 Hz), 28.47 ppm. HRMS (ES$^+$) calculated for $C_{14}H_{26}D_2N_2O_4S_2Na$ [M+Na]$^+$ 377.1514, found 377.1510 IR (neat) υ 3346, 2976, 2931, 1685, 1512, 1365, 1247, 1164 cm$^{-1}$.

di-tert-butyl(disulfanediylbis(ethane-2,1-diyl-2-d))
dicarbamate 11

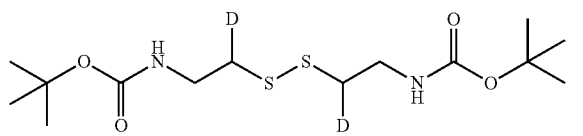 [SMILES: [2H]C(CNC(=O)OC(C)(C)C)SSC([2H])CNC(=O)OC(C)(C)C]

Sodium bicarbonate (267 mg, 3.17 mmol, 1.50 equiv) and iodine (321 mg, 1.27 mmol, 0.60 equiv) were added portionwise to a solution of tert-butyl (2-mercaptoethyl-2-d) carbamate (8, 376 mg, 2.11 mmol, 1.00 equiv) in methanol (15 mL). After 5 minutes, a saturated solution of sodium bicarbonate was added. The mixture was extracted with ethyl acetate (×3). The combined organic layers were washed with water, a solution of sodium thiosulfate (10 w.t, 4×50 mL), and brine; dried over $Na_2SO_4$; and then filtered and concentrated to afford the desired product in 91% (341 mg).

2-aminoethane-1-d-1-thiol hydrochloride 10
(BL-0646)

At 0° C., a solution of tert-butyl (2-mercaptoethyl-2-d) carbamate (8, 160 mg, 0.90 mmol, 1.00 equiv) in methanol (1.5 mL) was added to a solution containing HCl (4N in 1,4-dioxane, 6.50 mL). The reaction was stirred at ambient temperature for 1 hour. The reaction was concentrated to afford the desired compound in a quantitative yield as a white solid (102 mg). $^1$H NMR (600 MHz, $D_2O$) δ 3.15 (d, J=6.5 Hz, 2H), 2.84-2.68 (m, 1H) ppm. $^{13}$C NMR (151 MHz, $D_2O$ (+MeOH as the internal standard)) δ 42.50, 21.63 (t, J=21.1 Hz) ppm. HRMS (ES$^+$) calculated for $C_2H_6DNS$ [M+H]$^+$ 79.0435, found 79.0437.

2,2'-disulfanediylbis(ethan-2-d-1-amine)dihydro-
chloride 11-BL-0647

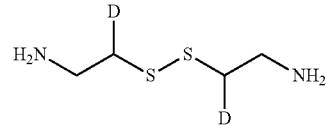

At 0° C., a solution of HCl (4N in 1,4-dioxane, 2.00 mL) was added to a solution of di-tert-butyl(disulfanediylbis(ethane-2,1-diyl-2-d))dicarbamate (9, 50 mg, 0.14 mmol, 1.00 equiv) in methanol (0.5 mL). The reaction was stirred at ambient temperature for 2 h. The reaction was concentrated to get the desired compound in a quantitative yield as a beige powder (32 mg). $^1$H NMR (600 MHz, $D_2O$) δ 3.35 (d, J=6.4 Hz, 4H), 2.95 (t, J=6.4 Hz, 2H) ppm. $^{13}$C NMR (151 MHz, $D_2O$(+MeOH as the internal standard) δ 38.20, 33.55 (t, J=21.1 Hz) ppm. HRMS (ES$^+$) calculated for $C_4H_{11}D_2N_2S_2$ [M+H]$^+$ 155.0640, found 155.0645.

Chemical Synthesis of Isotopically Enriched $d_2$-Cysteamine and $d_4$-Cystamine:

tert-butyl (2-hydroxyethyl-2,2-$d_2$)carbamate

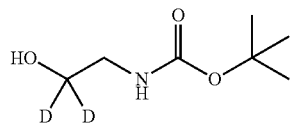

N-Boc-glycine methyl ester (0.100 g, 0.528 mmol, 1.00 equiv) was slowly added to a stirred solution of lithium aluminum deuteride (0.027 g, 0.634 mmol, 1.20 equiv) in anhydrous tetrahydrofuran (1 mL) at 0° C. The mixture was heated at reflux for 3 h and then cooled at 0° C. Ethyl acetate (2 mL) was first added, followed by addition of Rochelle's salt (1 mL). The reaction mixture was stirred at ambient temperature for 1 h, then water was added and the mixture was extracted with ethyl acetate (×3). The combined organic layers were washed with brine (×2), dried over $Na_2SO_4$, filtered and concentrated to give desired compound as a colorless oil in quantitative yield (0.09 g, 0.552 mmol). The compound was used in the next step without further purification. $^1$H NMR (599 MHz, $CDCl_3$) δ 5.15 (s, 1H), 3.24 (d, J=6.0 Hz, 2H), 3.14 (s, 1H), 1.41 (s, 9H) ppm; $^{13}$C NMR (151 MHz, $CDCl_3$) δ 156.97, 79.75, 43.05, 28.48 ppm; HRMS (ES$^+$) calculated for $C_7H_{13}D_2NO_3Na$ [M+Na]$^+$ 186.1070, found 186.1071.

2-((tert-butoxycarbonyl)amino)ethyl-1,1-$d_2$ 4-methylbenzenesulfonate

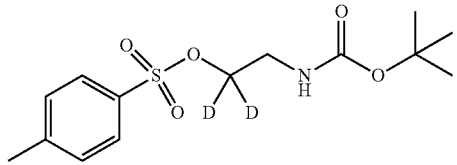 [SMILES: [2H]C([2H])(CNC(=O)OC(C)(C)C)OS(=O)(=O)c1ccc(C)cc1]

At 0° C., p-toluene sulfonyl chloride (0.329 g, 1.73 mmol, 1.46 equiv) and triethylamine (0.322 mL, 2.31 mmol, 1.96 equiv) were added to a solution of tert-butyl (2-hydroxyethyl-2,2-$d_2$)carbamate (0.193 g, 1.18 mmol, 1.00 equiv) in anhydrous dichloromethane (2.1 mL). The reaction was stirred at 0° C. for 10 minutes, then warmed to ambient temperature and stirred for 2 h. The reaction was concentrated and purified by silica gel column chromatography (hexanes/ethyl acetate 80:20) to afford the desired compound as a colorless oil in 51% yield (0.192 g, 0.605 mmol). $^1$H NMR (599 MHz, $CDCl_3$) δ 7.77 (d, J=8.3 Hz, 2H), 7.34 (d, J=8.1 Hz, 2H), 4.88 (s, 1H), 3.35 (d, J=6.0 Hz, 2H), 2.43 (s, 3H), 1.39 (s, 9H) ppm; $^{13}$C NMR (151 MHz, $CDCl_3$) δ 155.72, 145.14, 132.68, 130.06, 128.02, 79.87, 39.66, 28.38, 21.76 ppm; HRMS (ES$^+$) calculated for $C_{14}H_{19}D_2NO_5SNa$ [M+Na]$^+$ 340.1158, found 340.1156.

S-(2-((tert-butoxycarbonyl)amino)ethyl-1,1-$d_2$) ethanethioate

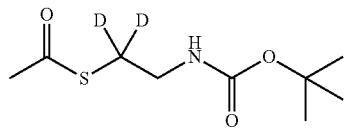 [SMILES: [2H]C([2H])(CNC(=O)OC(C)(C)C)SC(C)=O]

At 0° C., a solution of 2-((tert-butoxycarbonyl)amino)ethyl-1,1-$d_2$ 4-methylbenzenesulfonate (0.160 g, 0.504 mmol, 1.00 equiv) in anhydrous DMF (0.8 mL) was slowly added to a solution of potassium thioacetate (0.115 g, 1.01 mmol, 2.00 equiv) in anhydrous DMF (2.4 mL). The reaction was stirred at 0° C. for 10 minutes, then heated to 50° C. for 90 minutes. The reaction was cooled to ambient temperature and water was added. The mixture was extracted with ethyl acetate (×3). The combined organic layers were washed with water (×2), brine, dried over $Na_2SO_4$, filtered and concentrated. The crude product was purified by silica gel column chromatography (hexanes/EtOAc 80:20) to give the desired compound as a yellow oil in 59% yield (0.066 g; 0.298 mmol). $^1$H NMR (599 MHz, $CDCl_3$) δ 4.81 (s, 1H), 3.28 (d, J=6.2 Hz, 2H), 2.34 (s, 3H), 1.42 (s, 9H) ppm. $^{13}$C NMR (151 MHz, $CDCl_3$) δ 195.93, 155.90, 79.65, 40.22, 30.80, 28.49 ppm; HRMS (ES$^+$) calculated for $C_9H_{15}D_2NO_3SNa$ [M+Na]$^+$ 224.0947, found 224.0948.

tert-butyl (2-mercaptoethyl-2,2-$d_2$)carbamate

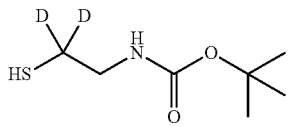

An aqueous solution of sodium hydroxide (10% wt, 1.6 mL) was added to a solution of S-(2-((tert-butoxycarbonyl)amino)ethyl-1,1-$d_2$) ethanethioate (0.126 g, 0.569 mmol, 1 equiv) in methanol (3.0 mL). The reaction was stirred at ambient temperature for 40 minutes. Water was added and the mixture was extracted with ethyl acetate (×3). The combined organic layers were dried over $Na_2SO_4$, filtered and concentrated. The crude reaction was split in two equal parts and one of them purified by silica gel column chromatography (hexanes/EtOAc 80:20 to 70:30) to give the tert-butyl (2-mercaptoethyl-2,2-$d_2$)carbamate as a colourless oil in 43% yield (0.044 mg, 0.245 mmol). HRMS (ES$^+$) calculated for $C_7H_{13}D_2NO_2SNa$ [M+Na]$^+$ 202.0841, found 202.0838. $^1$H NMR (599 MHz, $CDCl_3$) δ 4.95 (s, 1H), 3.28 (d, J=6.3 Hz, 2H), 1.43 (s, 9H) ppm; $^{13}$C NMR (151 MHz, $CDCl_3$) δ 155.87, 79.65, 43.53, 28.49 ppm; HRMS (ES$^+$) calculated for $C_7H_{13}D_2NO_2SNa$ [M+Na]$^+$ 202.0841, found 202.0838.

di-tert-butyl(disulfanediylbis(ethane-2,1-diyl-2,2-$d_2$))dicarbamate

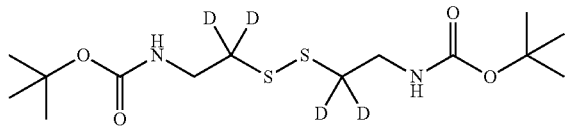 [SMILES: [2H]C([2H])(CNC(=O)OC(C)(C)C)SSC([2H])([2H])CNC(=O)OC(C)(C)C]

Sodium bicarbonate (0.006 g, 0.675 mmol, 1.5 equiv) and iodine (0.007 g, 0.027 mmol, 0.6 equiv) were added portionwise to a solution of tert-butyl (2-mercaptoethyl-2,2-$d_2$) carbamate (0.008 g, 0.045 mmol, 1 equiv) in methanol (0.10 mL). After 5 minutes, a saturated solution of sodium bicarbonate was added and the mixture was extracted with ethyl acetate (×3). The combined organic layers were washed with water, a solution of sodium thiosulfate (10 w.t, 4×2 mL), brine, and dried over $Na_2SO_4$, filtered and concentrated. The crude product was purified by silica gel column chromatography (hexanes/EtOAc 75:25) to afford the title product as a white solid in 25% yield (0.005 g, 0.011 mmol). $^1$H NMR (599 MHz, $CDCl_3$) δ 5.03 (s, 2H), 3.43 (d, J=6.2 Hz, 4H), 1.44 (s, 18H) ppm; $^{13}$C NMR (151 MHz, $CDCl_3$) δ 155.97, 79.71, 39.23, 28.54 ppm; HRMS (ES$^+$) calculated for $C_{14}H_{24}D_4N_2O_4S_2Na$ [M+Na]$^+$ 379.1634, found 379.1630.

2,2'-disulfanediylbis(ethan-2,2-d₂-1-aminium) chloride (BL-0655; D4)

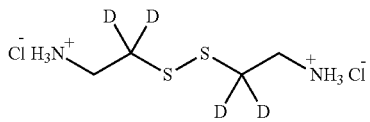

At 0° C., a solution of HCl (4N in 1,4-dioxane, 1.6 mL) was added to a solution of di-tert-butyl(disulfanediylbis(ethane-2,1-diyl-2,2-d2))dicarbamate (0.040 g, 0.112 mmol, 1.00 equiv) in methanol (0.4 mL). The reaction was stirred at ambient temperature for 2 hours. The reaction was concentrated and lyophilized to get the desired compound in a quantitative yield as a white solid (0.025 g, 0.110 mmol). $^1$H NMR (599 MHz, D2O) δ 3.36 (s, 4H) ppm, $^{13}$C NMR (151 MHz, D₂O+MeOH as internal standard) δ 37.37 ppm. HRMS (ES$^+$) calculated for $C_4H_9D_4N_2S_2$ [M+H]$^+$ 157.0766, found 157.0769.

2-mercaptoethan-2,2-d₂-1-aminium chloride (BL-0656)

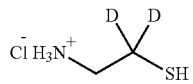

At 0° C., a solution of HCl (4N in 1,4-dioxane, 0.6 mL) was added to a solution of tert-butyl (2-mercaptoethyl-2,2-d2) carbamate (0.015 g, 0.084 mmol, 1.00 equiv) in methanol (0.15 mL). The reaction was stirred at ambient temperature for 2 h. The reaction was concentrated and lyophilized to afford the desired compound in a quantitative yield as a white solid (0.015 g, 0.112 mmol). $^1$H NMR (599 MHz, D₂O) δ 3.17 (s, 2H) ppm; $^{13}$C NMR (151 MHz, D₂O+ MeOH as internal standard) δ 41.67 ppm. HRMS (ES$^+$) calculated for $C_2H_6D_2NS$ [M+H]$^+$ 80.0498, found 80.0498.

Additional syntheses:

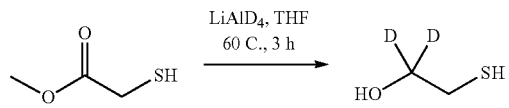

To a solution of LiAlD₄ (870 mg, 20.73 mmol, 1.1 eq) in THF (40 mL) at 0° C. was added methyl 2-mercaptoacetate (1.686 mL, 18.84 mmol, 1 eq) dropwise. The mixture was then heated at 60° C. for 3 h (check completion by TLC (hex/EtOAc (7/3)). The mixture was quenched by addition of a 1M HCl solution and EtOAc at 0° C. and the mixture was stirred for an additional hour at r.t. The aqueous layer was extracted twice with EtOAc and the combined organic fractions were washed twice with brine, dried and concentrated under reduced pressure to furnish 2-mercaptoethan-1,1-d2-1-ol (910 mg, 11.4 mmol, 60.3%) as a light-yellow oil, which was used in the next step without further purification.

$^1$H NMR (600 MHz, Chloroform-d) δ 2.71 (d, J=6.0 Hz, 2H), 1.98(bs, 1H), 1.38 (t, J=6.0 Hz, 1H).

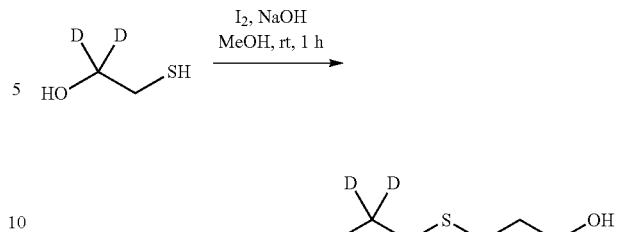

2-mercaptoethan-1,1-d2-1-ol (1.63 g, 20.44 mmol, 1 eq) was dissolved in methanol (20 mL), followed by addition of a 1M NaOH solution (17 mL, 51.10 mmol, 2.5 eq), and iodine (3.113 g, 12.26 mmol, 0.6 eq) was added after partial dimerization occurred after an hour. The reaction was then extracted with ethyl acetate and the organic layers were washed with sodium thiosulfate 10% and brine, dried and concentrated to furnish 2,2'-disulfanediylbis(ethan-1,1-d₂-1-ol) (1.46 g, 9.2 mmol, 90%) which was used in the next step without further purification.

$^1$H NMR (600 MHz, Chloroform-d) δ 2.87 (s, 4H), 2.13 (bs, 2H).

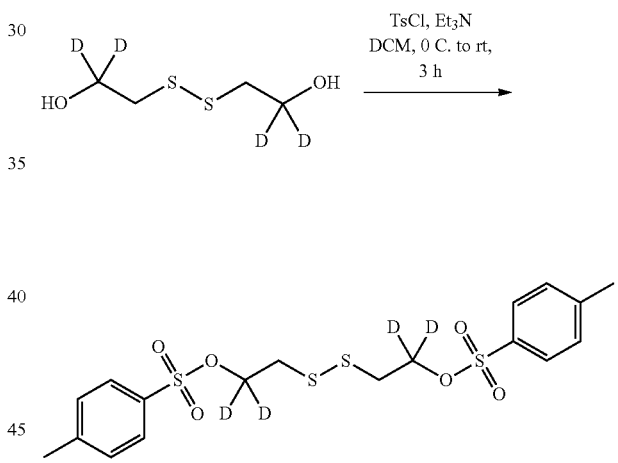

To a solution of 2,2'-disulfanediylbis(ethan-1,1-d2-1-ol) (640 mg, 4.04 mmol, 1 eq) in DCM (50 mL) at 0° C. was successively added 4-methylbenzenesulfonyl chloride (2.31 g, 12.1 mmol, 3 eq) and triethylamine (2.28 mL, 16.2 mmol, 4 eq) and the mixture was allowed to stir at r.t. for 3 h. The reaction media was quenched by addition of water, the aqueous layer was extracted twice with DCM and the combined organic fractions were washed with 1M HCl and brine, dried and concentrated under reduced pressure. The crude residue was purified over flash chromatography (Biotage 50 g snap, 15 cv, 0-50% EtOAc in hexanes 40 ml/min flow rate) to furnish disulfanediylbis(ethane-2,1-diyl-1,1-d2)bis(4-methylbenzenesulfonate) (1.80 g, 3.86 mmol, 95.4%) as a pale yellow solid.

$^1$H NMR (600 MHz, Chloroform-d) δ 7.78 (d, J=6.0 Hz, 4H), 7.35 (d, J=6.0 Hz, 4H), 2.81 (s, 4H), 2.44 (s, 6H).

$^{13}$C NMR (151 MHz, Chloroform-d) δ 145.27, 132.70, 130.08, 128.03, 36.73, 21.78.

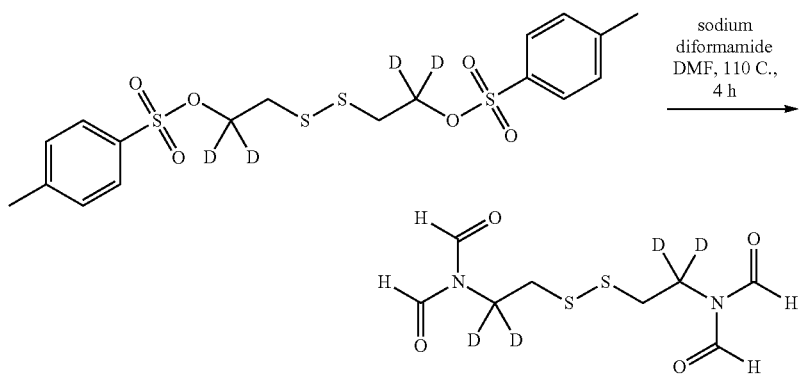

disulfanediylbis(ethane-2,1-diyl-1,1-d2)bis(4-methylbenzenesulfonate) (800 mg, 1.71 mmol, 1 eq) and sodium diformamide (407 mg, 4.29 mmol, 2.5 eq) were dissolved in DMF (5 mL) and left to stir at 110° C. for 4 h. The reaction was cooled to r.t. and water was added (4 ml) and the mixture was extracted with EtOAc. The combined organic extracts were washed with water and brine, dried with MgSO$_4$ and concentrated in vacuo. The crude residue was then purified by Biotage (10 g Snap, 15 cv, 0-100% EtOAc, 15 mL/min) to afford N,N'-(disulfanediylbis(ethane-2,1-diyl-1,1-d2))bis(N-formylformamide) (90 mg, 0.34 mmol, 20%) as a white solid.

$^1$H NMR (600 MHz, Chloroform-d) δ 8.88 (s, 4H), 2.90 (s, 4H).

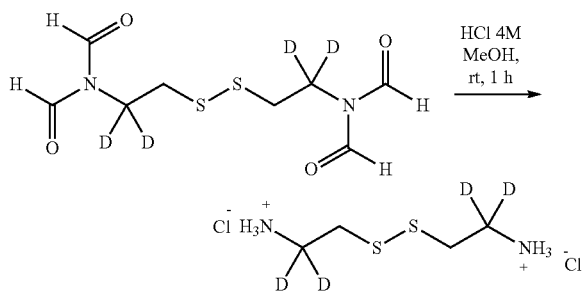

To a solution of N,N'-(disulfanediylbis(ethane-2,1-diyl-1,1-d2))bis(N-formylformamide) (107 mg, 0.399 mmol, 1 eq) in methanol (10 mL) was added hydrogen chloride (1.99 mL, 4 molar, 7.97 mmol, 20 eq) and the mixture was stirred at r.t. for 1 h before it was concentrated to dryness to furnish (D4n-cystamine): 2,2'-disulfanediylbis(ethan-1,1-d2-1-aminium) chloride (91 mg, 0.390 mmol, 99%) as a pale orange solid.

$^1$H NMR (600 MHz, D$_2$O) δ 3.03 (s, 4H).

HRMS (ES+) calculated for $C_{18}H_{17}ClFN_6$ [M−2HCl+H]$^+$ 157.0766, found 157.0766.

In vitro experiments with isotopically enriched cystamine in cystinotic fibroblasts. Fibroblasts from a de-identified cystinotic patient were split 3× from 2 plates into 36 plates. Three different drugs were used for the experiments: cystamine (non-labeled), d2-cystamine, and d4-cystamine. There were two time series for each drug. The first was with constant drug incubation and included: 0, 10 min, 30 min, 1 h, 3 h, and 5 h. The other series included a washout after 3 h drug incubation, using fresh media following a PBS wash, and included the timepoints: 0, 30 min, 1 h, 3 h, 5 h, and 17 h. A direct quench and extraction technique were used for harvesting all cells to minimize further oxidation and metabolism. This included 2× washes with PBS that included 5 mM N-ethylmaleimide for trapping free thiol groups, and then scraping the plates with an acidified organic solvent extraction solution containing both d4-cystine and d4-cysteamine (plus d-8 cystamine) as internal standards. All samples were run on an API 4500 triple quadrupole LC-MS/MS, with selective reaction monitoring (SRM/MRM) for the following compounds of interest: cystine, NEM-cysteamine, NEM-cysteine, cystamine, and 2-(methylthio)ethylamine. All data fit well to single exponential curves (either decay or association), except where mentioned.

Cystine measurement during constant cystamine exposure: Fibroblast cultures were exposed to 100 uM cystamine/d2-cystamine/d4-cystamine for the following timepoints: 0 min, 10 min, 30 min, 1 h, 3 h, and 5 h. Following incubation, cells were washed 2× in PBS containing N-ethylmaleimide. Wash was removed, and cells were harvested on ice using 80% acetonitrile/1% formic acid, containing stable isotope internal standards for cystine (d4-cystine) and cysteamine (d4-cysteamine and d8 cystamine).

Figure 6:
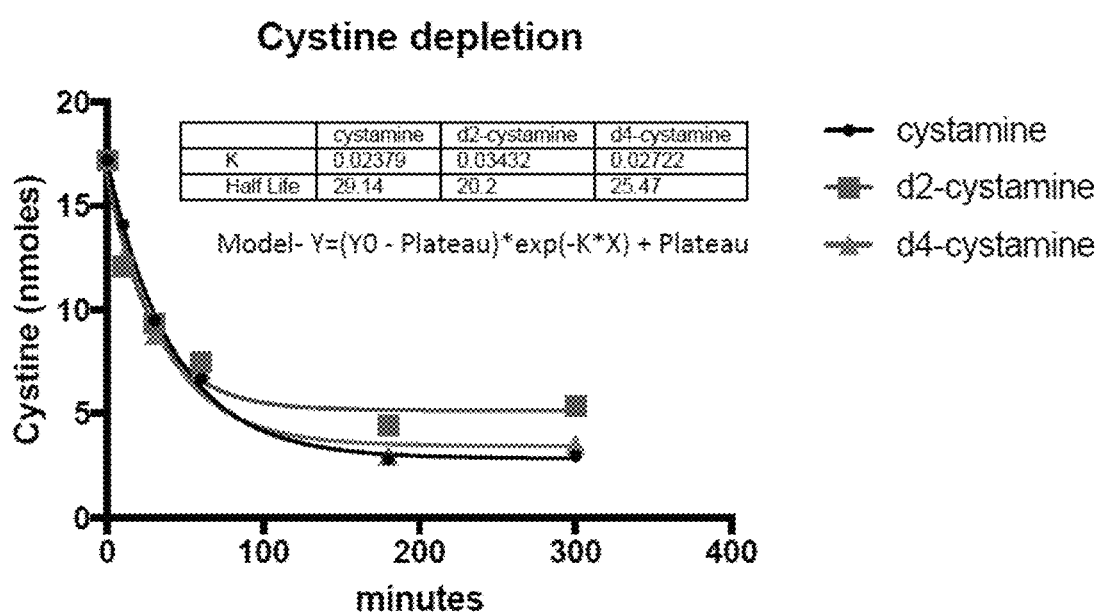
FIG. 6 presents the results of a cystine depletion study with cystamine, $d_2$-cystamine, and $d_4$-cystamine in dermal fibroblasts isolated from a cystinotic patient "cystinotic fibroblasts". As shown, the difference in depletion rates is nearly identical between cystamine and $d_4$-cystamine. $d_2$-Cystamine showed slightly slower kinetics.

As shown in FIG. 6, the difference in cystine depletion rates were nearly identical between cystamine and d4-cystamine. D2-cystamine showed slightly slower kinetics, but this may be within error, especially considering that d4-cystamine showed a slightly faster depletion rate.

Cystine measurement after washout: Fibroblast cultures were exposed to 100 uM cystamine/d2-cystamine/d4-cystamine for 3 h. Following incubation, cells were washed with PBS, and then incubated with regular media (containing FBS) for the following timepoints: 0 min, 30 min, 1 h, 3 h, 5 h, and 17 h. Cells were harvested identically as described previously.

Figure 7A:
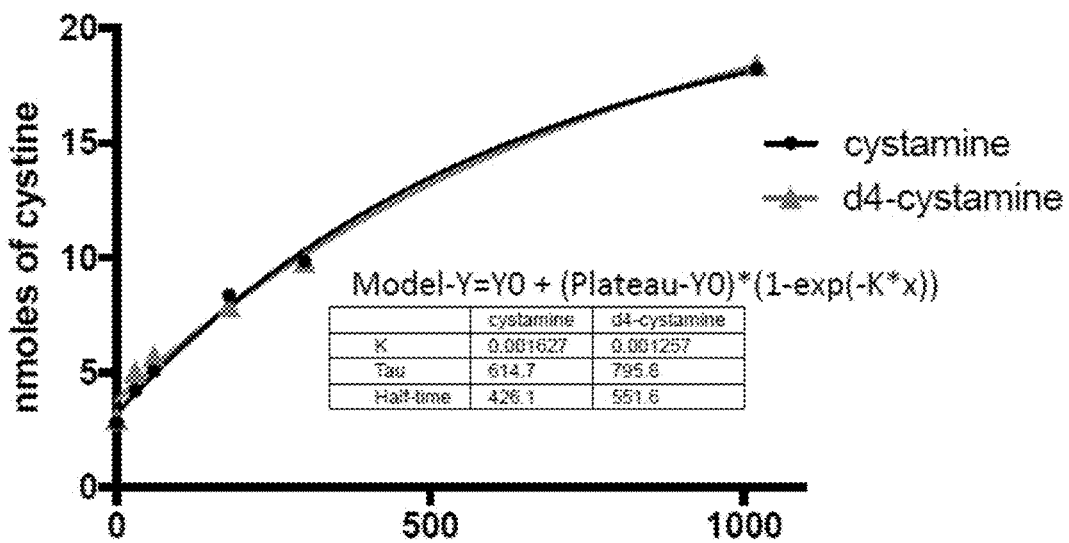
FIG. 7A-B presents the results of cystine re-accumulation in washed cystinotic fibroblasts that were previously administered cystamine, $d_2$-cystamine, and $d_4$-cystamine. One phase exponential association curve was fit to each set of data points (note: Tau, shown in the tables represents the inverse of K). Cystine re-accumulation between cystamine and $d_4$-cystamine are very similar (A). Though $d_2$-cystamine appears slightly faster (B), this could be due to this latter experiment being performed on a different day than the other 2, and using more confluent cells. In both cases, however, the cystine levels took 10-17 h to reaccumulate back to baseline levels, which is longer than would be expected for cysteamine.
Figure 7B:
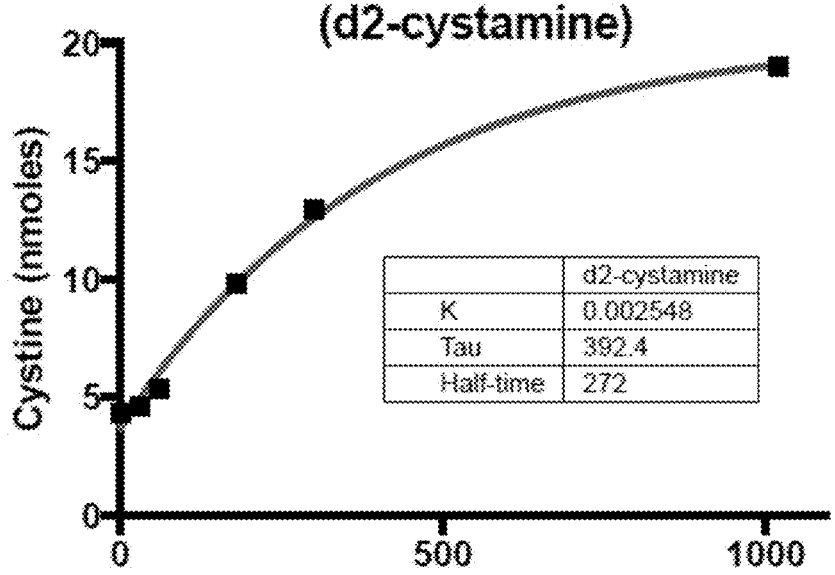

As shown in FIG. 7A-B, cystine re-accumulation between cystamine and d4-cysteamine are very similar. Though d2-cystamine appears slightly faster, this could be due to this latter experiment being performed on a different day than the other 2, and using more confluent cells.

NEM-cysteamine and NEM-cysteine during constant incubation. Fibroblast cultures were exposed to drug (either cystamine, d2-cystamine, or d4-cystamine) and harvested as described on page 2 for the cystine depletion curve. NEM-cysteamine (or NEM-d1-cysteamine or NEM-d2-cysteamine) was measured for each respective plate and normalized against the signal for d4-cystine.

Figure 8A:
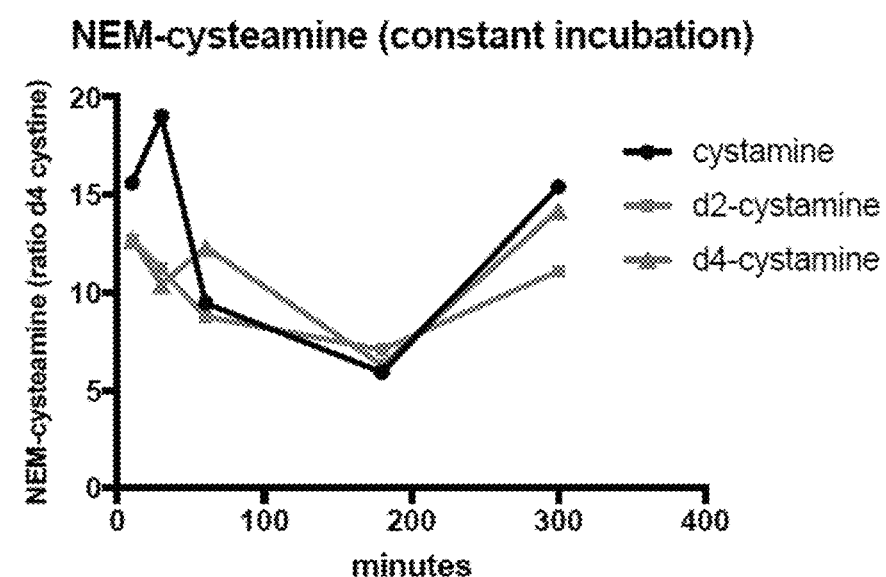
FIG. 8A-B shows studies conducted with NEM-cysteamine and NEM-cysteine during constant incubation. (A) NEM-cysteamine (or NEM-$d_1$-cysteamine or NEM-$d_2$-cysteamine) was measured for each respective plate and normalized against the signal for $d_4$-cystine. Higher levels of cysteamine are again seen (e.g., see FIG. 5B above) at early timepoints following cystamine compared with either of the deuterated molecules and this may result more "controlled" intracellular cysteamine availability and less "free cysteamine" for conversion to noxious metabolites. Levels of NEM-cysteamine trough at 3 h, but then rise again for all drug types during the 5 h exposure. This may be because of later reduction of the previously formed MDS (of cysteamine-cysteine) and would account also for (B) where the levels of cysteine also show a spike from 3 h to 5 h.
Figure 8B:
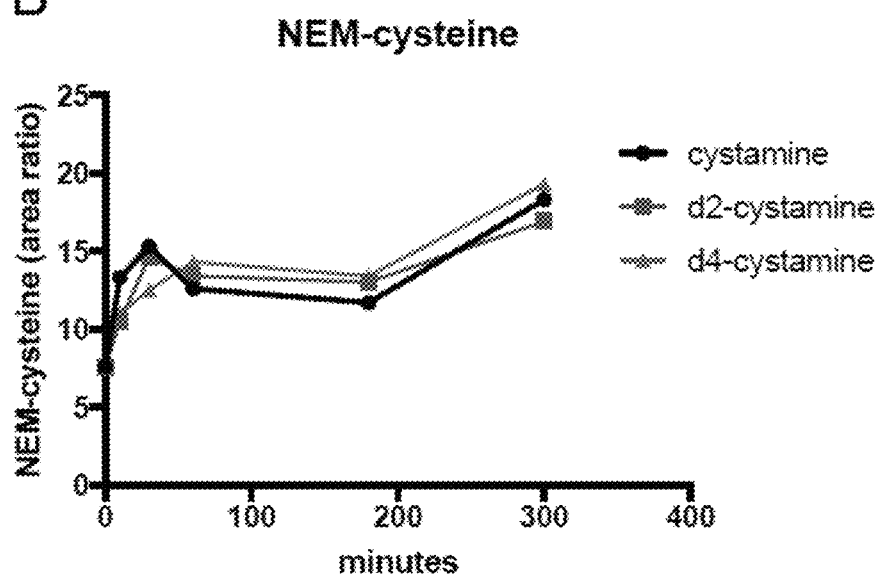

As shown in FIG. 8A-B, during constant drug exposure, the values of NEM-cysteamine appear to differ between drug types. Higher levels are seen at early timepoints, with the highest seen after non-labeled cystamine exposure (e.g., see FIG. 8A). Levels decrease at 3 hours, but then rise again for all drug types during the 5-hour exposure (e.g., see FIG. 8A). The levels of cystine (bottom graph) also show a spike from 3 h to 5 h (e.g., see FIG. 8B).

NEM-cysteamine during washout. Fibroblast cultures were exposed to drug (either cystamine, d2-cystamine, or d4-cystamine) for 3 h were then exposed to media for various timepoints and harvested as previously described.

NEM-cysteine during washout. Fibroblast cultures were exposed to drug (either cystamine, d2-cystamine, or d4-cystamine) for 3 h were then exposed to media for various timepoints and harvested as previously described.

Figure 9:
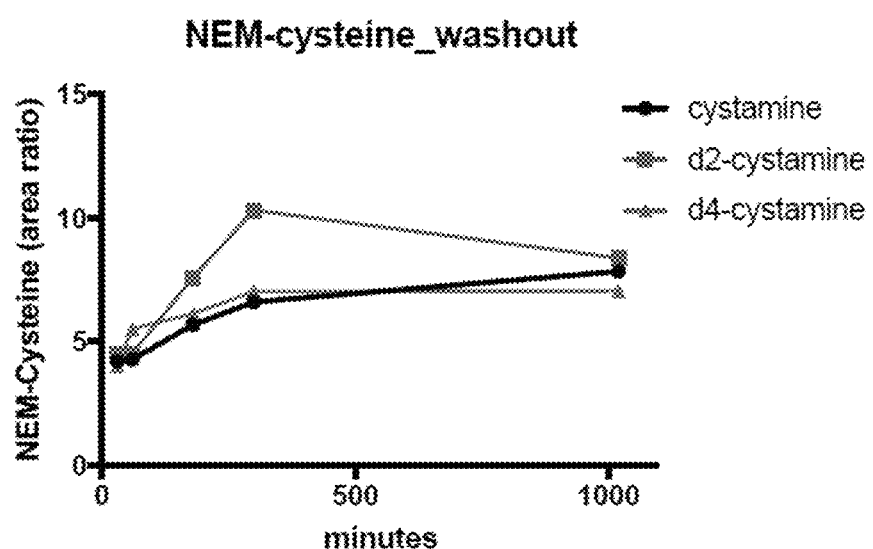
FIG. 9 shows the levels of NEM-cysteine after a 3 h incubation with drug and then a washout. As shown, the NEM-cysteine levels all increase after the washout period for cystamine, $d_2$-cystamine and $d_4$-cystamine.

As shown in FIG. 9, the cysteine levels all rise during course of washout period for cystamine, d2-cystamine and d4-cystamine. D2 porduced higher cysteine levels suggesting that it is more effective in reducing intracellular cystine to cysteine and cysteine-D-cysteamine mixed disulfide.

Cystamine during constant drug incubation. Fibroblast cultures were exposed to drug (either cystamine, d2-cystamine, or d4-cystamine) for various timepoints following harvesting as described earlier. Cystamine could be measured in the non-labeled cystamine incubation as well as the d4-cystamine incubation. d2-cystamine could not be accurately measured due to a strong background interference signal corresponding to that mass. No cystamine could be measured in the washout experiments.

Figure 10:
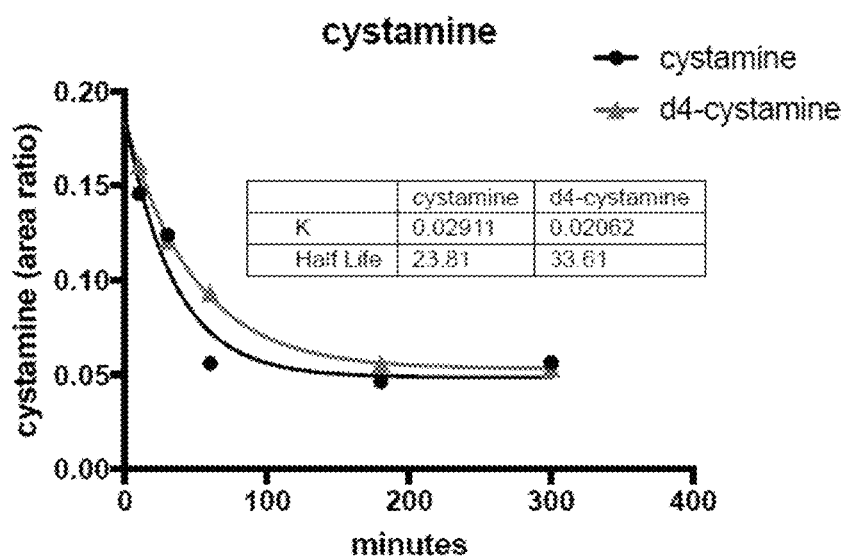
FIG. 10 shows the levels of cystamine and isotopically enriched cystamine in cystinotic fibroblasts during constant drug incubation. Cystamine levels deplete rapidly during constant incubation. At near saturation levels, a plateau is observed.

As shown in FIG. 10, cystamine depletes rapidly during washout. This implies that the drug is getting reduced rapidly in the cells or forming a mixed disulfide. At near saturation levels, additional drug may be slow to enter the cell, hence the plateau after several hours.

Cystine Depletion Studies with D8-Cystamine and D4n-Cystamine. To study the ability of additional deuterated compounds to affect cystine levels, 2 compounds:

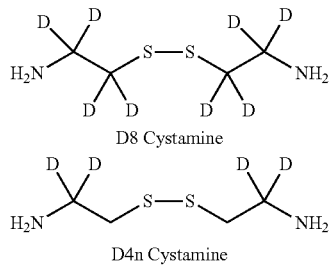

D8 Cystamine

D4n Cystamine were studied.

Fibroblasts from a de-identified cystinotic patient were split 3× from 2 plates into 18 plates. Two different drugs were used for the experiments: D4n-cystamine, and D8-cystamine. There were two time series for each drug. The first was with constant drug incubation and included: 0, 15 min, 30 min, 1 hr, and 3 hr. The other series included a washout after 3 hours of drug incubation, using fresh media following a PBS wash, and included the time-points: 0, 1 hr, 3 hr, and 16 hr. A direct quench and extraction technique was used for harvesting all cells to minimize further oxidation and metabolism. This included 2× washes with PBS that included 5 mM N-ethylmaleimide (NEM) for trapping free thiol groups, and then scraping the plates with an acidified organic solvent extraction solution containing NEM-cysteamine, D4n-cystamine and non-labelled cysteamine as internal standards. All samples were run on an API 4500 triple quadruple LC-MS/MS, with selective reaction monitoring (SRM/MRM) for the following compounds of interest: cystine, NEM-cysteamine, NEM-cysteine, and cystamine. All data fit well to single exponential curves (either decay or association), except where mentioned.

Figure 14:
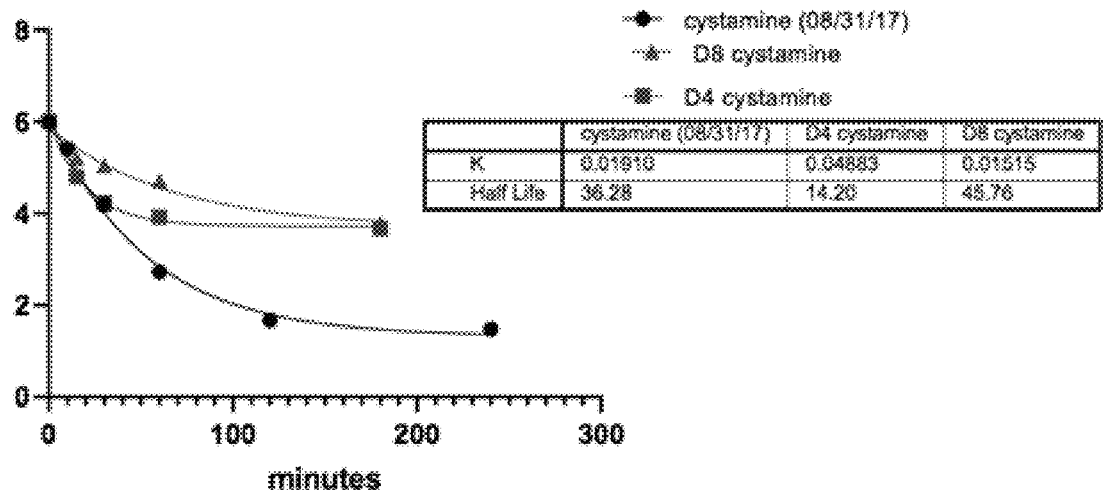
FIG. 14 shows results of a cystine depletion study of D4n and D8 matched with a prior cystamine cystine depletion curve from a prior study.

FIG. 14 shows that D8 cystamine has a longer half-life compared to the D4n cystamine. A sample curve from previous experiments for non-deuterated cystamine is overlayed for reference.

Figure 15:
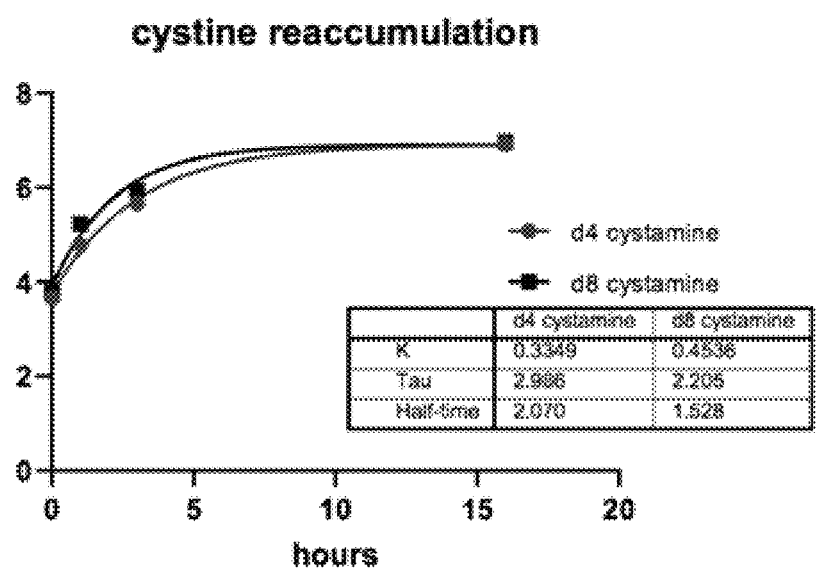
FIG. 15 shows a cystine reaccumulation curve using D4n and D8 cystamine.

Fibroblast cultures were exposed to 50 µM cystamine (D8 or D4n) for 3 hours. Following incubation, cells were washed with PBS and then incubated with regular mediate containing FBS for 1 h, 3 h, and 16 h. Cells were harvested as above. A one phase exponential association curve was fit to each set of data points (note: Tau, shows in the tables represent the inverse of K). Cystine reaccumulation between D4n-cystamine and D8-cystamine are very similar, indicating similar levels of drug remaining during the washout timepoints (FIG. 15).

Figure 16:
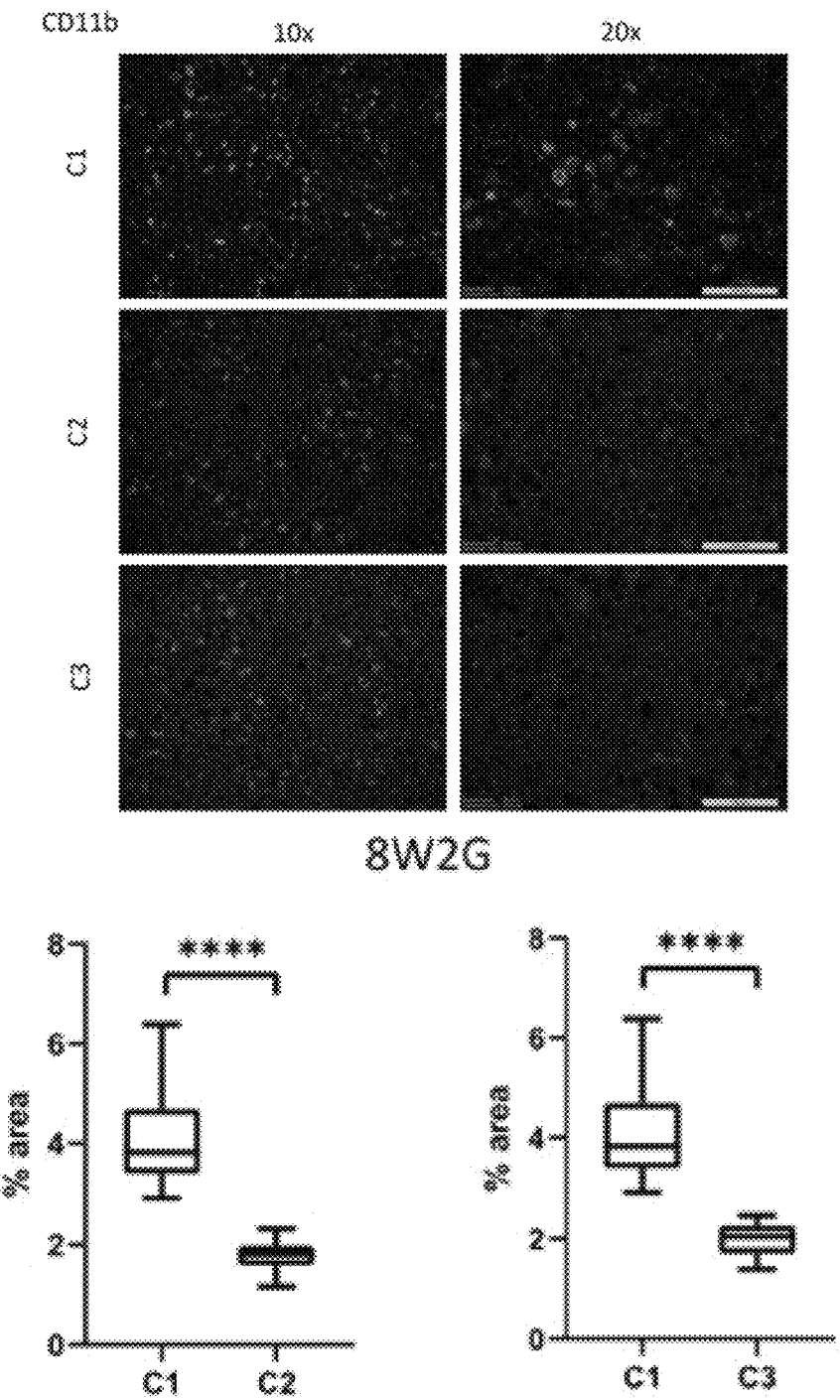
FIG. 16 shows the results of CD11b staining of liver tissue from mice treated with a CDAHFD diet for 8 weeks and then by 2 weeks of gavage with either D2-cystamine or D4 cystamine. Groups: C1—control; C2—2 weeks D2-cystamine 200 mg/kg/day; C3—2 weeks D4-cystamine 200 mg/kg/day.

Liver Inflammatory Cells. CD11b stains macrophages and microglia. CD11b staining of liver tissue was taken after 10 weeks of CDAHFD in three groups of mice. Group 1 control mice ("C1") represents the control group that did not receive drug. At 8 weeks, treatment group 2 ("C2") mice started gavage feeding with D2-Cystamine at 200 mg/kg/day once daily gavage, and treatment group 3 ("C3") mice received D4-Cystamine at 200 mg/kg/day by once daily gavage. There was a statistically significant reduction (p<0.0001) in the number of CD11b positive cells in liver tissue in the mice treated with D2 and D4-cystamine compared with the control group (FIG. 16).

These data make a compelling argument for D2 and D4-cystamine to reverse steatohepatitis as suggested by reduced ALT, reduced fibrosis, reduced Collagen 1 and TIMP expression, reduced steatosis (pericentral) and reduced inflammatory infiltrate (CD11b).

In vitro experiments with isotopically enriched cystamine and cysteamine in hepatocytes. The assessment of in vitro metabolic stability of each of the deuterated and non-deuterated cysteamine and cystamine compounds was conducted via hepatocyte stability studies.

The assessment of in vitro metabolic stability provides a means to measure the susceptibility of a test compound to biotransformation by the liver. While liver microsomes primarily assess cytochrome P450 system-mediated metabolism (phase I metabolism), hepatocytes represent a complete, undisrupted metabolic system, including cofactors, and thus assess both phase I and phase II metabolism. In all cases, the metabolic stability of test compounds was determined by monitoring, via LC/MS/MS, the percent parent compound remaining versus time of incubation in human hepatocytes.

Pooled human hepatocytes (catalog number HMCS10, ThermoFischer Scientific) were thawed according to the manufacturers instructions. Thawed hepatocytes were washed by centrifugation and replated in Williams' Medium E supplemented with Heptocyte Plating Supplement Pack, Serum-containing.

Cells were diluted to 1,000,000 per ml in maintenance media (Williams' E Media supplemented with Hepatocyte Maintenance Supplement Pack, Serum-free). 500 µl of cell suspension was added to each well of a microtiter plate containing 500 µl of the deuterated test agent and placed on an orbital shaker at 120 rpm at 37 C. At the appropriate time point 50 µl aliquots were removed from the well and added to 50 µl of ice cold ethyl acetate and vortexed for 5 min and froze until chromatography analysis.

The data are presented in Table 1 (above). The hepatocyte elimination studies show that D4-Cystamine is the most stable of the dimeric compounds. This is why D4 results in a higher AUC and Cmax (for its monomer form) compared with D2 and cystamine and also reduced rate of elimination in the hepatocyte elimination studies.

In addition, Table 1 shows that compared to non-deuterated cysteamine and cystamine, the deuterated forms have a slower hepatocyte clearance.

In vivo NASH Models. NASH models from normal C57BL/6 male mice on CDAHFD diet (choline deficient, L-amino acid defined, high fat diet with restricted amount of methionine) were used. Two deuterated cystamine molecules were tested:

| Structure | Name |
|---|---|
| $H_2N\text{-CHD-CH}_2\text{-S-S-CH}_2\text{-CHD-NH}_2$ | D2 or BL-0647 |
| $H_2N\text{-CD}_2\text{-CH}_2\text{-S-S-CH}_2\text{-CD}_2\text{-NH}_2$ | D4 or BL-0655 |

Two phase study was performed: (1) A prevention and (2) a treatment phase. 48 Mice were separated into nine groups of mice as described below. Histology at end of each study was performed looking for specific features of NASH (steatohepatitis, ballooning, fibrosis). The primary endpoint was plasma ALT measurement. Gene expression studies for fibrosis, inflammation were also performed.

Drug (D2 or D4) was administered in drinking water at a concentration to deliver animals about 200 mg/kg/day of drug. Daily weight. Volume of fluid drunk/day was also measured.

Prevention Phase. Group 1: Control mice on CDAHFD for 8 weeks. Blood drawn at 0, 4, and 8 weeks. Group 2: Mice on CDAHFD plus D2 at 200 mg/kg/day for 8 weeks. Blood drawn at 0, 4, and 8 weeks. Group 3: Mice on CDAHFD plus D4 at 200 mg/kg/day for 8 weeks. Blood drawn at 0, 4, and 8 weeks. Group 4: Control mice (n=4) continue on CDAHFD for 2 weeks. Blood at baseline and at 2 weeks. Liver histology at 2 weeks. Group 5: Mice (n=4) on CDAHFD for 2 weeks plus D2 at 200 mg/kg/day administered via daily gavage. Blood at 0 and 2 weeks and histology at 2 weeks. Group 6: Mice (n=4) on CDAHFD for 2 weeks plus D4 at 200 mg/kg/day administered via daily gavage. Blood at 0 and 2 weeks and histology at 2 weeks.

Figure 11:
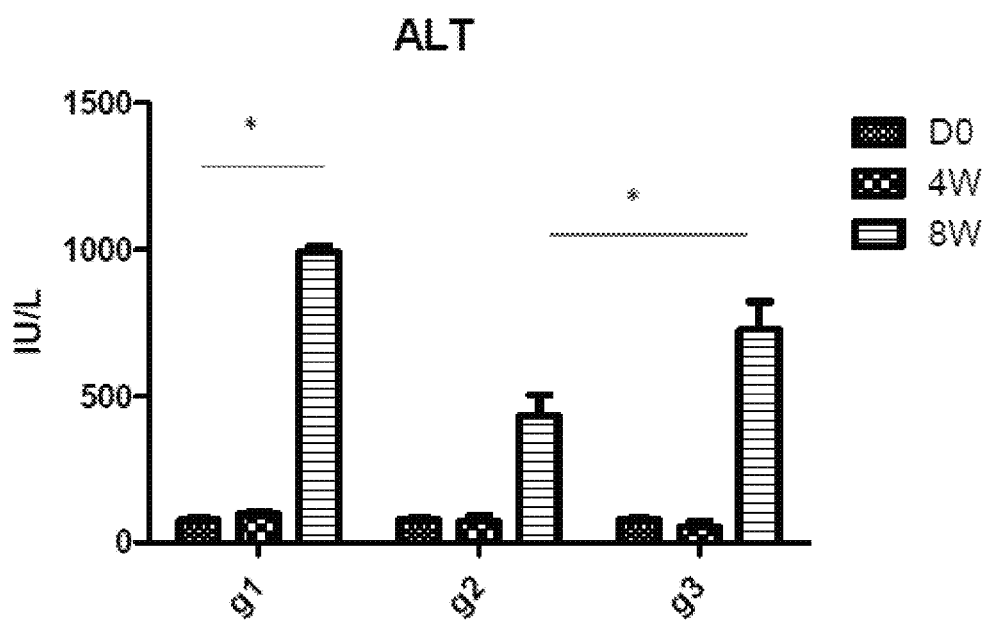
FIG. 11 shows mean ALT levels from mice treated or not treated in an 8 week preventative study of mice fed with CDAFHD, wherein the mice were untreated or with deuterated compounds of the disclosure (n=8 per group) dissolved in water (the amount of water that was drank varied between animals). There was a statistically significant difference for ALT levels at 8 weeks between the control group (g1) and the D2 (g2) therapy but not between the control group and D4 (g3) group. Also there was a statistically significant response between D2 and D4 ALT levels at the 8 weeks treatment ($p<0.01$).
Figure 12A:
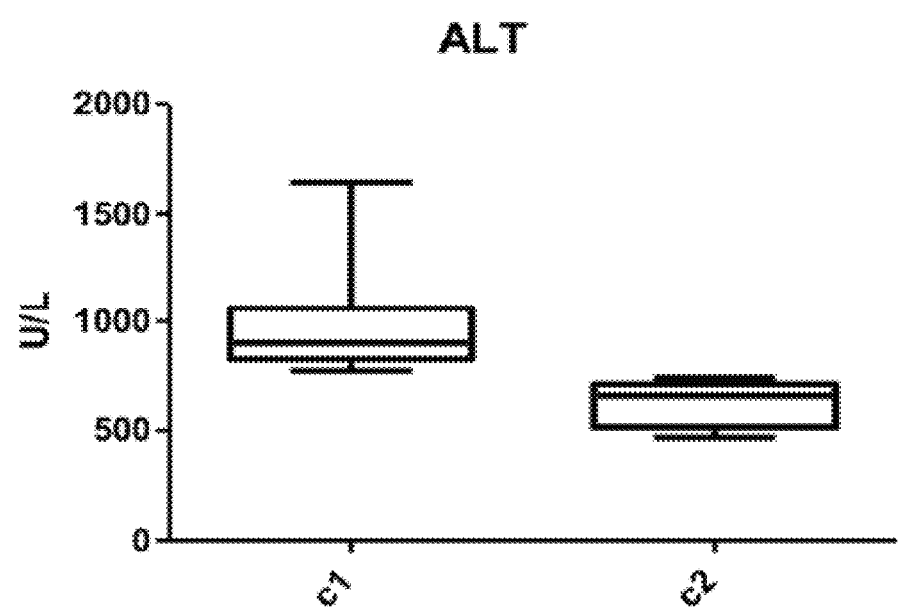
FIGS. 12A-B show a statistical analysis of the group 1 control mice (g1) and either (A) group 2 receiving D2-cystamine (g2) or (B) group 3 mice receiving D4-cystamine (g3) ALT levels.
Figure 12B:
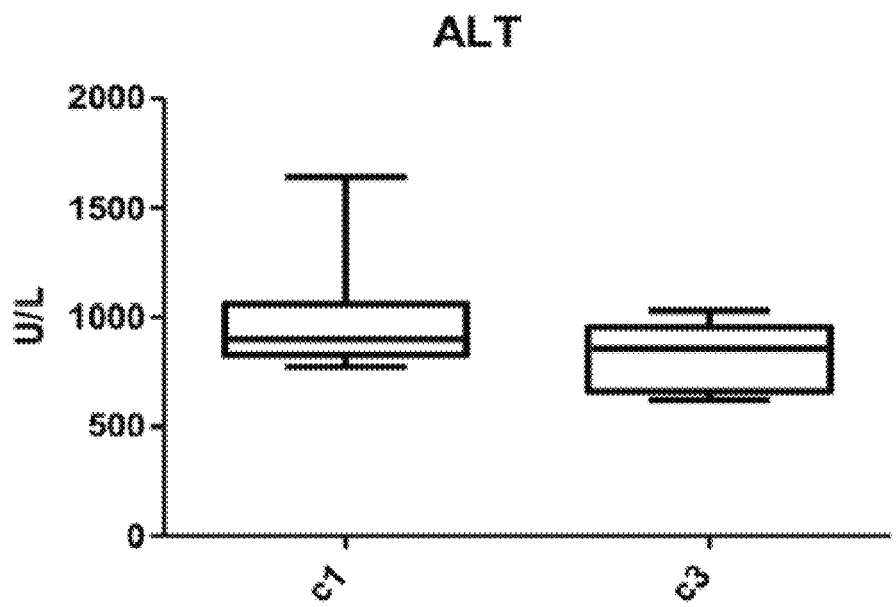

Prevention Study Results. Group 1-3 studied whether deuterated compounds of the disclosure could inhibit or reduce the progression of fatty liver disease in mice. FIG. 11 shows ALT levels of the mice in the group. Group 1 (g1) control mice ALT levels were elevated by week 8 compared to group 2 (g2; D2) and group 3 (g3; D4) mice. Further analysis of the data is presented in FIG. 12, which provides a statistical analysis of group 1 controls compared to group 2 (D2) treated mice. Compared with baseline there were similar changes in weight for the three groups. In the prevention study, it is important to recognize that the drug delivery was not "controlled" but was rather delivered via water consumption by the animals and would vary depending upon the amount of water each animal drank throughout the day.

Treatment Study Results. Groups 4, 5 and 6 mice received 8 weeks of CDAHDF diet before beginning treatment with deuterated compounds of the disclosure. During the treatment phase the mice continued to receive CDAHDF diet. Four mice were set in each group: control (C1) not receiving any drug; treatment (C2) receiving 200 mg/kg of cystamine D2 by once daily gavage; and treatment (C3) receiving 200 mg/kg cystamine D4 by once daily gavage.

Figure 13A:
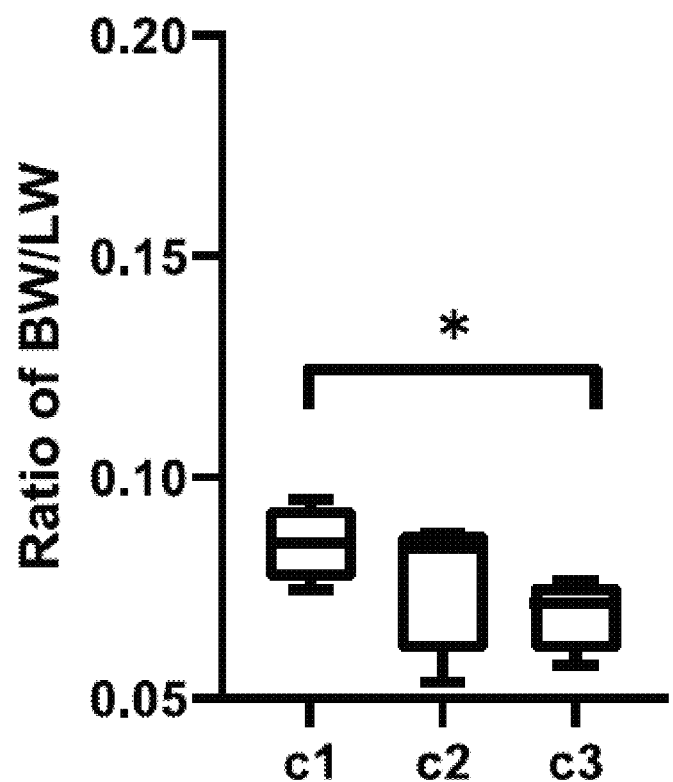
FIG. 13A-D shows results in a cohort of mice receiving controlled delivery via gavage administration of drug in the treatment phase (C1=control; C2=200 mg/kg D2 compound for 2 weeks; C3=200 mg/kg D4 for 2 weeks). (A) Shows the ratio of Body Weight (BW) to Liver Weight (LW). (B) Depicts the ALT levels measured in NALFD mice following 2 weeks of treatment. (C) Shows Sirius Red staining following two weeks of treatment. (D) Shows qPCR results for collagen 1 expression and tissue inhibitor of metalloproteinase (TIMP) following 2 weeks of treatment.
Figure 13B:
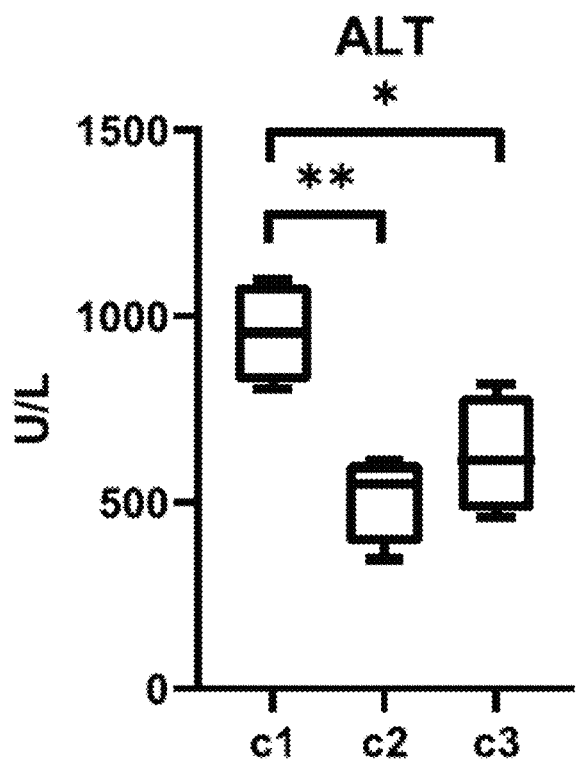
Figure 13C:
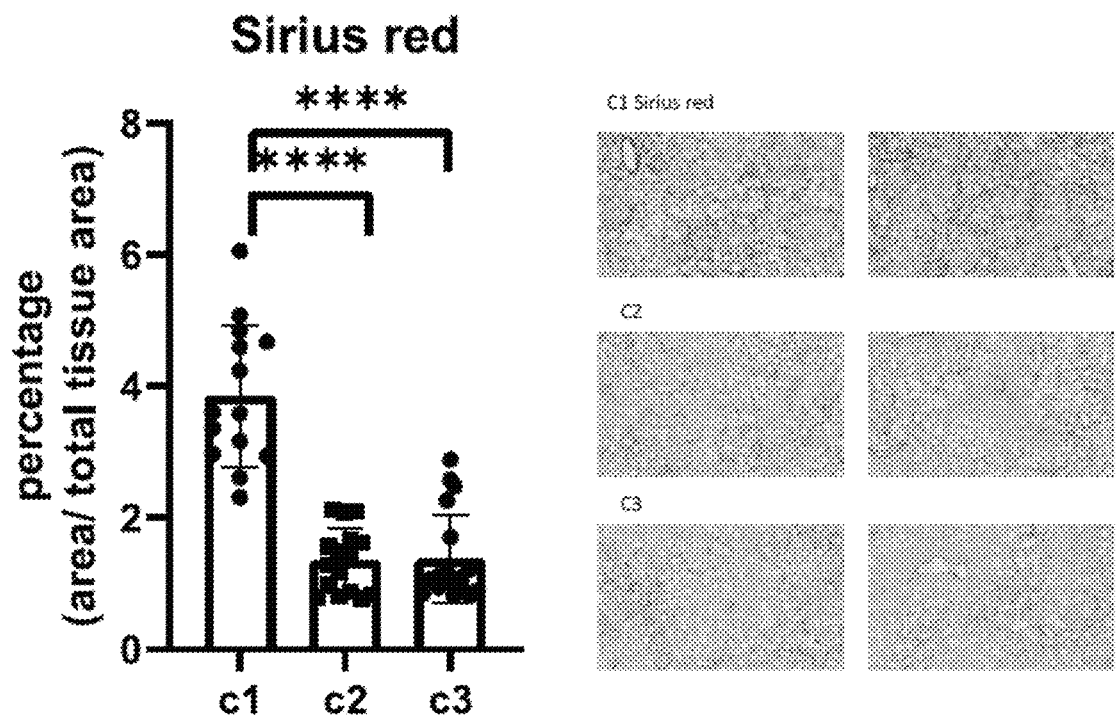
Figure 13D:
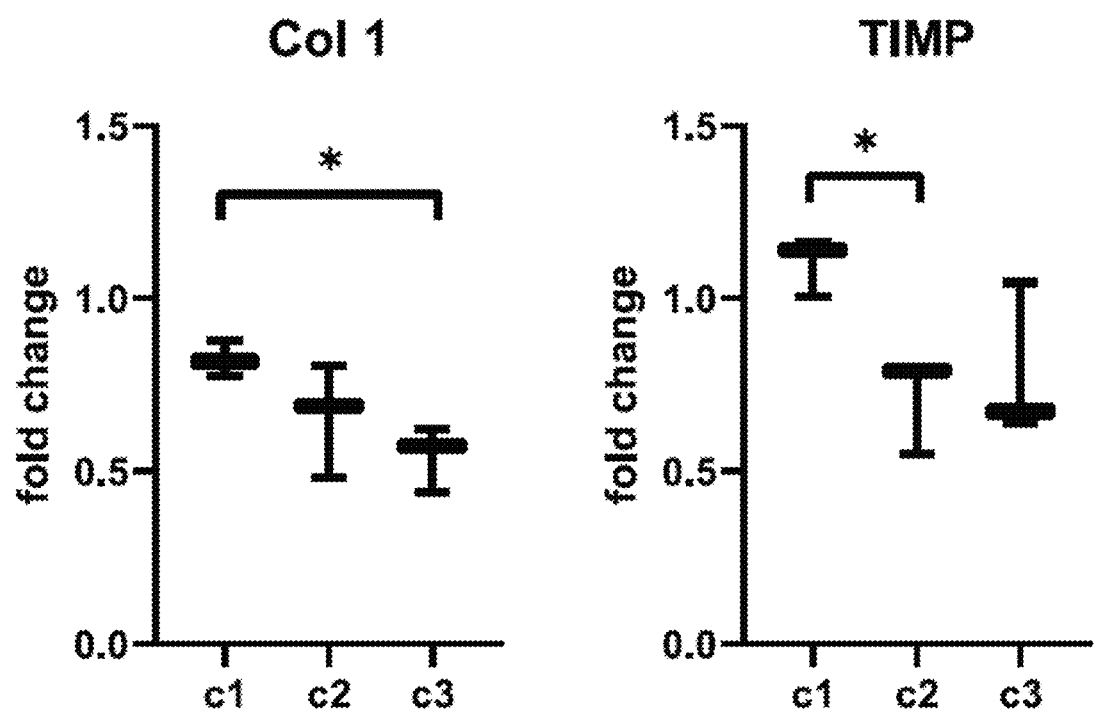

FIG. 13A-D show results obtained from this treatment study. FIG. 13A shows the ratio of Body weight (BW) to liver weight (LW) (BW/LW) at the end of study. Although liver weight (and fat content) are less in C2 and C3 compared with control, only C3 is statistically significant compared to control (C1) (p=0.039) (C1 vs. C2 (p=0.42)). ALT reduction was significantly lower for C2 and C3 when compared with untreated control group (C1 vs. C2 (p=0.0029); C1 vs C3 (p=0.0214); and C2 v C3 (p=0.53)) (FIG. 13B). FIG. 13C shows Sirius Red staining of liver sections. Sirius Red stains for collagen and therefore provides a measure of fibrosis. As can be seen there was a very significant reduction in hepatic fibrosis noted after 2 weeks of daily gavage administration of 200 mg/kg of cystamine D2 and of cystamine D4 (C1 vs C2 (p=<0.0001); C1 vs. C3 (p<0.0001); and C2 vs. C3 (p=0.99)).

Liver fibrosis is associated with the increased expression of collagen resulting in the increased production of fibrotic ECM. Collagen is degraded by matrix metalloproteinases (MMPs) which then, along with the Tissue Inhibitors of metalloproteinases (TIMP) play a role in fibrogenesis and fibrolysis. qPCR analysis of collagen 1 (col 1) and TIMP showed a significant reduction of collagen 1 (C1 vs. C3, p=0.0113) and TIMP (C1 vs C2, p=0.0159) (See, FIG. 13D). Collagen 1 is a more useful marker of fibrosis than TIMP. In all treatment groups there was a reduction in expression of col 1 and TIMP.

Figure 17:
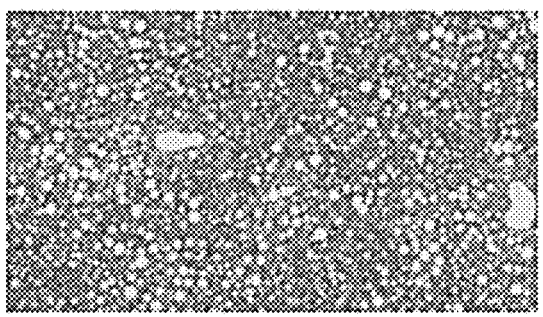
FIG. 17 show liver images stained with H&E showing cells and fat globules. C1—control; C2—2 weeks D2-cystamine 200 mg/kg/day; C3—2 weeks D4-cystamine 200 mg/kg/day. C2 and C3 sections show a reduction in fatty globules, particularly around the veins.
Figure 17:
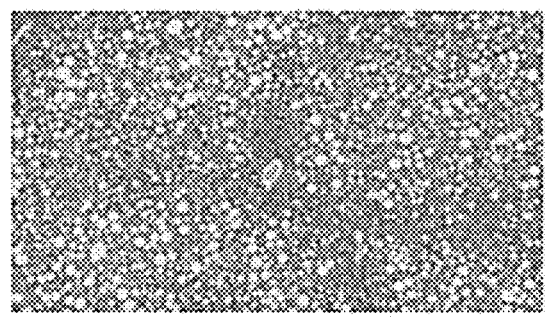
Figure 17:
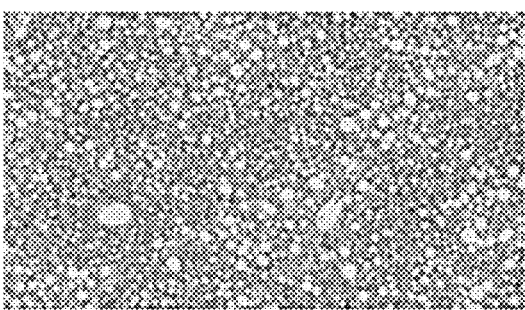
Figure 17:
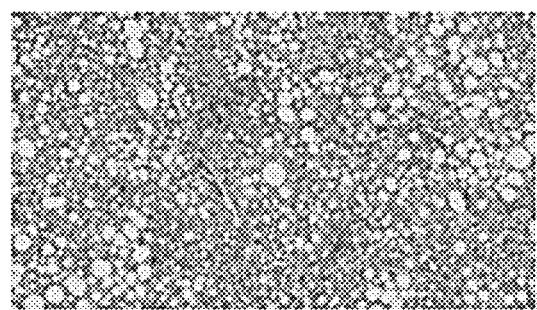
Figure 17:
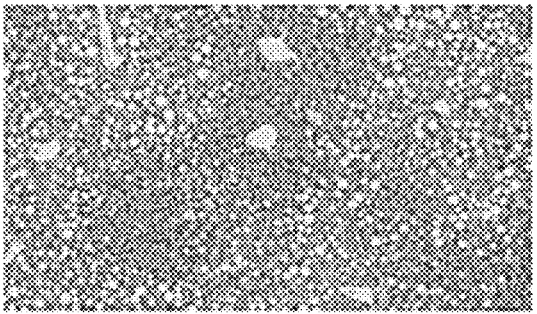
Figure 17:
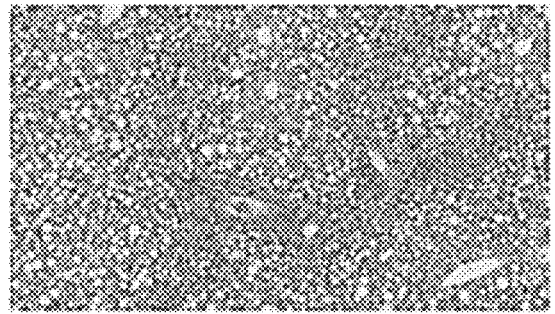

The treatment groups showed significant reduction in the amount of positive liver staining in the D2 and D4 treated groups. There appears to be less pericentral fibrosis in the D4 treated liver (see, FIG. 13C). The data from this staining, as well as reduced expression of collagen 1 (col 1) and TIMP (FIG. 13D) show that the deuterated compounds are reducing established hepatic fibrosis despite continuous CDAHFD. Furthermore, H&E staining showed that the treatment groups had reduced fatty deposits compared to control (see, FIG. 17). This reduction is particularly apparent in D4 group.

Pharmacokinetics of Cystamine in Rats. This study was performed to compare the PK of cysteamine, cystamine D2 and cystamine D4. Because cystamine is reduced to cysteamine the whole blood sample was mixed with NEM to prevent any further interchange between the base molecule and its cysteamine counterpart.

A pilot study was performed with 3 animals to determine whether the methodology was acceptable. (1) 2 rats were used for pilot study, each animal received a different dose of cystamine (200 mg/kg, and 300 mg/kg). (2) Plasma was obtained at 4 time-points per rat, all taken on the same day as drug administration (20 min, 40 min, 60 min, and 2 hrs). The plasma concentration of both cyteamine and cystamine were measured. The experiment showed that the pK profile for cystamine and its cysteamine counterpart are very similar, thus providing sufficient findings that the measurements were effective.

In the experimental study 5 Sprague Dawley rats were used: 2 rats were used for control (non-deuterated cystamine) and 3 rats were used for the study compound (D4 cystamine).

Blood was sampled at 0, 20 min, 40 min, 1, 2, 4 and 6 hours (7 total samples per rat). Approximately 160 µl of whole blood was collected into an EDTA retro-orbital blood collection tube and briefly mixed to insure uniform mixing of EDTA. The blood was quickly transferred into a clean ependorf tube containing 40 μl of fresh 150 mM NEM, mixed and incubated at room temperature for 10 minutes. The Eppendorf tube was centrifuged at 3000 rmp for 5 minute sto pellet RBC and collect plasma into a fresh Eppendorf tube. The volume of the plasma was measured by pipette. Formic acid was added to the plasma to a concentration of 1% and mixed. Table 3 provides the results.

TABLE 3

| Treatment_Group | Cmax (uM) | AUC to last measured concentration (uM*min) | AUC to infinity (uM*min) |
|---|---|---|---|
| Cystamine | 24.3335431 | 3093.201166 | 3368.707455 |
| Cystamine | 25.37608817 | 2322.574721 | 2342.526012 |
| D4-Cystamine | 52.17672805 | 3035.853202 | 3150.092475 |
| D4-Cystamine | 41.39174491 | 4154.143605 | 4388.55606 |
| D4-Cystamine | 61.42765806 | 6369.422555 | 6416.259205 |
| Cystamine group average | 24.85481563 | 2707.887943 | 2855.616734 |
| D4-Cystamine group average | 51.665377 | 4519.806454 | 4651.635913 |

The PK studies show that treatment with D4 cystamine results in higher concentration (Cmax of ~50 uM) of D2-cysteamine compared to non-deuterated cystamine that produce approximately 24 μM of the corresponding monomer (cysteamine). This suggests that the conversion of D4-cystamine to D2-cysteamine is relatively efficient.

The AUC measurements for D4-cystamine derived D2-cysteamine were much higher than cystamine derived cysteamine.

It will be understood that various modifications may be made without departing from the spirit and scope of this disclosure. Accordingly, other embodiments are within the scope of the following claims.

What is claimed:

1. A compound having the structure of Formula I or Formula II:

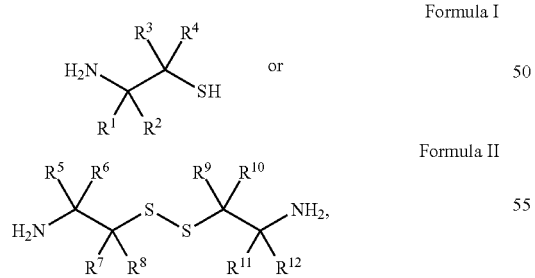

Formula I

Formula II or a pharmaceutically acceptable salt, solvate thereof, wherein:

$R^1$-$R^{12}$ are independently selected from H or D; wherein at least one of $R^1$-$R^4$ is D, and wherein at least one of $R^5$-$R^{12}$ is D, with the proviso that the compound is not selected from the group consisting of:

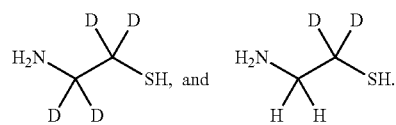

2. The compound of claim 1, wherein at least one of $R^1$-$R^{12}$ independently has deuterium enrichment of no less than about 10%.

3. The compound of claim 1, wherein at least one of $R^1$-$R^{12}$ independently has deuterium enrichment of no less than about 50%.

4. The compound of claim 1, wherein at least one of $R^1$-$R^{12}$ independently has deuterium enrichment of no less than about 90%.

5. The compound of claim 1, wherein at least one of $R^1$-$R^{12}$ independently has deuterium enrichment of no less than about 98%.

6. The compound of claim 1, wherein the compound has a structural formula selected from the group consisting of:

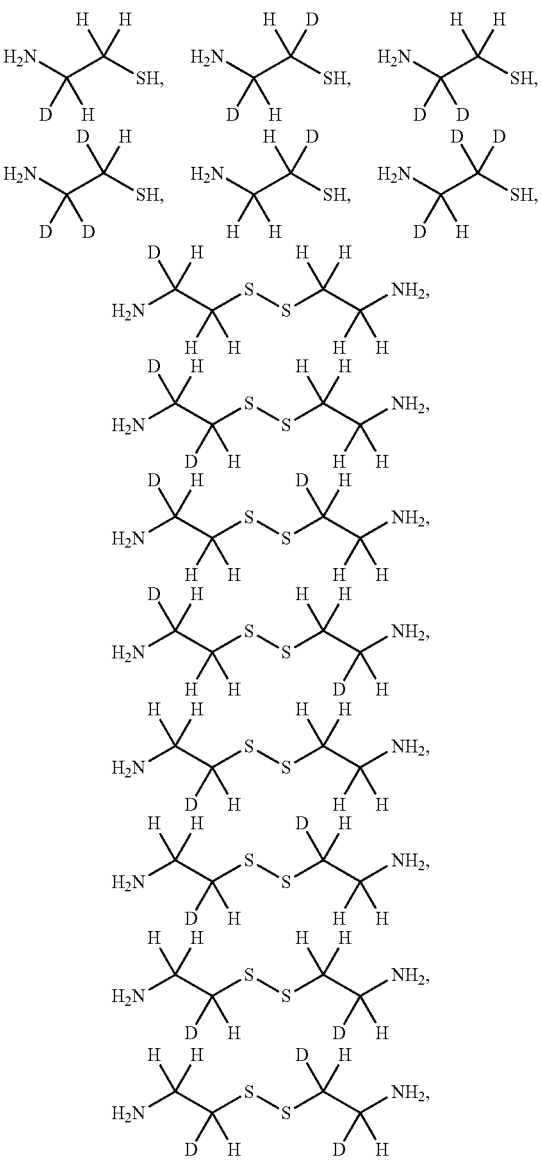

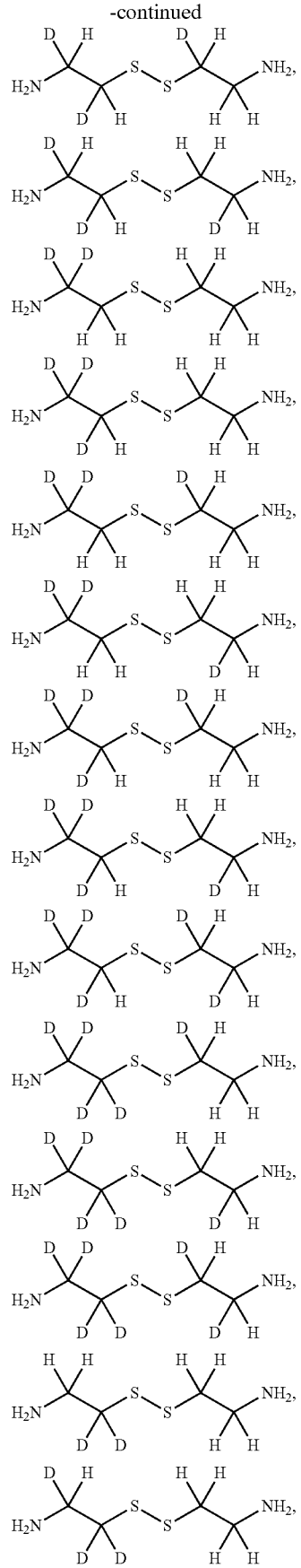
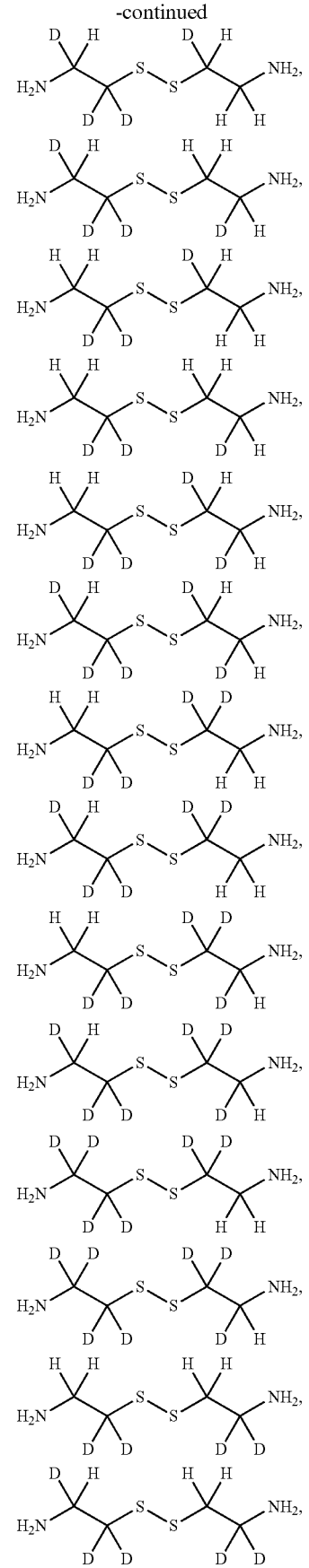

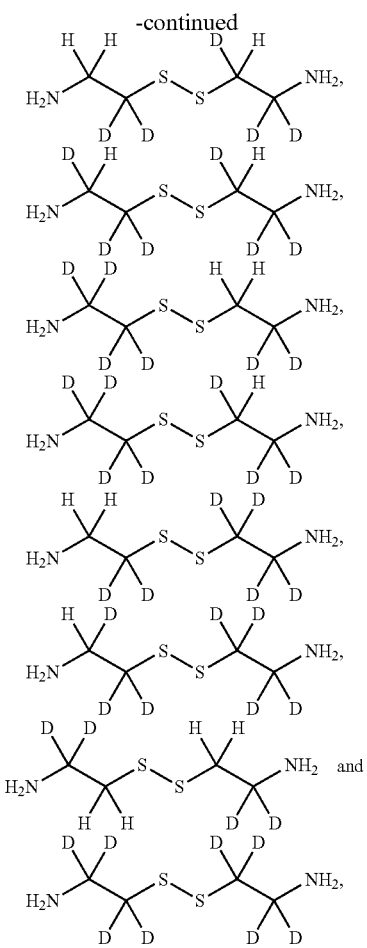

or a pharmaceutically acceptable salt, or solvate thereof.

7. The compound of claim 1, wherein the compound has a structure of:

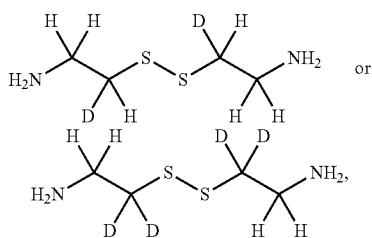

or a pharmaceutically acceptable salt, solvate, or prodrug thereof.

8. The compound of claim 6, wherein each position represented as D has deuterium enrichment of no less than about 10%.

9. The compound of claim 1, wherein when the compound comprises Formula I it is a pharmaceutically acceptable bitartrate salt form of the compound.

10. The compound of claim 1, wherein in comparison to non-deuterated cysteamine or cystamine the compound exhibits at least one effect selected from the group consisting of:
   (a) decreased inter-individual variation in plasma levels of said compound or a metabolite thereof as compared to non-deuterated cysteamine or cystamine;
   (b) increased average plasma levels of said compound per dosage unit thereof as compared to non-deuterated cysteamine or cystamine;
   (c) decreased average plasma levels of at least one metabolite of said compound per dosage unit thereof as compared to non-deuterated cysteamine or cystamine;
   (d) increased average plasma levels of at least one metabolite of said compound per dosage unit thereof as compared to non-deuterated cysteamine or cystamine; and
   (e) an improved clinical effect during the treatment in the subject per dosage unit thereof as compared to non-deuterated cysteamine or cystamine.

11. The compound of claim 1, wherein in comparison to non-deuterated cysteamine or cystamine the compound exhibits at least two effects selected from the group consisting of:
   (a) decreased inter-individual variation in plasma levels of said compound or a metabolite thereof as compared to non-deuterated cysteamine or cystamine;
   (b) increased average plasma levels of said compound per dosage unit thereof as compared to non-deuterated cysteamine or cystamine;
   (c) decreased average plasma levels of at least one metabolite of said compound per dosage unit thereof as compared to non-deuterated cysteamine or cystamine; and
   (d) an improved clinical effect during the treatment in the subject per dosage unit thereof as compared to cysteamine or cystamine.

12. The compound of claim 1, wherein the compound affects a decreased metabolism of the compound per dosage unit thereof by at least one polymorphically-expressed cytochrome $P_{450}$ isoform in a subject, as compared to non-deuterated cysteamine or cystamine.

13. The compound of claim 1, wherein the compound is characterized by decreased inhibition of at least one cytochrome $P_{450}$ isoform or monoamine oxidase isoform in the subject per dosage unit thereof as compared to non-deuterated cysteamine or cystamine.

14. The compound of claim 1, wherein the compound reduces a deleterious change in a diagnostic hepatobiliary function endpoint as compared to non-deuterated cysteamine or cystamine.

15. The compound of claim 14, wherein the diagnostic hepatobiliary function endpoint is selected from the group consisting of alanine aminotransferase (ALT), serum glutamic-pyruvic transaminase (SGPT), aspartate aminotransferase (AST), ALT/AST ratios, serum aldolase, alkaline phosphatase (ALP), ammonia levels, bilirubin, gamma-glutamyl transpeptidase (GGT), leucine aminopeptidase (LAP), liver biopsy, liver ultrasonography, liver nuclear Scan, 5'-nucleotidase, and blood protein.

16. The compound of claim 1, wherein the compound has an increased half-life compared to non-deuterated cystamine or cyteamine.

17. The compound of claim 1, wherein the compound inhibits collagen 1 and TIMP expression and/or reduced fibrosis in non-alcoholic fatty liver disease.

18. The compound of claim 1, wherein the compound remaining after 30 minutes in a hepatocyte elimination studies is greater than 20%, 21%, 22%, 23%, 24% or 25% compared to non-deuterated cystamine or cysteamine.

19. A pharmaceutical composition comprising the compound of claim 1 and a pharmaceutically acceptable carrier, diluent, and/or binder.

20. The pharmaceutical composition of claim 19, wherein the pharmaceutical composition is formulated for oral delivery.

21. The pharmaceutical composition of claim 20, wherein the composition is the in the form of granules, tablet, capsule, or caplet.

22. The pharmaceutical composition of claim 19, wherein the pharmaceutical composition is formulated for delayed release.

23. The pharmaceutical composition of claim 19, wherein the pharmaceutical composition comprises an enteric coating.

24. A method of treating a subject suffering from a disease or disorder selected from the group consisting of cystinosis, fatty liver disease, cirrhosis, an eosinophilic disease or disorder, and Huntington's disease in need of treatment thereof, comprising administering to the subject a therapeutically effective amount of a compound having the structure of Formula I or Formula II:

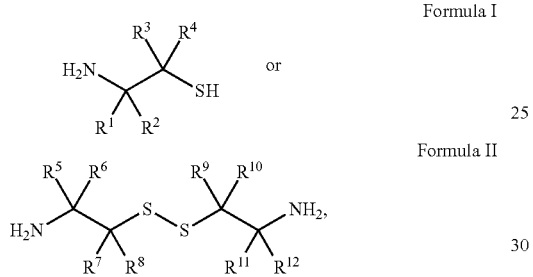

Formula I

Formula II or a pharmaceutically acceptable salt, solvate or prodrug thereof, wherein:
R$^1$-R$^{12}$ are independently selected from H or D; wherein at least one of R$^1$-R$^4$ is D, and wherein at least one of R$^5$-R$^{12}$ is D.

25. The method of claim 24, wherein at least one of R$^1$-R$^{12}$ of the compound independently has deuterium enrichment of no less than about 10%.

26. The method of claim 24, wherein the compound has a structural formula selected from the group consisting of:

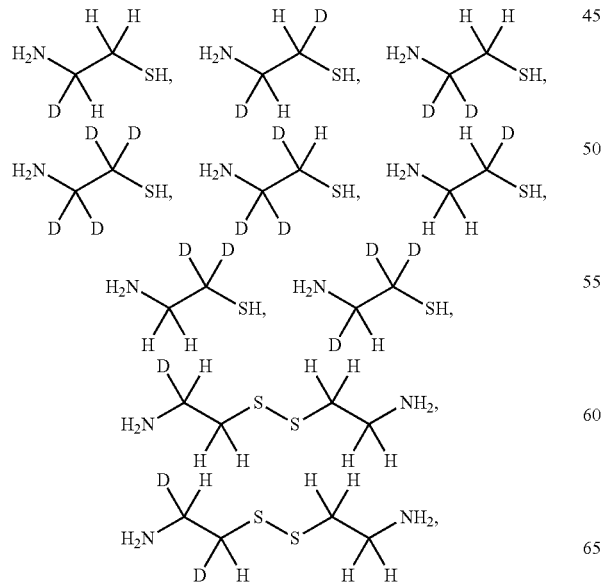

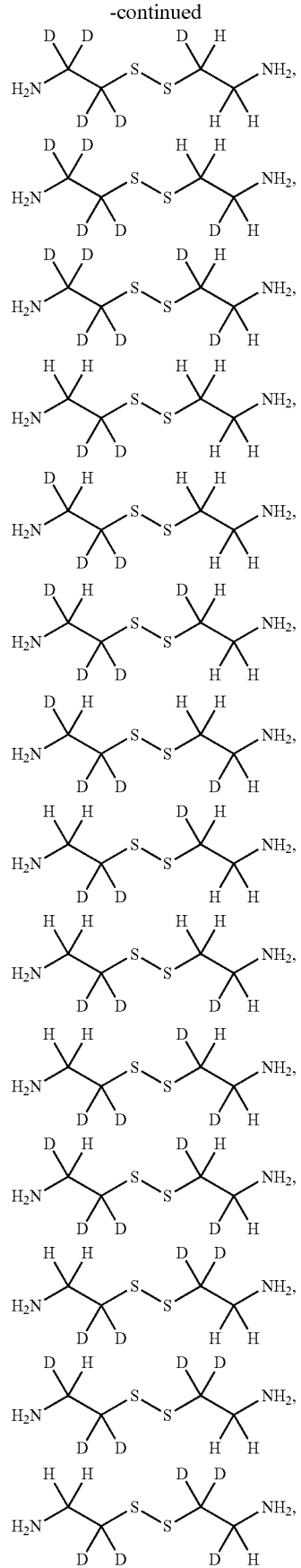
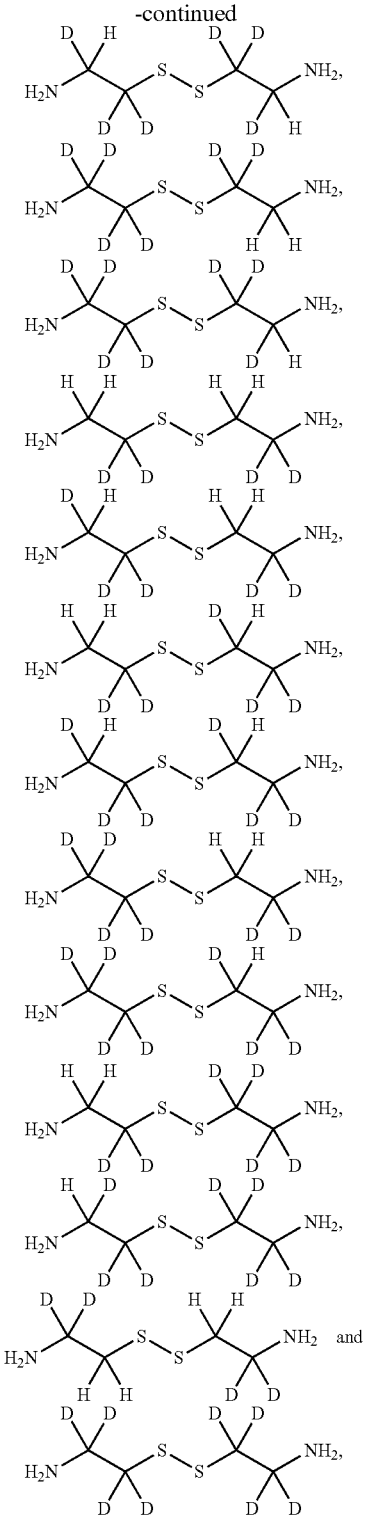
or a pharmaceutically acceptable salt, solvate, or prodrug thereof.
27. The method of claim 26, wherein each position represented as D has deuterium enrichment of no less than about 10%.
28. The method of claim 24, wherein the compound of Formula I is a pharmaceutically acceptable bitartrate salt form of the compound.

29. The method of claim 24, wherein the subject suffers from cystinosis.

30. The method of claim 24, wherein the disease or disorder is a fatty liver disease.

31. The method of claim 30, wherein the fatty liver disease is selected from the group consisting of non-alcoholic fatty liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy.

32. The method of claim 31, wherein the fatty liver disease is non-alcoholic steatohepatitis (NASH).

33. A method of reducing fibrosis or fat content or fat accumulation in the liver associated with non-alcoholic fatty liver disease (NAFLD) comprising administering a compound of claim 1 to a subject in need thereof.

34. The method of claim 33, wherein the NALFD comprises NASH.

\* \* \* \* \*